US012760072B2

(12) United States Patent
Wimley et al.

(10) Patent No.: US 12,760,072 B2
(45) Date of Patent: Oct. 13, 2026

(54) BROAD-SPECTRUM ANTIVIRAL PEPTIDES

(71) Applicant: The Administrators of the Tulane Educational Fund, New Orleans, LA (US)

(72) Inventors: William Charles Wimley, New Orleans, LA (US); Andrew Robert Hoffmann, New Orleans, LA (US); Robert F. Garry, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 957 days.

(21) Appl. No.: 17/916,295

(22) PCT Filed: Mar. 31, 2021

(86) PCT No.: PCT/US2021/025280
§ 371 (c)(1),
(2) Date: Sep. 30, 2022

(87) PCT Pub. No.: WO2021/202816
PCT Pub. Date: Oct. 7, 2021

(65) Prior Publication Data
US 2023/0220010 A1 Jul. 13, 2023

Related U.S. Application Data

(60) Provisional application No. 63/002,522, filed on Mar. 31, 2020.

(51) Int. Cl.

| | |
|---|---|
| ***A61P 31/22*** | (2006.01) |
| ***A61K 39/215*** | (2006.01) |
| ***A61K 39/39*** | (2006.01) |
| ***A61P 31/14*** | (2006.01) |
| ***A61P 31/16*** | (2006.01) |
| ***C07K 7/06*** | (2006.01) |
| ***C07K 7/08*** | (2006.01) |
| ***C07K 14/00*** | (2006.01) |
| *A61K 39/00* | (2006.01) |

(52) U.S. Cl.
CPC .......... *C07K 14/001* (2013.01); *A61K 39/215* (2013.01); *A61K 39/39* (2013.01); *A61P 31/14* (2018.01); *A61P 31/16* (2018.01); *A61P 31/22* (2018.01); *C07K 7/06* (2013.01); *C07K 7/08* (2013.01); *A61K 2039/53* (2013.01); *A61K 2039/545* (2013.01); *A61K 2039/55516* (2013.01); *C12N 2770/20034* (2013.01); *C12N 2770/20071* (2013.01)

(58) Field of Classification Search
CPC ..... C07K 14/001; A61P 31/22; A61K 39/215; C12N 2770/20034
See application file for complete search history.

(56) References Cited

U.S. PATENT DOCUMENTS

| | | | | |
|---|---|---|---|---|
| 6,620,923 | B1 | 9/2003 | Specht et al. | |
| 7,745,391 | B2 | 6/2010 | Mintz et al. | |
| 8,603,966 | B2 * | 12/2013 | Wimley | G01N 33/5432 514/21.5 |
| 11,006,231 | B1 * | 5/2021 | Parker | H04R 27/04 |
| 11,149,068 | B2 | 10/2021 | Wimley et al. | |
| 11,266,743 | B2 | 3/2022 | Wimley et al. | |
| 2004/0123343 | A1 | 6/2004 | La Rosa et al. | |
| 2004/0147027 | A1 | 7/2004 | Troy et al. | |
| 2009/0099533 | A1 | 4/2009 | Montelaro et al. | |
| 2009/0203611 | A1 | 8/2009 | Zhang et al. | |
| 2009/0317395 | A1 | 12/2009 | Kofler et al. | |
| 2011/0110937 | A1 | 5/2011 | Simon | |
| 2011/0150917 | A1 | 6/2011 | Hancock et al. | |
| 2012/0017292 | A1 | 1/2012 | Kovalic et al. | |
| 2012/0178649 | A1 | 7/2012 | Watt et al. | |
| 2014/0024597 | A1 | 1/2014 | Troy et al. | |
| 2019/0192691 | A1 * | 6/2019 | Barrett | C07K 14/70517 |
| 2019/0211063 | A1 | 7/2019 | Wimley et al. | |
| 2019/0292234 | A1 | 9/2019 | Bachnoff et al. | |
| 2020/0276322 | A1 | 9/2020 | Wimley et al. | |

FOREIGN PATENT DOCUMENTS

| | | | | |
|---|---|---|---|---|
| CA | 2991223 A1 | 7/2019 | | |
| EP | 1724280 A1 | 11/2006 | | |
| EP | 2394665 A1 | 12/2011 | | |
| WO | WO-2011/056212 A1 | 5/2011 | | |
| WO | WO-2016/142445 A2 | 9/2016 | | |
| WO | WO 2017/180587 | 10/2017 | * | C12Q 1/68 |
| WO | WO-2018/091523 A1 | 5/2018 | | |
| WO | WO-2019/084343 A1 | 5/2019 | | |

OTHER PUBLICATIONS

Anonymous, "UPI0007A1D356," UniParc, UniProt. Accessed Dec. 2, 2024, (Apr. 2016) (4 pages).
Badani et al., "Peptide entry inhibitors of enveloped viruses: the importance of interfacial hydrophobicity," Biochim Biophys Acta. 1838(9):2180-97 (Sep. 2014).
Extended European Search Report for European Patent Application No. 21754083.0 dated Jan. 29, 2024 (8 pages).

(Continued)

*Primary Examiner* — Amber D Steele
(74) *Attorney, Agent, or Firm* — Thomas Horstemeyer LLP.

(57) ABSTRACT

Described herein are antiviral peptides, polynucleotides encoding the peptides, and compositions containing the peptides. Furthermore, described herein are methods for using the peptides, polynucleotides, and compositions for treating or inhibiting a viral infection or one or more symptoms of a viral infection.

16 Claims, 40 Drawing Sheets

Specification includes a Sequence Listing.

(56) References Cited

OTHER PUBLICATIONS

Extended European Search Report for European Patent Application No. 21780752.8, dated Feb. 23, 2024 (22 pages).
He et al., "Novel Antiviral Agents: Design, Identification and Characterization of Interfacially Active Peptide Entry inhibitors," FASEB J. 29(S1):886.20 (Apr. 2015) (2 pages).
Hoffmann et al., "Broad-Spectrum Antiviral Entry Inhibition by Interfacially Active Peptides," J Virol. 94(23):e01682-20 (Nov. 2020) (20 pages).
Hoffmann, "Randomly Selected Hydrophobic Peptide Inhibit Lassa Pseudovirus," Biophys J. 108(2):83a (Feb. 2015) (1 page).
Hoffmann, Andrew Robert, Dissertation: "Discovery and Design of Broad-Spectrum Antiviral Peptides," Ph.D., Tulane University, Mar. 2020 (194 pages).
Office Action for Canadian Patent Application No. 3,167,422, dated Jan. 24, 2024 (5 pages).
Akinc et al., "Exploring polyethylenimine-mediated DNA transfection and the proton sponge hypothesis," J Gene Med. 7(5):657-663 (2005).
An et al., "pH-(low)-insertion-peptide (pHLIP) translocation of membrane impermeable phalloidin toxin inhibits cancer cell proliferation," Proc Natl Acad Sci U S A. 107(47):20246-20250 (2010).
Andreev et al., "pH-sensitive membrane peptides (pHLIPs) as a novel class of delivery agents," available in PMC Dec. 25, 2015, published in final edited form as: Mol Membr Biol. 27(7):341-352 (2010) (21 pages).
Atherton et al., "Solid-Phase Peptide Synthesis: A Practical Approach," Febs Letters. 265(1,2):152 (1990) (1 page).
Bechinger, "Peptide-nucleic acid nanostructures for transfection," Biomol Concepts. 3(3):283-293 (2012).
Bechinger, "Structure and function of membrane-lytic peptides," Critical Reviews in Plant Sciences. 23(3):1-22 (2004) (23 pages).
Brown et al., "Cationic host defense (antimicrobial) peptides," Curr Opin Immunol. 18(1): 24-30 (2006).
Chang et al., "Characterization of antimicrobial peptide activity by electrochemical impedance spectroscopy," available in PMC Oct. 1, 2009, published in final edited form as: Biochim Biophys Acta. 1778(10):2430-36 (2008) (16 pages).
Chen et al., "Simulation-Guided Rational de Novo Design of a Small Pore-Forming Antimicrobial Peptide," J Am Chem Soc. 141(12):4839-48 (2019) (1 page) (Abstract only).
Dempsey, "The action of melittin on membranes," Biochim Biophys Acta. 1031(2):143-161 (1990).
Duncan, "The dawning era of polymer therapeutics," Nat Rev Drug Discov. 2(5):347-360 (2003).
Endoh et al., "Cellular siRNA delivery using cell-penetrating peptides modified for endosomal escape," Adv Drug Deliv Rev. 61(9):704-709 (2009).
Erazo-Oliveras et al., "Improving the endosomal escape of cell-penetrating peptides and their cargos: strategies and challenges," Pharmaceuticals (Basel). 5(11):1177-1209 (2012).
Extended European Search Report for European Patent Application No. 18871046.1 dated Oct. 22, 2021 (13 pages).
Farrand et al., "The Cholesterol-dependent Cytolysin Membrane-binding Interface Discriminates Lipid Environments of Cholesterol to Support beta-Barrel Pore Insertion," J Biol Chem. 290(29):17733-44 (2015).
Fendos et al., "Aspartate Embedding Depth Affects pHLIP's Insertion pKa," available in PMC Jul. 9, 2014, published in final edited form as: Biochemistry. 52(27):4595-4604 (2013).
Ganz et al., "Defensins," Eur J Haematol. 44(1):1-8 (1990).
Gerlach et al., "Anticancer and chemosensitizing abilities of cycloviolacin 02 from Viola odorata and psyle cyclotides from Psychotria leptothyrsa," Biopolymers. 94(5):617-25 (2010).
Gillies et al., "Causes and consequences of increased glucose metabolism of cancers," J Nucl Med. 49(Suppl 2):24S-42S (2008) (20 pages).
He et al., "A Lack of Synergy Between Membrane-permeabilizing Cationic Antimicrobial Peptides and Conventional Antibiotics," available in PMC Jan. 1, 2016, published in final edited form as: Biochim Biophys Acta. 1848(100):8-15 (2015) (21 pages).
He et al., "Toward the de novo design of antimicrobial peptides: Lack of correlation between peptide permeabilization of lipid vesicles and antimicrobial, cytolytic, or cytotoxic activity in living cells," available in PMC Jan. 1, 2015, published in final edited form as: Biopolymers. 102(1):1-6 (2014) (10 pages).
Heitz et al., "Twenty years of cell-penetrating peptides: from molecular mechanisms to therapeutics," Br J Pharmacol. 157(2):195-206 (2009).
Hristova et al., "A look at arginine in membranes," available in PMC Jan. 1, 2012, published in final edited form as: J Membr Biol. 239(1-2):49-56 (2011) (13 pages).
Hällbrink et al., "Cargo delivery kinetics of cell-penetrating peptides," Biochim Biophys Acta. 1515(2):101-109 (2001).
International Preliminary Report on Patentability for International Application No. PCT/US18/57614, mailed Apr. 28, 2020 (7 pages).
International Preliminary Report on Patentability for International Patent Application No. PCT/US2021/018031, issued Aug. 11, 2022 (11 pages).
International Search Report and Written Opinion for International Application No. PCT/US18/57614, mailed Feb. 25, 2019 (17 pages).
International Search Report and Written Opinion for International Patent Application No. PCT/US2021/018031, mailed May 13, 2021 (14 pages).
Kakudo et al., "Transferrin-Modified Liposomes Equipped with a pH-Sensitive Fusogenic Peptide: An Artificial Viral-like Delivery System," Biochemistry. 43(19):5618-5628 (2004) (11 pages).
Kauffman et al., "Mechanism Matters: A Taxonomy of Cell Penetrating Peptides," available in PMC Dec. 1, 2016, published in final edited form as: Trends Biochem Sci. 40(12):749-764 (2015) (28 pages).
Komin et al., "Peptide-based strategies for enhanced cell uptake, transcellular transport, and circulation: Mechanisms and challenges," Adv Drug Deliv Rev. 110-111:52-64 (2017).
Krauson et al., "Conformational Fine-Tuning of Pore-Forming Peptide Potency and Selectivity," J Am Chem Soc. 137(51): 16144-52 (2015).
Krauson et al., "Determining the mechanism of membrane permeabilizing peptides: Identification of potent, equilibrium pore-formers," available in PMC Jul. 1, 2013, published in final edited form as: Biochim Biophys Acta. 1818(7):1625-32 (2012) (20 pages).
Krauson et al., "Gain-of-Function Analogues of the Pore-Forming Peptide Melittin Selected by Orthogonal High-Throughput Screening," available in PMC Aug. 1, 2013, published in final edited form as: J Am Chem Soc. 134(30):12732-12741 (2012) (20 pages).
Krauson et al., "Synthetic molecular evolution of pore-forming peptides by Iterative combinatorial library screening," available in PMC Apr. 19, 2014, published in final edited form as: ACS Chem Biol. 8(4):823-31 (2013) (18 pages).
Kullberg et al., "Listeriolysin O enhances cytoplasmic delivery by Her-2 targeting liposomes," J Drug Target. 18(4):313-320 (2010) (9 pages).
Ladokhin et al., "Leakage of Membrane Vesicle Contents: Determination of Mechanism Using Fluorescence Requenching," Biophys J. 69(5):1964-71 (1995).
Lam et al., "Effective endogenous gene silencing mediated by pH responsive peptides proceeds via multiple pathways," available in PMC Mar. 21, 2012, published in final edited form as: J Control Release. 158(2):293-303 (2012) (23 pages).
Lam et al., "Effective endogenous gene silencing mediated by pH responsive peptides proceeds via multiple pathways," J Control Release. Mar. 10, 2012;158(2):293-303. doi: 10.1016/j.jconrel.2011.11.024. Epub Nov. 26, 2011. PMID: 22138072; PMCID: PMC3309421.
Lehrer et al., "Defensins: Endogenous Antibiotic Peptides of Animal Cells," Cell. 64(2):229-230 (1991) (2 pages).
LifeTein, "The Cationic Host Defense Peptides Could Be Used to Kill Enveloped Novel Coronavirus SARS-CoV-2", <URL:https://www.lifetein.com/blog/the-cationic-host-defense-peptides-could-be-used-to-kill-enveloped-novel-coronavirus-sars-cov-2/>, dated Feb. 28, 2020, retrieved Jul. 1, 2021 (5 pages).

(56) References Cited

OTHER PUBLICATIONS

Lin et al., “Interactions of membrane active peptides with planar supported bilayers: an impedance spectroscopy study,” Langmuir. 28(14):6088-96 (2012) (1 page) (Abstract only).
Maiolo et al., “Specific Redistribution of Cell-Penetrating Peptides from Endosomes to the Cytoplasm and Nucleus upon Laser Illumination,” J Am Chem Soc. 126(47):15376-15377 (2004) (2 pages).
Mayer et al., “Vesicles of variable sizes produced by a rapid extrusion procedure,” Biochim Biophys Acta. 858(1):161-168 (1986).
Muro, “Challenges in design and characterization of ligand-targeted drug delivery systems,” available in PMC Dec. 10, 2013, available in final edited form as: J Control Release. 164(2):125-137 (2012) (33 pages).
Nishimura et al., “A display of pH-sensitive fusogenic GALA peptide facilitates endosomal escape from a Bio-nanocapsule via an endocytic uptake pathway,” J Nanobiotechnology. 12:11 (2014) (6 pages).
Oliveira et al., “Fusogenic peptides enhance endosomal escape improving siRNA-induced silencing of oncogenes,” Int J Pharm. 331(2):211-214 (2007).
Pantaleo et al., “Molecular imaging and targeted therapies in oncology: New concepts in treatment response assessment. A collection of cases,” Int J Oncol. 33(3):443-452 (2008).
Parente et al., “Mechanism of Leakage of Phospholipid Vesicle Contents Induced by the Peptide GALA,” Biochemistry. 29(37): 8720-8728 (1990) (9 pages).
Parente et al., “Association of a pH-Sensitive Peptide with Membrane Vesicles: Role of Amino Acid Sequence,” Biochemistry. 29(37): 8713-8719 (1990) (7 pages).
Rathinakumar et al., “Biomolecular engineering by combinatorial design and high-throughput screening: small, soluble peptides that permeabilize membranes,” available in PMC Nov. 13, 2008, published in final edited form as: J Am Chem Soc. 130(30):9849-9858 (2008) (26 pages).
Rathinakumar et al., “Broad-spectrum Antimicrobial Peptides by Rational Combinatorial Design and High-throughput Screening: The Importance of Interfacial Activity,” available in PMC Sep. 8, 2010, published in final edited form as: J Am Chem Soc. 131(22):7609-17 (2009) (23 pages).
Rathinakumar et al., “High-throughput discovery of broad-spectrum peptide antibiotics,” FASEB J. 24(9):3232-38 (2010) (11 pages).
Rausch et al., “A high-throughput screen for identifying transmembrane pore-forming peptides,” Anal Biochem. 293(2):258-63 (2001).
Rausch et al., “Beta-Sheet Pore-Forming Peptides Selected from a Rational Combinatorial Library: Mechanism of Pore Formation in Lipid Vesicles and Activity in Biological Membranes,” available in PMC Nov. 14, 2008, published in final edited form as: Biochemistry. 46(43):12124-39 (2007) (37 pages).
Rausch et al., “Rational combinatorial design of pore-forming beta-sheet peptides,” Proc Natl Acad Sci U S A. 102(30):10511-10515 (2005).
Räägel et al., “Peptide-mediated protein delivery—Which pathways are penetrable?” Biochim Biophys Acta. 1798(12):2240-2248 (2010).
Shai et al., “From ‘carpet’ mechanism to de-novo designed diastereomeric cell-selective antimicrobial peptides,” Peptides. 22(10):1629-1641 (2001).
Snider et al., “MPEx: A tool for exploring membrane proteins,” Protein Sci. 18(12):2624-2628 (2009).
Soman et al., “Molecularly targeted nanocarriers deliver the cytolytic peptide melittin specifically to tumor cells in mice, reducing tumor growth,” J Clin Invest. 119(9):2830-2842 (2009).
Starr et al., “Antimicrobial peptides are degraded by the cytosolic proteases of human erythrocytes,” available in PMC Dec. 1, 2018, published in final edited form as: Biochim Biophys Acta. 1859(12):2319-26 (2017) (20 pages).
Starr et al., “Host Cell Interactions are a Significant Barrier to the Clinical Utility of Peptide Antibiotics,” available in PMC Jul. 21, 2017, published in final edited form as: ACS Chem Biol. 11(12):3391-99 (2016) (18 pages).
Starr et al., “Pituitary adenylate cyclase-activating polypeptide is a potent broad-spectrum antimicrobial peptide: Structure-activity relationships,” available in PMC Jun. 1, 2019, published in final edited form as: Peptides. 104:35-40 (2018) (19 pages).
Starr et al., “Synthetic molecular evolution of host cell-compatible, antimicrobial peptides effective against drug-resistant, biofilm-forming bacteria,” Proc Natl Acad Sci U S A. 117(15):8437-48 (Apr. 2020) (8 pages) (Abstract only).
Subbarao et al., “pH-Dependent Bilayer Destabilization by an Amphipathic Peptide,” Biochemistry. 26(11):2964-2972 (1987) (9 pages).
Supplementary Partial European Search Report for European Patent Application No. 18871046.1, dated Jul. 22, 2021 (15 pages).
Van Dyke, “Acidification of Lysosomes and Endosomes,” Subcell Biochem. 27:331-360 (1996) (30 pages).
Varkouhi et al., “Endosomal escape pathways for delivery of biologicals,” J Control Release. 151(3):220-228 (2011).
Walkenhorst et al., “pH Dependence of Microbe Sterilization by Cationic Antimicrobial Peptides,” Antimicrob Agents Chemother. 57(7) 2013:3312-20 (2013).
Wang et al., “Burkholderia thailandensis outer membrane vesicles exert antimicrobial activity against drug-resistant and competitor microbial species,” J Microbiol. 58(7):550-62 (Jul. 2020) (1 page) (Abstract only).
White et al., “Protein folding in membranes: Determining the energetics of peptide-bilayer interactions,” Methods Enzymol. 295:62-87 (1998).
White et al., “Structure, function, and membrane integration of defensins,” Curr Opin Struct Biol. 5(4):521-7 (1995) (1 page) (Abstract only).
Wiedman et al., “Highly Efficient Macromolecule-Sized Poration of Lipid Bilayers by a Synthetically Evolved Peptide,” J Am Chem Soc. 136(12): 4724-31 (2014).
Wiedman et al., “PH-Triggered, Macromolecule-Sized Poration of Lipid Bilayers by Synthetically Evolved Peptides,” available in PMC Jul. 21, 2017, published in final edited form as: J Am Chem Soc. 139(2):937-45 (2017) (22 pages).
Wiedman et al., “Testing the limits of rational design by engineering pH sensitivity into membrane active peptides,” available in PMC Apr. 1, 2016, published in final edited form as: Biochim Biophys Acta. 1848(4):951-7 (2015) (15 pages).
Wiedman et al., “The electrical response of bilayers to the bee venom toxin melittin: Evidence for transient bilayer permeabilization,” available in PMC May 14, 2014, published in final edited form as: Biochim Biophys Acta. 1828(5):1357-1364 (2013) (21 pages).
Wimley et al., “Antimicrobial Peptides: successes, challenges and unanswered questions,” available in PMC Sep. 2, 2011, published in final edited form as: J Membr Biol. 239(1-2):27-34 (2011) (12 pages).
Wimley et al., “Determining the membrane topology of peptides by fluorescence quenching,” Biochemistry. 39(1):161-70 (2000).
Wimley et al., “Folding of beta-sheet membrane proteins: a hydrophobic hexapeptide model,” J Mol Biol. 277(5):1091-1110 (1998).
Wimley et al., “Interactions between human defensins and lipid bilayers: evidence for formation of multimeric pores,” Protein Sci. 3(9):1362-73 (1994).
Wimley et al., “The Mechanism of Membrane Permeabilization by Peptides: Still an Enigma,” available in PMC Apr. 27, 2020, published in final edited form as: Aust J Chem. 73(3):96-103 (2019) (16 pages).
Wimley, “Application of Synthetic Molecular Evolution to the Discovery of Antimicrobial Peptides,” available in PMC Oct. 8, 2019, published in final edited form as: Adv Exp Med Biol. 1117: 241-255 (2019) (20 pages).
Wimley, “Describing the Mechanism of Antimicrobial Peptide Action with the Interfacial Activity Model,” available in PMC Oct. 15, 2011, published in final edited form as: ACS Chem Biol. 15(10):905-17 (2010) (21 pages).
Wimley, “Energetics of peptide and Protein Binding to Lipid Membranes,” Adv Exp Med Biol. 677:14-23 (2010) (10 pages).

(56) References Cited

OTHER PUBLICATIONS

Yao et al., "pHLIP®-mediated delivery of PEGylated liposomes to cancer cells," available in PMC May 10, 2014, published in final edited form as: J Control Release. 167(3):228-237 (2013) (24 pages).

Yu et al., "Overcoming Endosomal Barrier by Amphotericin B-Loaded Dual pH-Responsive PDMA-b-PDPA Micelleplexes for siRNA Delivery," available in PMC Mar. 18, 2016, published in final edited form as: ACS Nano. 5(11):9246-9255 (2011) (21 pages).

Starr et al., "Synthetic molecular evolution of host cell-compatible, antimicrobial peptides effective against drug-resistant, biofilm-forming bacteria," Proc Natl Acad Sci USA. 117(15):8437-8448. (Apr. 2020).

* cited by examiner

| | | SEQ ID NO: |
|---|---|---|
| IT1b | R R G F S L K L A L L K D G W L L L R L G Y G R R | 44 |
| Nterm | R R G F S L K L A L L - - - - - - - - - - - - - - | 54 |
| Nterm-Cat | R R G F S L K L A L L K - - - - - - - - - - - - - | 55 |
| Mid | - - - - - - - L A L L K D G W L L L - - - - - - - | 56 |
| Mid-Cat | - - - - - - K L A L L K D G W L L L R - - - - - - | 57 |
| Cterm | - - - - - - - - - - - - - - W L L L R L G Y G R R | 58 |
| Cterm-Cat | - - - - - - - - - - - K D G W L L L R L G Y G R R | 59 |

5 Minute Incubation

1 Minute Incubation

| SEQ ID NO: | | Sequence | Solubility | $EC_{50}$ (μM) | $CC_{50}$ (μM) | Index |
|---|---|---|---|---|---|---|
| 42 | IT1b | RRGFSLKLALLKDGWLLLRLGYGRR | $H_2O$ | 0.537 | 7.9 | 14.8 |
| | | | | | | |
| 3 | TL3 | RRGWLLLRLLLWGRR | $H_2O$ | 0.931 | 15.2 | 16.3 |
| 4 | TL1 | RRGWLRLWGRR | $H_2O$ | >50 | >50 | ND |
| 5 | TL2 | RRGWLLRLLWGRR | $H_2O$ | 6.386 | 10.1 | 1.6 |
| 6 | TAS | RRGWLLLRLWGRR | $H_2O$ | 12.135 | 31.7 | 2.6 |
| | | | | | | |
| 7 | R2 | RRGWLLRLLRLLWGRR | $H_2O$ | 0.840 | 4.1 | 4.9 |
| 8 | R5 | RRGWLRLRLRLRLRLWGRR | $H_2O$ | 1.109 | 8.2 | 7.4 |
| 9 | N1 | RRGWLLLNLLLWGRR | $H_2O$ | 1.223 | >50 | >40.9 |
| 10 | N2 | RRGWLLNLLNLLWGRR | $H_2O$ | 0.900 | 5.1 | 5.6 |
| 11 | W1 | RRGWLLLWLLLWGRR | 50% DMSO | 2.280 | 10.7 | 4.7 |
| 12 | W2 | RRGWLLWLLWLLWGRR | 50% DMSO | 0.612 | 7.8 | 12.8 |
| | | | | | | |
| 13 | HF3 | RRGWLLLRLLLRLLLWGRR | $H_2O$ | 0.368 | 8.1 | 22.0 |
| 14 | HF4 | RRGWLLLRLLLRLLLRLLLWGRR | $H_2O$ | 0.442 | 15.1 | 34.1 |
| 15 | AHR | RRGWLLLRLLRLLLRLLWGRR | $H_2O$ | 0.325 | 6.4 | 19.6 |
| 17 | MFR | RRGWLLLRLLLRGGGGRLLLRLLLWGRR | $H_2O$ | 0.548 | 18.9 | 34.5 |
| 18 | MFG | RRGWLLLRLLLGGGGLLLRLLLWGRR | 50% DMSO | 0.424 | 9.6 | 22.7 |
| 19 | MFW | RRGWLLLRLLLWGGGGWLLLRLLLWGRR | 50% DMSO | 0.647 | 12.5 | 19.3 |
| | | | | | | |
| 20 | TL4 | RRGWLLLLRLLLLWGRR | $H_2O$ | 0.697 | 8.0 | 11.5 |
| 21 | TL4N | RRGWLLLLNLLLLWGRR | $H_2O$ | 0.564 | >50 | >88.7 |
| 22 | TL4dG | RRWLLLLRLLLLWRR | $H_2O$ | 0.772 | 36.0 | 46.6 |
| 23 | TL4NdG | RRWLLLLNLLLLWRR | $H_2O$ | 1.703 | >50 | >29.4 |
| | | | | | | |
| 25 | TL4FRL | RRWLLFLRLFLLWRR | $H_2O$ | 0.884 | 26.6 | 30.0 |
| 26 | TL4ARL | RRWLLALRLALLWRR | $H_2O$ | 0.799 | 30.6 | 38.2 |
| 27 | TL4FRW | RRWLLLLRLLLLFRR | $H_2O$ | 1.771 | 29.9 | 16.9 |
| 28 | TL3FL | RRWLLLGRLLLWRR | $H_2O$ | 13.201 | 15.6 | 1.2 |
| | | | | 17% | 83% | 61% |

FIG. 23

BROAD-SPECTRUM ANTIVIRAL PEPTIDES

STATEMENT REGARDING FEDERALLY SPONSORED RESEARCH

This invention was made with government support under Grant No. AI132223, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created Mar. 31 2021, is named 07005-022WO2_Sequence_Listing_3_31_2021_ST25 and is 28,147 bytes in size.

BACKGROUND

Viral disease is among the leading causes of death globally. Epidemics of emerging infectious diseases often have no specific treatments, leaving most patients to be treated with only supportive care. Broad-spectrum antiviral drugs could help ease this burden especially in situations where diagnostics are limited. Early administration of treatment is important, as the treatment windows for drugs are short due to possible emergence of viral resistance that reduces drug efficacy.

Broad-spectrum antiviral peptides show great promise as antiviral agents. There are many advantages to peptide drugs as antiviral agents. Peptides have high potency, predictable metabolism, and can be developed for a broad range of targets. Peptides can also have excellent target specificity, resulting in little to no side effects, a common issue for small molecules. Due to the development of solid phase peptide synthesis, numerous sequences can be readily synthesized. This method lowers production costs, giving these drugs an advantage over large protein-based biopharmaceuticals. Due to the variability in sequence design, peptides can be used to treat a wide variety of viral infections.

There is an urgent need to develop novel peptides that are effective against viral pathogens and have broad-spectrum antiviral activity in order to address outbreaks of viral diseases.

SUMMARY OF THE DISCLOSURE

A first aspect of the disclosure features a polypeptide with at least 75% (e.g., at least 80%, 85%, 90%, 95%, 97%, or 100%) sequence identity to the sequence of any one of SEQ ID NOs: 1-47 and 54-59, such as, e.g., a polypeptide with at least 75% (e.g., at least 80%, 85%, 90%, 95%, 97%, or 100%) sequence identity to the sequence of any one of SEQ ID NOs: 1-28. In particular, the polypeptide has the sequence of SEQ ID NO: 15 or 21. The polypeptides are antiviral peptides, such as polypeptides exhibiting an ability to disrupt the infectivity of multiple viral pathogens (e.g., adenoviruses (e.g., human adenovirus type 1 (HAdV-1), HAdV-2, HAdV-3, HAdV-4, HAdV-5, HAdV-6, HAdV-7)), MERS-CoV, SARS-CoV, SARS-CoV-2 or variants thereof, dengue viruses (e.g., DENV-1, DENV-2, DENV-3, DENV-4, DENV-5), ebolaviruses (e.g., Ebola virus (Zaire ebolavirus sp.), Sudan virus (Sudan ebolavirus sp.), Tar Forest virus (Taï Forest ebolavirus sp., formerly Cote d'Ivoire ebolavirus), Bundibugyo virus (Bundibugyo ebolavirus sp.), Reston virus (Reston ebolavirus sp.)), Marburg virus (e.g., Marburgvirus sp. (e.g., Marburg virus (MARV) and Ravn virus (RAVV))), human immunodeficiency viruses (e.g., HIV-1 and HIV-2), hepatitis B virus, hepatitis C virus, hepatitis D virus, herpesviruses simplex viruses (e.g., herpes simplex virus type 1 (HSV-1), herpes simplex virus type 2 (HSV-2), cytomegalovirus (e.g., human cytomegalovirus (HCMV)), Epstein-Barr virus (EBV), human herpesvirus 6 (e.g., HHV-6A and HHV-6B), human herpesvirus 7 (HHV-7), Kaposi's sarcoma-associated herpesvirus (KSHV; also known as human herpesvirus 8 (HHV-8)), varicella-zoster virus (VZV)), influenza A virus (e.g., subtypes H1N1, H3N2, H5N1), and influenza B viruses (e.g., B/Yamagata and BNictoria), influenza C virus, influenza D virus, Lassa virus, respiratory syncytial virus (RSV), human metapneumovirus (hMPV), parainfluenza viruses (e.g., human parainfluenza virus type 1 (HPIV-1), HPIV-2, HPIV-3, HPIV-4), measles virus (MV), West Nile virus (WNV), yellow fever virus, Zika virus (ZIKV), chikungunya virus (CHIKV), Nipah virus (NIV), and Hendra virus (HeV), feline immunodeficiency virus (FIV), feline leukemia virus (FeLV), canine distemper virus (CDV), canine parvovirus (CPV), bovine viral diarrhea (BVD) virus, bovine leukemia virus (BLV)).

The polypeptides may also have one or more D-amino acids (e.g., D-ALA, D-ARG, D-ASN, D-ASP, D-CYS, D-GLN, D-GLU, D-HIS, D-ILE, D LEU, D-LYS, D-MET, D-PHE, D-PRO, D-SER, D-THR, D-TRP, D-TYR, and D-VAL), one or more L-amino acids, or a mixture of D- and L-amino acids. The polypeptides may be 5-34 amino acids long (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, or 34 amino acids).

A second aspect of the disclosure features a polynucleotide encoding the polypeptide of the first aspect.

A third aspect of the disclosure features a vector containing the polynucleotide of the second aspect encoding the polypeptide of the first aspect.

A fourth aspect of the disclosure features a composition comprising the polypeptide of the first aspect, the polynucleotide of the second aspect, or the vector of the third aspect. The composition may also include a pharmaceutically acceptable carrier, excipient, or diluent. The composition may further include a therapeutic agent. In particular, the therapeutic agent can be an antiviral agent, such as Abacavir, Acyclovir, Adefovir dipivoxil, Amantadine, Amprenavir, Asunaprevir, Atazanavir, Boceprevir, Brivudine, Cidofovir, Daclatasvir, Darunavir, Dasabuvir, Delavirdine, Didanosine, Docosanol, Dolutegravir, Dolutegravir, Efavirenz, EIDD-2801, Elbasvir, Elvitegravir, Emtricitabine, Enfuvirtide, Entecavir, Etravirine, Famciclovir, Favipiravir (favilavir), Fosamprenavir, Foscarnet, Galidesivir, Ganciclovir, Grazoprevir, Idoxuridine, Indinavir, Lamivudine, Laninamivir octanoate, Ledipasvir, Lopinavir, Maraviroc, Nelfinavir, Nevirapine, Ombitasvir, Oseltamivir, Palivizumab, Paritaprevir, Penciclovir, Peramivir, Raltegravir, Remdesivir, Ribavirin, Rilpivirine, Rimantadine, Ritonavir, RSV-IGIV, Saquinavir, Simeprevir, SNG001, Sofosbuvir, Stavudine, Telaprevir, Telbivudine, Tenofovir alafenamide, Tenofovir disoproxil fumarate, Tipranavir, Trifluridine, Valacyclovir, Valganciclovir, Vaniprevir, Vidarabine, Zalcitabine, Zanamivir, Zidovudine, or pharmaceutically acceptable salts thereof, or a combination thereof. In some embodiments, the composition of the fourth aspect is a liquid or a solid. In certain embodiments, the polypeptide in the composition of the fourth aspect of the invention can be provided as an injectable solution, suspension, or emulsion, and administered via intramuscular, subcutaneous, intradermal, intracavity, parenteral, epidermal, intraarterial, intraperitoneal, or intravenous injection using conventional methods, such as a syringe, or using a liquid jet injection system.

A fifth aspect of the disclosure features a method of treating a viral infection by administering the composition of the fourth aspect (e.g., a polypeptide with at least 75% (e.g., at least 80%, 85%, 90%, 95%, 97%, or 100%) sequence identity to the sequence of any one of SEQ ID NOs: 1-47 and 54-59, such as, e.g., a polypeptide with at least 75% (e.g., at least 80%, 85%, 90%, 95%, 97%, or 100%) sequence identity to the sequence of any one of SEQ ID NOs: 1-28; e.g., the polypeptide of SEQ ID NO: 15, 21, 32, or 42) to a subject (e.g., a human or animal, e.g., a mammal, such as a non-human primate, bovine, equine, canine, ovine, and feline) with or suspected of having an infection. In particular, the viral infection can be caused by a viral pathogen (e.g., adenoviruses (e.g., human adenovirus type 1 (HAdV-1), HAdV-2, HAdV-3, HAdV-4, HAdV-5, HAdV-6, HAdV-7)), MERS-CoV, SARS-CoV, SARS-CoV-2 or variants thereof, dengue viruses (e.g., DENV-1, DENV-2, DENV-3, DENV-4, DENV-5), ebolaviruses (e.g., Ebola virus (Zaire ebolavirus sp.), Sudan virus (Sudan ebolavirus sp.), TaT Forest virus (TaT Forest ebolavirus sp., formerly Cote d'Ivoire ebolavirus), Bundibugyo virus (Bundibugyo ebolavirus sp.), Reston virus (Reston ebolavirus sp.)), Marburg virus (e.g., Marburg Marburgvirus sp. (e.g., Marburg virus (MARV) and Ravn virus (RAVV))), human immunodeficiency viruses (e.g., HIV-1 and HIV-2), hepatitis B virus, hepatitis C virus, hepatitis D virus, herpesviruses simplex viruses (e.g., herpes simplex virus type 1 (HSV-1), herpes simplex virus type 2 (HSV-2), cytomegalovirus (e.g., human cytomegalovirus (HCMV)), Epstein-Barr virus (EBV), human herpesvirus 6 (e.g., HHV-6A and HHV-6B), human herpesvirus 7 (HHV-7), Kaposi's sarcoma-associated herpesvirus (KSHV; also known as human herpesvirus 8 (HHV-8)), varicella-zoster virus (VZV)), influenza A virus (e.g., subtypes H1N1, H3N2, H5N1), and influenza B viruses (e.g., B/Yamagata and B/Victoria), influenza C virus, influenza D virus, Lassa virus, respiratory syncytial virus (RSV), human metapneumovirus (hMPV), parainfluenza viruses (e.g., human parainfluenza virus type 1 (HPIV-1), HPIV-2, HPIV-3, HPIV-4), measles virus (MV), West Nile virus (WNV), yellow fever virus, Zika virus (ZIKV), chikungunya virus (CHIKV), Nipah virus (NIV), and Hendra virus (HeV), feline immunodeficiency virus (FIV), feline leukemia virus (FelV), canine distemper virus (CDV), canine parvovirus (CPV), bovine viral diarrhea (BVD) virus, bovine leukemia virus (BLV)). In particular, the viral infection is caused by SARS-CoV-2 or variants thereof.

The compositions described herein (e.g., a composition containing an amount (e.g., an effective antiviral amount) of a peptide of any one of SEQ ID NOs: 1-47 and 54-59, such as a peptide of SEQ ID NO: 15 or 21) may be used for treating a viral infection in a subject (e.g., a human or other mammal, such as a bovine, equine, canine, ovine, or feline). The viral infection may be, e.g., a SARS-CoV-2 or a variant thereof infection. The composition can be administered systemically to treat the infection.

A sixth aspect of the disclosure features a method of producing the polypeptide of the first aspect of the disclosure (e.g., an antiviral peptide, such as a polypeptide with at least 75% (e.g., at least 80%, 85%, 90%, 95%, 97%, or 100%) sequence identity to the sequence of any one of SEQ ID NOs: 1-47 and 54-59, such as, e.g., a polypeptide with at least 75% (e.g., at least 80%, 85%, 90%, 95%, 97%, or 100%) sequence identity to the sequence of any one of SEQ ID NOs: 1-28, in particular a peptide of SEQ ID NOs: 1-28, e.g., a peptide of SEQ ID NO: 15 or 21) using chemical peptide synthesis (e.g., solid phase peptide synthesis) or recombinant expression, e.g., in a cell, such as a prokaryotic cell (e.g., *E. coli*) or a eukaryotic cell (e.g., a HeLa, CHO, or HEK cell). In particular, the method of chemical peptide synthesis can feature the use of Fmoc and/or Boe synthesis.

A seventh aspect of the disclosure features a method of manufacturing the polypeptides of the first aspect by expressing the polypeptide in a cell, such as a prokaryotic cell (e.g., *E. coli*) or a eukaryotic cell (e.g., a Hela, CHO, or HEK cell cell), that has been transformed with a polynucleotide of the second aspect (e.g., the polynucleotide may be present in a vector of the third aspect), and then recovering the polypeptide from the cell or the culture media surrounding the cell.

An eighth aspect of the disclosure features a kit comprising the polypeptide of the first aspect (such as a polypeptide with at least 75% (e.g., at least 80%, 85%, 90%, 95%, 97%, or 100%) sequence identity to the sequence of any one of SEQ ID NOs: 1-47 and 54-59, such as, e.g., a polypeptide with at least 75% (e.g., at least 80%, 85%, 90%, 95%, 97%, or 100%) sequence identity to the sequence of any one of SEQ ID NOs: 1-28, in particular a peptide of SEQ ID NOs: 1-28, e.g., a peptide of SEQ ID NO: 15 or 21), the polynucleotide of the second aspect, the vector of the third aspect, or the composition of the fourth aspect, and, optionally, an antiviral agent (e.g., an antiviral agent, such as oseltamivir phosphate). The kit component(s) can be used for the manufacture of a medicament for the treatment, prevention, or reduction in severity of a viral infection (e.g., a viral infection of the fifth aspect of the disclosure, such as a respiratory illness (e.g., pneumonia) in a subject (e.g., a human or other non-human mammal, such as a non-human primate, bovine, equine, canine, ovine, or feline)). The kit may also include a therapeutic agent, such as an antiviral agent, an antiviral vaccine, an antimicrobial agent (such as an antibacterial agent or an antifungal agent), an anti-inflammatory agent, or an antiparasitic agent, a nucleic acid, a peptide, a protein, a contrast agent, an antibody, a toxin, or a small molecule.

Definitions

As used herein, the term "acidic amino acid" refers to an amino acid having a side chain containing a carboxylic acid group having a pKa between 3.5 and 4.5. Acidic amino acids are aspartic acid and glutamic acid.

The term "about" means±10% of the stated amount.

As used herein, the term "basic amino acid" refers to an amino acid whose side chain contains an amino group having a pKa between 6.5 and 13 (e.g., between 9.5 and 13). Basic amino acids are histidine, lysine, and arginine.

As used herein, a "coding region" is a portion of the nucleic acid which contains codons that can be translated into amino acids. Although a "stop codon" (TAG, TGA, TAA) is not translated into an amino acid, it may be considered to be part of a coding region, if present, but any flanking sequences, for example, promoters, ribosome binding sites, transcriptional terminators, intrans, 5' and 3' untranslated regions, and the like, are not part of the coding region.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is, therefore, interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "host cell" refers to any kind of cellular system that can be engineered to generate the antiviral peptides (AVPs) described herein.

As used herein, the term "nonpolar amino acid" refers to an amino acid having relatively low-water solubility. Nonpolar amino acids are glycine, leucine, isoleucine, alanine, phenylalanine, methionine, tryptophan, valine, and praline.

As used herein, the term "percent (%) identity" refers to the percentage of amino acid residues of a candidate sequence that are identical to the amino acid residues of a reference sequence, e.g., an AVP disclosed herein, after aligning the sequences and introducing gaps, if necessary, to achieve the maximum percent identity (e.g., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid sequence identity of a given candidate sequence to, with, or against a given reference sequence (which can alternatively be phrased as a given candidate sequence that has or includes a certain percent amino acid sequence identity to, with, or against a given reference sequence) is calculated as follows:

100×(fraction of NB)

where A is the number of amino acid residues scored as identical in the alignment of the candidate sequence and the reference sequence, and where Bis the total number of amino acid residues in the reference sequence. In some embodiments where the length of the candidate sequence does not equal to the length of the reference sequence, the percent amino acid sequence identity of the candidate sequence to the reference sequence would not equal to the percent amino acid sequence identity of the reference sequence to the candidate sequence.

Two polynucleotide or polypeptide sequences are said to be "identical" if the sequence of nucleotides or amino acids in the two sequences is the same when aligned for maximum correspondence as described above. Comparisons between two sequences are typically performed by comparing the sequences over a comparison window to identify and compare local regions of sequence similarity. A "comparison window" as used herein, refers to a segment of at least about 5 contiguous positions, about 10 contiguous positions, about 15 contiguous positions, or more, in which a sequence may be compared to a reference sequence of the same number of contiguous positions after the two sequences are optimally aligned.

As used herein, the term "pharmaceutically acceptable carrier" refers to an excipient or diluent in a pharmaceutical composition. The pharmaceutically acceptable carrier is compatible with the other ingredients of the formulation and not deleterious to the recipient. The pharmaceutically acceptable carrier may provide pharmaceutical stability to the composition (e.g., stability to an AVP), or may impart another beneficial characteristic (e.g., sustained release characteristics). The nature of the carrier may differ with the mode of administration. For example, for intravenous administration, an aqueous solution carrier is generally used; for oral administration, a solid carrier may be preferred.

As used herein, the term "pharmaceutical composition" refers to a medicinal or pharmaceutical formulation that contains an active ingredient at a pharmaceutically acceptable purity as well as one or more excipients and diluents that render the active ingredient suitable for the method of administration. The pharmaceutical composition includes pharmaceutically acceptable components that are compatible with, for example, an AVP described herein. The pharmaceutical composition may be in aqueous form, for example, for intravenous or subcutaneous administration, in tablet or capsule form, for example, for oral administration, or in cream for, for example, for topical administration.

As used herein, the term "polar amino acid" refers to an amino acid having a chemical polarity in its side chain induced by atoms with different electronegativity. The polarity of a polar amino acid is dependent on the electronegativity between atoms in the side chain of the amino acid and the asymmetry of the structure of the side chain. Polar amino acids are serine, threonine, cysteine, histidine, methionine, tyrosine, tryptophan, asparagine, and glutamine.

As used herein, the term "subject" refers to a mammal, e.g., a human or other non-human mammal, such as a non-human primate, bovine, equine, canine, ovine, or feline.

The term "sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebra-spinal fluid, saliva, sputum, tears, perspiration, mucus, tumor lysates, tissue culture medium, tissue extracts such as homogenized tissue, tumor tissue, cellular extracts, and combinations thereof.

As used herein, the term "therapeutically effective amount" refers to an amount, e.g., a pharmaceutical dose, of a composition described herein (e.g., a composition containing an AVP (such as a polypeptide with at least 75% (e.g., at least 80%, 85%, 90%, 95%, 97%, or 100%) sequence identity to the sequence of any one of SEQ ID NOs: 1-47 and 54-59, such as, e.g., a polypeptide with at least 75% (e.g., at least 80%, 85%, 90%, 95%, 97%, or 100%) sequence identity to the sequence of any one of SEQ ID NOs: 1-28, in particular, the AVPs of SEQ ID NOs: 1-28, e.g., the AVP of SEQ ID NO: 15 or 21) or a nucleic acid based composition (e.g., a nucleic acid having a nucleotide sequence encoding an AVP, such as a nucleic acid encoding a peptide of any one of SEQ ID NOs: 1-47 or 54-59, such as the AVPs of SEQ ID NOs: 1-28, e.g., the AVP of SEQ ID NO: 15 or 21)), effective in inducing a desired biological effect in a subject or in treating a subject with a medical condition or disorder described herein (e.g., a viral infection). A therapeutically effective amount may be an amount sufficient to exhibit antiviral activity against one or more viruses. A therapeutically effective amount may be determined using assays known in the art, such as a cytopathic effect (CPE) inhibition assay, plaque assay, or a serum virus neutralization assay). It is also to be understood herein that a "therapeutically effective amount" may be interpreted as an amount giving a desired therapeutic effect, either taken in one dose or in any dosage or route, taken alone or in combination with other therapeutic agents.

As used herein, the terms "treatment" or "treating" refer to reducing or ameliorating a medical condition (e.g., a disease or disorder mediated or caused by a virus (e.g., pneumonia) and/or symptoms associated therewith (e.g., symptoms from a viral infection). It will be appreciated that, although not precluded, treating a medical condition does not require that the disorder or symptoms associated therewith be completely eliminated. Reducing or decreasing the side effects of a medical condition, such as a viral infection, or the risk or progression of the medical condition, may be relative to a subject who did not receive treatment, e.g., a control, a baseline, or a known control level or measurement. The reduction or decrease may be, e.g., by about 1%, 2%, 3%, 4%, 5%, 6%, 7%, 8%, 9%, 10%, 20%, 30%, 40%, 50%, 60%, 70%, 80%, 90%, 95%, 97%, 99%, or about 100% relative to the subject who did not receive treatment or the control, baseline, or known control level or measurement, or may be a reduction in the number of days during which the subject experiences the medical condition or associated symptoms (e.g., a reduction of 1-30 days, 2-12 months, 2-5 years, or 6-12 years).

Wherever any of the phrases "for example," "such as," "including" and the like are used herein, the phrase "and without limitation" is understood to follow unless explicitly stated otherwise. Similarly, "an example," "exemplary" and the like are understood to be non-limiting.

The term "substantially" used herein allows for deviations from the descriptor that do not negatively impact the intended purpose. Descriptive terms may be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function.

BRIEF DESCRIPTION OF THE DRAWINGS

FIGS. 2A and 2B are graphs showing virus inhibition and cell viability data for TL1, TL2, and TAS. FIGS. 2C and 2D are graphs showing virus inhibition and cell viability data for R2, R5, N1, N2, W1, and W2. FIGS. 2E and 2F are graphs showing virus inhibition and cell viability data for HF3, HF4, and AHR. FIGS. 2G and 2H are graphs showing virus inhibition and cell viability data for MFR, MFG, MFW, and IT1b. FIGS. 21 and 2J are graphs showing virus inhibition and cell viability data for TL4, TL4N, TL4dG, and TL4NdG. FIGS. 2K and 2L are graphs showing virus inhibition and cell viability data for TL4FRL, TL4ARL, TL4FRW, and TL3FL.

FIG. 21A is a graph showing envelope circularity measurements of peptide-treated virions from analysis of the cryo-electron microscopy dataset shown in FIG. 20. Envelopes of peptide-treated virions were traced, and the circularity of the envelopes were measured using ImageJ. Data are represented by box plots (left of x-axis tick) as well as individual measurements (right of x-axis tick). Significance was determined by one-way ANOVA with Turkey's post test. *, $p<0.001$. n=103-115.

FIG. 22 is a pair of representative cryo-electron microscopy images showing virions briefly incubated with NATT peptide. UV-inactivated H1N1 was incubated with 25 UM NATT peptide for 1 and 5 minutes then immediately frozen in liquid ethane. Samples were visualized by cryo-electron microscopy. Insets show additional images of the same sample.

FIG. 23 is a table showing the attributes of the gain-of-function AVPs (SEQ ID NOs: 2-28) and the IT1b peptide. Activities of the AVPs in FIG. 23 are provided which include $EC_{50}$ (50% effective concentration) values, which were calculated from nonlinear curve fits of virus inhibition plots in FIGS. 2A-2L. $CC_{50}$ (50% cytotoxic concentration) values were calculated from cytotoxicity plots in FIGS. 2A-2L using linear curve fits calculated from the values immediately above and below 50% cytotoxicity. The therapeutic index ("Index") for each AVP was calculated by dividing the $CC_{50}$ by the $EC_{50}$. Shaded cells represent values that were either lower in $EC_{50}$ or higher in $CC_{50}$ or Index when compared to IT1b. Percentages at the bottom of FIG. 23 represent the percentage of shaded cells in that column, excluding IT1b and valueless cells.

DETAILED DESCRIPTION

Figures 1A, 1B:
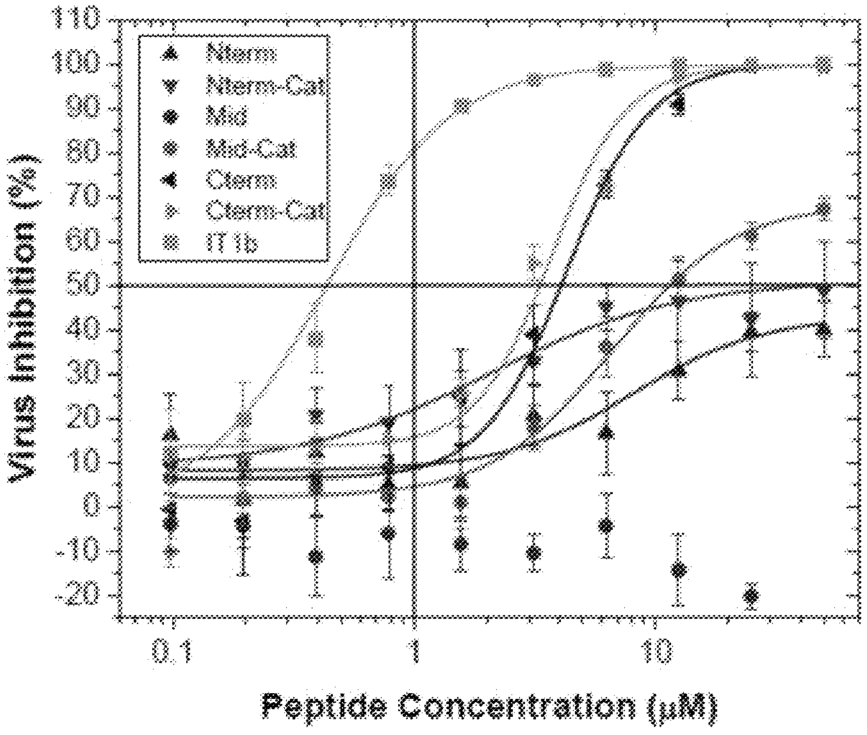
FIG. 1A is a schematic depicting the IT1b peptide (SEQ ID NO: 42) segmented into six small peptides. Peptides representing the N-terminus (Nterm; SEQ ID NO: 54), middle (Mid; SEQ ID NO: 56), and C-terminus (Cterm; SEQ ID NO: 58) were synthesized along with cationic versions of each segment (Nterm-Cat (SEQ ID NO: 55), Mid-Cat (SEQ ID NO: 57), Cterm-Cat (SEQ ID NO: 59)).
FIG. 1B is a graph showing the percentage of virus inhibition after LASVpv was treated with serial dilutions of the peptides shown in FIG. 1A for 1 hour, then added to HEK cells. Infectivity was quantified by measuring luciferase expression translated from the LASVpv genome approximately 72 hours of incubation with the HEK cells. Inhibition measurements were fit to nonlinear curves which are shown here as solid lines (n=4, mean±SE).
Figure 1C:
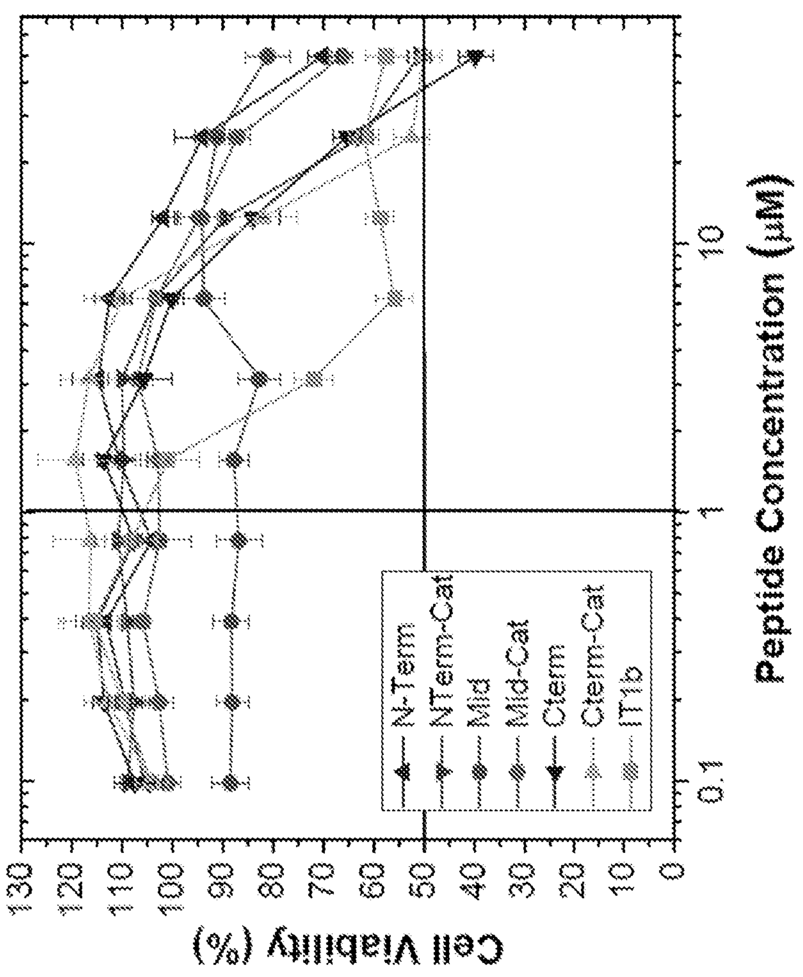
FIG. 1C is a graph showing the percentage of cell viability after serial dilutions of the peptides shown in FIG. 1A were added to HEK cells. Cell viability was determined using CELLTITER-GLOR approximately 72 hours after treatment (n=8, mean±SE).

Described herein are antiviral peptides (AVPs) capable of treating, inhibiting, or reducing one or more symptoms of a viral infection. The AVPs exhibit the ability to disrupt the infectivity of multiple viral pathogens with reduced cytotoxicity (e.g., to eukaryotic cells) and improved hemocompatibility (e.g., activity in the presence of human serum or a human serum component). The AVPs disclosed here retain activity against a wide range of viral pathogens, in particular both enveloped and non-enveloped viruses. The antiviral activity of the AVPs is also retained in the presence of serum. Further, the AVPs exhibit reduced cytotoxicity to eukaryotic cells.

The AVPs described herein were rationally designed to be active against viral pathogens even in the presence of eukaryotic cells and to have a specificity for viral pathogens over eukaryotic cells. Without being limited to a particular mechanism of action, the AVPs appear to demonstrate rapid antiviral activity by inhibiting the ability of viruses to fuse with target cells, thereby limiting their infectivity.

Antiviral Peptides

Featured are broad-spectrum antiviral peptides (AVPs) capable of disrupting the infectivity of multiple viral pathogens. The AVPs also exhibit reduced cytotoxicity against eukaryotic cells and robust hemocompatibility (e.g., the AVPs do not exhibit diminished antiviral activity in the presence of serum (e.g., human serum or a human serum component)).

AVPs described herein include those represented by the consensus sequences of SEQ ID NO: 1 and 29. For example, an AVP described herein has at least 75% or more (e.g., 80%, 85%, 90%, 95%, 97%, 98%, 99%, or 100%) sequence identity to one or more of the sequences listed in Table 1 (e.g., SEQ ID NOs: 2-28) or a fragment thereof (e.g., a fragment of at least 5, 7, 10 or more consecutive amino acids in length), in particular, the AVP has the sequence of SEQ ID NO: 15 or 21.

TABLE 1

List of AVP Sequences

| SEQ ID NO | Description | Sequence |
|---|---|---|
| 1 | Consensus | $RRX_1X_2$-$L_m$-$(X_3L_m)_n$-$X_4X_5RR$ |
| 2 | TL3 | RRGWLLLRLLLWGRR |
| 3 | D-TL3 | rrgwlllrlllwgrr (All D) |
| 4 | TL1 | RRGWLRLWGRR |
| 5 | TL2 | RRGWLLRLLWGRR |
| 6 | TAS | RRGWLLLRLWGRR |
| 7 | R2 | RRGWLLRLLRLLWGRR |
| 8 | R5 | RRGWLRLRLRLRLRLWGRR |
| 9 | N1 | RRGWLLLNLLLWGRR |

TABLE 1-continued

List of AVP Sequences

| SEQ ID NO | Description | Sequence |
|---|---|---|
| 10 | N2 | RRGWLLNLLNLLWGRR |
| 11 | W1 | RRGWLLLWLLLWGRR |
| 12 | W2 | RRGWLLWLLWLLWGRR |
| 13 | HF3 | RRGWLLLRLLLRLLLWGRR |
| 14 | HF4 | RRGWLLLRLLLRLLLRLLLWGRR |
| 15 | AHR | RRGWLLLRLLRLLLRLLWGRR |
| 16 | D-AHR | rrgwlllrllrlllrllwgrr (All D) |
| 17 | MFR | RRGWLLLRLLLRGGGGRLLLRLLLWGRR |
| 18 | MFG | RRGWLLLRLLLGGGGLLLRLLLWGRR |
| 19 | MFW | RRGWLLLRLLLWGGGGWLLLRLLLWGRR |
| 20 | TL4 | RRGWLLLLRLLLLWGRR |
| 21 | TL4N | RRGWLLLLNLLLLWGRR |
| 22 | TL4dG | RRWLLLLRLLLLWRR |
| 23 | TL4NdG | RRWLLLLNLLLLWRR |
| 24 | D-TL4NdG | rrwllllnllllwrr (All D) |
| 25 | TL4FRL | RRWLLFLRLFLLWRR |
| 26 | TL4ARL | RRWLLALRLALLWRR |
| 27 | TL4FRW | RRWLLLLRLLLLFRR |
| 28 | TL3FL | RRWLLLGRLLLWRR |

$X_1$ is G, any amino acid, or is absent; $X_2$ is W, Y, or F; $X_3$ is K, R, D, E, S, T, N, Q, C, G, or P; $X_4$ is W, Y, or F; $X_5$ is G or any amino acid; m = 1-6; n = 1-3.

The featured AVPs of Table 1, and variants thereof with at least 75% or more sequence identity thereto, can have from about 6 to about 34 amino acids (e.g., from about 6 amino acids to about 32 amino acids, from about 6 amino acids to about 28 amino acids, from about 6 amino acids to about 24 amino acids, from about 6 amino acids to about 20 amino acids, from about 6 amino acids to about 16 amino acids, from about 6 amino acids to about 12 amino acids, from about 12 amino acids to about 32 amino acids, from about 12 amino acids to about 28 amino acids, from about 12 amino acids to about 24 amino acids, from about 12 amino acids to about 20 amino acids, from about 12 amino acids to about 16 amino acids, from about 18 amino acids to about 32 amino acids, from about 18 amino acids to about 28 amino acids, from about 18 amino acids to about 24 amino acids, from about 24 amino acids to about 34 amino acids, or from about 24 amino acids to about 30 amino acids).

In particular, AVPs described herein, which can be represented by the consensus sequence of SEQ ID NO: 1 (see Table 1) or a fragment thereof (e.g., a fragment of at least 5, 7, 10 or more consecutive amino acids in length), can contain two arginine (R) residues at the amino and carboxy terminal ends of the AVP (e.g., the AVP begins with two consecutive RR and/or ends with two consecutive RR). The AVPs also have a hydrophobic core containing a leucine (L) residue (e.g., 1 to 6 leucine residues), which may be located at a residue position that is about five amino acids from the N-terminal end of the AVP. The hydrophobic core of the AVPs may include multiple $X_3L_m$ motifs (e.g., one, two, or three motifs; see Table 1, consensus sequence of SEQ ID NO: 1) in which L is leucine and $X_3$ is a variable residue that includes charged, polar, and structure-modifying amino acids (e.g., lysine, arginine, aspartate, glutamate, serine, threonine, asparagine, glutamine, cysteine, glycine, or praline) that may be located within 5-10 amino acids (e.g., five, six, seven, eight, nine, or ten amino acids) from the N-terminal end of the AVP.

AVPs described herein can have at least 75% or more (e.g., 85%, 90%, 95%, 97%, 98%, 99%, or 100%) sequence identity to one or more of the sequences listed in Table 1 (e.g., SEQ ID NOs: 1-28) or a fragment thereof (e.g., a fragment of at least 5, 7, 10 or more consecutive amino acids in length).

AVPs described herein can also be represented by the consensus sequence of SEQ ID NO: 29. For example, an AVP described herein can have at least 75% or more (e.g., 80%, 85%, 90%, 95%, 97%, 98%, 99%, or 100%) sequence identity to one or more of the sequences listed in Table 2 (e.g., SEQ ID NOs: 30-47 or 54-59) or a fragment thereof (e.g., a fragment of at least 5, 7, 10 or more consecutive amino acids in length). In particular, the AVP has the sequence of SEQ ID NO: 31 or 32.

TABLE 2

List of Additional AVP Sequences

| SEQ ID NO | Description | Sequence |
|---|---|---|
| 29 | Consensus | $X_1X_2X_3WX_4LX_5LX_6LX_7YX_8X_9X_{10}$ |
| 30 | *VDVY* | RRGWVLDLVLYYGRR |
| 31 | *ARVA | RRGWALRLVLAY |
| 32 | *arva | rrgwalrlvlay (All D) |
| 33 | ARYV | WALRLYLGVY |
| 34 | VVRG | WVLVLRLGY |
| 35 | *NRRV* | RRGWNLRLRLVYGRR |
| 36 | *ARNY* | RRGWALRLNLYYGRR |
| 37 | *GRVY* | RRGWGLRLVLYYGRR |
| 38 | *RNNY* | RRGWRLNLNLYYGRR |
| 39 | *TNTN* | RRGWTLNLTLNYGRR |
| 40 | *NATT* | RRGWNLALTLTYGRR |
| 41 | IT1-a | RRGFSLKLLLSYRGWALLRLGYGRR |
| 42 | IT1-b | RRGFSLKLALLKDGWLLLRLGYGRR |
| 43 | D-IT1-b | rrgfslklallkdgwlllrlgygrr (All D) |
| 44 | IT1-C | RRGFSLKLALLYRGWLLLLRLGYGRR |
| 45 | IT1-d | RRGFSLKLRLLYRGWGLALRLGYGRR |
| 46 | IT1-e | RRGFSLKLKLLYRGWALALRLGYGRR |
| 47 | IT1-f | RRGFSLKLALLKDGWLLLLRLGYGRR |
| 54 | Nterm | RRGFSLKLALL |

TABLE 2-continued

List of Additional AVP Sequences

| SEQ ID NO | Description | Sequence |
|---|---|---|
| 55 | Nterm-Cat | RRGFSLKLALLK |
| 56 | Mid | LALLKDGWLLL |
| 57 | Mid-Cat | KLALLKDGWLLLR |
| 58 | Cterm | WLLLRLGYGRR |
| 59 | Cterm-Cat | KDGWLLLRLGYGRR |

$X_1$, $X_2$, $X_9$, and $X_{10}$ are each, independently, R or absent; $X_3$ and $X_8$ are each, independently, G or absent; $X_4$ is V, A, N, G, R, or T; $X_5$ is D, R, V, N, or A; $X_6$ is V, Y, R, N, or T; $X_7$ is Y, A, G, V, N, or T.

The featured AVPs of Table 2, and variants thereof with at least 75% or more sequence identity thereto, can have from about 6 to about 30 amino acids (e.g., from about 6 amino acids to about 28 amino acids, from about 6 amino acids to about 24 amino acids, from about 6 amino acids to about 20 amino acids, from about 6 amino acids to about 16 amino acids, from about 6 amino acids to about 12 amino acids, from about 6 amino acids to about 10 amino acids, from about 12 amino acids to about 28 amino acids, from about 12 amino acids to about 24 amino acids, from about 12 amino acids to about 20 amino acids, from about 12 amino acids to about 16 amino acids, from about 18 amino acids to about 28 amino acids, from about 18 amino acids to about 24 amino acids, from about 18 amino acids to about 22 amino acids, or from about 24 amino acids to about 28 amino acids).

AVPs described herein, which can be represented by the consensus sequence of SEQ ID NO: 29 (see Table 2) or a fragment thereof (e.g., a fragment of at least 5, 7, 10 or more consecutive amino acids in length) can contain two arginine (R) residues at the amino and carboxy terminal ends of the AVP (e.g., the AVP begins with two consecutive RR and/or ends with two consecutive RR). The AVPs also have a $X_4LX_5LX_6LX_7$ motif (wherein L is leucine, $X_4$ is a variable residue that includes V, A, N, G, R, T, or a variant thereof, $X_5$ is a variable residue that includes D, R, V, N, A, or a variant thereof, $X_6$ is a variable residue that includes V, Y, R, N, T, or a variant thereof, $X_7$ is a variable residue that includes Y, A, G, V, N, T, or a variant thereof) that may be located within about five amino acids from the C-terminal end of the AVP.

AVPs described herein can have at least 75% or more (e.g., 85%, 90%, 95%, 97%, 98%, 99%, or 100%) sequence identity to one or more of the sequences listed in Table 2 (e.g., SEQ ID NOs: 29-47 or 54-59) or a fragment thereof (e.g., a fragment of at least 5, 7, 10 or more consecutive amino acids in length).

The AVPs described herein may be substantially hydrophobic. Furthermore, the AVPs may be substantially cationic, anionic, polar, and/or hydrophobic. The AVPs may possess antiviral properties against a broad spectrum of viruses (e.g., enveloped and non-enveloped viruses).

The AVPs may be manufactured as a secreted peptide (e.g., for expression in a cell as a proprotein with a cleavable signal peptide).

The AVPs described herein may be capable of treating, inhibiting, or reducing an infection by a virus (e.g., a viral infection caused by an enveloped virus). The virus may be a DNA or RNA virus, a reverse-transcribed virus, an enveloped virus, or a non-enveloped virus. For example, the virus may belong to a family selected from the group consisting of Adenoviridae, Arenaviridae, Coronaviridae, Filoviridae, Flaviviridae, Hepadnaviridae, Herpesviridae, Metapneumovirus, Orthomyxoviridae, Orthopneumovirus, Paramyxoviridae, Retroviridae, and Togaviridae.

The AVPs described herein (e.g., a polypeptide with at least 75% or more (e.g., 85%, 90%, 95%, 97%, 98%, 99%, or 100%) sequence identity to one or more of the sequences listed in Tables 1 and 2) may be capable of treating, inhibiting, or reducing an infection by a viral pathogen (e.g., adenoviruses (e.g., human adenovirus type 1 (HAdV-1), HAdV-2, HAdV-3, HAdV-4, HAdV-5, HAdV-6, HAdV-7)), MERS-CoV, SARS-CoV, SARS-CoV-2 or variants thereof, dengue viruses (e.g., DENV-1, DENV-2, DENV-3, DENV-4, DENV-5), ebolaviruses (e.g., Ebola virus (Zaire ebolavirus sp.), Sudan virus (Sudan ebolavirus sp.), Tar Forest virus (Tal Forest ebolavirus sp., formerly Cote d'Ivoire ebolavirus), Bundibugyo virus (Bundibugyo ebolavirus sp.), Reston virus (Reston ebolavirus sp.)), Marburg virus (e.g., Marburg Marburgvirus sp. (e.g., Marburg virus (MARV) and Ravn virus (RAVV))), human immunodeficiency viruses (e.g., HIV-1 and HIV-2), hepatitis B virus, hepatitis C virus, hepatitis D virus, herpesviruses (e.g., herpes simplex virus type 1 (HSV-1), herpes simplex virus type 2 (HSV-2), cytomegalovirus (e.g., human cytomegalovirus (HCMV)), Epstein-Barr virus (EBV), human herpesvirus 6 (e.g., HHV-6A and HHV-6B), human herpesvirus 7 (HHV-7), Kaposi's sarcoma-associated herpesvirus (KSHV; also known as human herpesvirus 8 (HHV-8)), varicella-zoster virus (VZV)), influenza A virus (e.g., subtypes H1N1, H3N2, H5N1), influenza B virus (e.g., B/Yamagata and BNictoria), influenza C virus, influenza D virus, Lassa virus, respiratory syncytial virus (RSV), human metapneumovirus (hMPV), parainfluenza viruses (e.g., human parainfluenza virus type 1 (HPIV-1), HPIV-2, HPIV-3, HPIV-4), measles virus (MV), West Nile virus (WNV), yellow fever virus, Zika virus (ZIKV), chikungunya virus (CHIKV), Nipah virus (NIV), Hendra virus (HeV), feline immunodeficiency virus (FIV), feline leukemia virus (FeLV), canine distemper virus (CDV), canine parvovirus (CPV), bovine viral diarrhea (BVD) virus, and bovine leukemia virus (BLV)). For example, the AVPs described herein (e.g., an AVP of any one or more of SEQ ID NOs: 1-47 or 54-59, and variants thereof with up to 75% sequence identity or more thereto, such as the AVPs of SEQ ID NOS: 1-28, e.g., the AVP of SEQ ID NO: 15 or 21) may be capable of reducing an amount of an infective viral pathogen by between about 1% and about 100% (e.g., 1%, 5%, 10%, 20%, 30%, 40%, 50%, 60%, 70%, 80%, 90%, 95%, 99%, or 100%), such as by causing aggregation of the virions, thereby inhibiting or reducing infection of a target cell, such as a target cell in a subject (e.g., a human). The reduction may be determined in a sample containing the pathogen (e.g., a blood or tissue sample). Alternatively, a physician or veterinarian may monitor the responsiveness of a subject (e.g., a human or other mammal, such as a non-human primate, bovine, equine, canine, ovine, or feline) to treatment (e.g., systemic treatment) with an AVP described herein (e.g., one or more of the peptides of SEQ ID NOs: 1-47 or 54-59, such as the AVPs of SEQ ID NOs: 1-28, e.g., the AVP of SEQ ID NO: 15 or 21) using established procedures. The responsiveness of the infecting viral pathogen to the AVPs described herein may be monitored in vitro, wherein a sample of the pathogen is taken and grown in a laboratory setting in various concentrations of the AVP. Inhibition of viral infection, and the observations of the subject by a physician or veterinarian skilled in the art, can be used to indicate the responsiveness of the virus to the AVP.

In some instances, administration of an effective amount of an AVP reduces the course of viral infection by about 1, 2, 3, 4, 5, 6, 7 days; 1, 2, 3, 4, weeks; 1, 2, 3, 4, 5, 6, 7, 8, 9, 10, 11, or 12 months; or 1 year or more. In some instances, administration of an effective amount of an AVP results in a reduced and/or undetectable serum viral load that may be maintained for at least about 1, 2, 3, 4, 5, 6, 7 days; 1, 2, 3, 4, weeks; 1, 2, 3, 4, 5, 6, 7, 8, 9, 10, 11, or 12 months; or 1 year or more.

In some instances, efficacy of treatment can be determined by monitoring a change in the serum viral load from a sample from the subject obtained prior to and after administration of an effective amount of an AVP (e.g., one or more of the peptides of SEQ ID NOs: 1-47 or 54-59, such as the AVPs of SEQ ID NOs: 1-28, e.g., the AVP of SEQ ID NO: 15 or 21). A reduction in serum viral load of at least about 5%, 10%, 20%, 30%, 40%, 50%, 60%, 70%, 80%, 90%, or more compared to viral load determined from the subject prior to administration of an effective amount of the AVP may indicate that the subject is receiving benefit from the treatment. If a viral load does not decrease by at least about 10%, 20%, 30%, or more after administration of a composition, the dosage of the composition to be administered may be increased.

Also featured are AVPs or variants thereof having substantially the same effect as the AVPs described herein. Such AVPs include, but are not limited to, a substitution, addition, or deletion mutant of the AVPs described herein (e.g., in which one, two, or three amino acids of the AVPs (e.g., the AVPs of SEQ ID NOs: 1-47 or 54-59, such as the AVPs of SEQ ID NOs: 1-28) are substituted with another amino acid, are deleted, or in which one or more amino acids (e.g., 1-10 amino acids) are added to an AVP). Also encompassed are peptides that have amino acid sequences that are substantially identical to the amino acid sequences of the AVPs described herein. A variety of sequence alignment software programs are available in the art to facilitate determination of sequence identity or equivalence of any protein to a protein of the invention. Non-limiting examples of these programs are BLAST family programs including BLASTN, BLASTP, BLASTX, TBLASTN, and TBLASTX (BLAST is available from the worldwide web at ncbi.nlm.nih.gov/BLAST/), FastA, Compare, DotPlot, BestFit, GAP, FrameAlign, ClustalW, and PileUp. Other similar analysis and alignment programs can be purchased from various providers, such as DNA Star's MegAlign, or the alignment programs in GeneJockey. Alternatively, sequence analysis and alignment programs can be accessed through the World Wide Web at sites such as the CMS Molecular Biology Resource at sdsc.edufResTools/cmshp.html and ExPASy Proteomics Server at expasy.org/. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

The AVPs described herein may contain one or more D-amino acids instead of or in addition to L-amino acids. Glycine does not have chirality due to two hydrogens. However, all other amino acids may be D-amino acids, including D-ALA, D-ARG, D-ASN, D-ASP, D-CYS, D-GLN, D-GLU, D-HIS, D-ILE, D-LEU, D-LYS, D-MET, D-PHE, D-PRO, D-SER, D-THR, D-TRP, D-TYR, AND D-VAL. In particular, one or more or all of the amino acids of the AVPs may be substituted with a D-amino acid.

Alternatively, the AVPs described herein may contain all L-amino acids. In some AVPs described herein, L-amino acids may be used at certain positions and D-amino acids may be used at other specified positions.

The AVPs disclosed herein are a group of AVPs that exhibit the ability to disrupt infectivity of viral pathogens (e.g., enveloped viral pathogens, such as Lassa virus, influenza virus, and SARS-CoV-2) in the presence of serum or a serum component. The AVPs exhibit potent broad-spectrum antiviral activity against a wide range of viruses, as well as low cytotoxicity against mammalian cells, such as kidney cells.

Polynucleotides

Also featured are polynucleotides that encode the polypeptides described herein (e.g., polypeptides with 75% (e.g., 80%, 85%, 90%, 95%, 97%, 99%, or 100%) sequence identity to one or more of the polypeptides listed in Table 1 (e.g., polypeptides of SEQ ID NOs: 1-28, such as a peptide of SEQ ID NO: 15 or 21) or Table 2 (e.g., polypeptides of SEQ ID NOs: 29-47 or 54-59, such as a peptide of SEQ ID NO: 31 or 32)). The term polynucleotide is used broadly and refers to polymeric nucleotides of any length. By way of example and not limitation, the polynucleotides of the invention may have a sequence encoding all or part of an AVP (e.g., the peptides of Table 1 and 2, and peptides with at least 75% sequence identity thereto (e.g., over at least 5, 10, or more amino acids (e.g., over the entire amino acid sequence))). The polynucleotide described herein may be, for example, linear, circular, supercoiled, single-stranded, double-stranded, branched, partially double-stranded or partially single-stranded. The nucleotides of the polynucleotide may be naturally occurring nucleotides or modified nucleotides.

Polynucleotides described herein encode AVPs that maintain activity against viral pathogens (e.g., enveloped or non-enveloped viruses) in the presence of eukaryotic cells and exhibit reduced cytotoxicity against eukaryotic cells and improved hemocompatibility (e.g., in the presence of human serum or a human serum component).

Polynucleotide sequences that encode peptide variants within 75% sequence identity to any one of SEQ ID NOs: 1-47 or 54-59, such as the AVPs of SEQ ID NOs: 1-28, and exhibiting the characteristics of AVPs described herein, may also be identified by methods known in the art. A variety of sequence alignment software programs are available to facilitate determination of homology or equivalence. Non-limiting examples of these programs are BLAST family programs including BLASTN, BLASTP, BLASTX, TBLASTN, and TBLASTX (BLAST is available from the worldwide web at ncbi.nlm.nih.gov/BLAST/), FastA, Compare, DotPlot, BestFit, GAP, FrameAlign, ClustalW, and PileUp. Other similar analysis and alignment programs can be purchased from various providers, such as DNA Star's MegAlign, or the alignment programs in GeneJockey. Alternatively, sequence analysis and alignment programs can be accessed through the World Wide Web at sites such as the CMS Molecular Biology Resource at sdsc.edufResTools/cmshp.html and ExPASy Proteomics Server at expasy.org/. Any sequence database that contains DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS.

Parameters for determining the extent of homology set forth by one or more of the aforementioned alignment programs are well established in the art. They include but are not limited to p value, percent sequence identity and the percent sequence similarity. P value is the probability that the alignment is produced by chance. For a single alignment, the p value can be calculated according to Karlin et al., *Proc. Natl. Acad. Sci.* (*USA*) 87:2246, 1990. For multiple alignments, the p value can be calculated using a heuristic approach such as the one programmed in BLAST. Percent sequence identity is defined by the ratio of the number of nucleotide or amino acid matches between the query sequence and the known sequence when the two are optimally aligned. The percent sequence similarity is calculated in the same way as percent identity except one scores amino acids that are different but similar as positive when calculating the percent similarity. Thus, conservative changes that occur frequently without altering function, such as a change from one basic amino acid to another or a change from one hydrophobic amino acid to another are scored as if they were identical.

Expression Vectors

Also featured are expression vectors containing at least one polynucleotide encoding a peptide of the invention or a fragment thereof (e.g., a fragment of an AVP that retains activity against pathogens (e.g., in the presence of eukaryotic cells, such as red blood cells). For example, an expression vector includes a polynucleotide encoding one or more of the peptides of Table 1 and 2 and variants thereof having at least 75% sequence identity thereto. Expression vectors are well known in the art and include, but are not limited to, viral vectors and plasmids. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127), adenovirus vectors, alphavirus-based vectors (e.g., Sindbis virus vectors, Semliki forest virus), Ross River virus, adeno-associated virus (AAV) vectors (see, e.g., PCT Publication Nos. WO 94/12649, WO 93/03769; WO 93/19191; WO 94/28938; WO 95/11984 and WO 95/00655), vaccinia virus (e.g., Modified Vaccinia virus Ankara (MVA) or fowlpox), Baculovirus recombinant system, and herpes virus.

Nonviral vectors, such as plasmids, are also well known in the art and include, but are not limited to prokaryotic and eukaryotic vectors (e.g., yeast- and bacteria-based plasmids), as well as plasmids for expression in mammalian cells. Methods of introducing the vectors into a host cell and isolating and purifying the expressed protein are also well known in the art (e.g., *Molecular Cloning: A Laboratory Manual*, second edition, Sambrook, et al., 1989, Cold Spring Harbor Press). Examples of host cells include, but are not limited to, mammalian cells, such as NSO, CHO cells, HEK and COS, and bacterial cells, such as *E. coli.*

By way of example, a vector containing a polynucleotide encoding an AVP described herein may further contain a tag polynucleotide sequence to facilitate protein isolation and/or purification. Examples of tags include but are not limited to the myc-epitope, S-tag, his-tag, HSV epitope, V5-epitope, FLAG and CBP (calmodulin binding protein). Such tags are commercially available or readily made by methods known to the art.

The vector may further include a polynucleotide sequence encoding a linker sequence. Generally, the linking sequence is positioned in the vector between the AVP-encoding polynucleotide sequence and the polynucleotide tag sequence (e.g., a purification tag sequence). Linking sequences can encode random amino acids or could contain functional sites. Examples of linking sequences containing functional sites include, but are not limited to, sequences containing the Factor Xa cleavage site, the thrombin cleavage site, and the enterokinase cleavage site.

By way of example, and not limitation, an AVP may be generated as described herein using a mammalian expression vector in a mammalian cell culture system or a bacterial expression vector in a bacterial culture system. Primers may be used to amplify the desired sequence from a template.

Methods of Manufacture

The AVPs described herein can be prepared by chemical peptide synthesis, such as by coupling different amino acids to each other through chemical conjugation. Chemical peptide synthesis is particularly suitable for the inclusion of, e.g., D-amino acids, amino acids with non-naturally occurring side chains, and natural amino acids with modified side chains, such as methylated cysteine. Chemical peptide synthesis methods are well known in the art. Peptide synthesis can be performed as solid phase peptide synthesis (SPPS) or contrary to solution phase peptide synthesis. The best known SPPS methods are tBoc and Fmoc solid phase chemistry which is amply known to the skilled person. In addition, peptides can be linked to one other to form longer peptides using a ligation strategy (chemo selective coupling of two unprotected peptide fragments) as originally described by Kent (Schnolzer & Kent (1992) *Int. J. Pept. Protein Res.* 40, 190-193) and reviewed, for example, in Tam et al. (2001) *Biopolymers* 60, 194-205. This provides the potential to achieve protein synthesis beyond the scope of SPPS. Many proteins with the size of 100-300 residues have been synthesized successfully by this method. Synthetic peptides have continued to play an ever increasing role in the research fields of biochemistry, pharmacology, neurobiology, enzymology, and molecular biology because of the advances in SPPS.

For recombinant production, one or more polynucleotides encoding the AVP, or a fragment or variant thereof, can be inserted into one or more vectors for further cloning and/or expression in a host cell. Such polynucleotides may be readily isolated and sequenced using conventional procedures. For expression, a vector (e.g., an expression vector) containing one or more of the polynucleotides of the invention is provided. Methods which are well known to those skilled in the art can be used to construct expression vectors containing the coding sequence of the AVP, or a fragment or variant thereof, along with appropriate transcriptional/translational control signals. These methods include in vitro recombinant DNA techniques and synthetic techniques. See, for example, the techniques described in Maniatis et al., *Molecular Cloning: A Laboratory Manual*, Cold Spring Harbor Laboratory, N.Y. (1989); and Ausubel et al., Current Protocols in Molecular Biology, Greene Publishing Associates and Wiley Interscience, N.Y. (1989). The expression vector can be part of a plasmid, virus, or can be a nucleic acid fragment. The expression vector includes an expression cassette into which the polynucleotide encoding the AVP, or a fragment thereof, (e.g., the coding region) is cloned into operable association with a promoter and or other transcription control elements. Two or more coding regions can be present in a single polynucleotide construct, e.g., on a single vector, or in separate polynucleotide constructs, e.g., on separate (different) vectors. Furthermore, any vector may contain a single coding region, or can have two or more coding regions, e.g., a vector described herein can encode one or more polypeptides, which are post- or co-translationally separated into the final polypeptide via proteolytic cleavage. In addition, a vector, polynucleotide, or nucleic acid described herein can contain heterologous coding regions, either fused or unfused to a polynucleotide encoding the AVP, or any fragment or variant thereof. Heterologous coding regions include, for example, specialized elements or motifs, such as a secretory signal peptide or heterologous functional domain. An operable association is when a coding region for a gene product, (e.g., a polypeptide), is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that polynucleic acid. The promoter may be a cell-specific promoter that directs substantial transcription of the DNA only in predetermined cells. Other transcription control elements, besides a promoter, for example, are enhancers, operators, repressors, and transcription termination signals, can be operably associated with the polynucleotide to direct cell-specific transcription. A variety of transcription control regions are known to those skilled in the art. Examples of transcription control regions, which function in vertebrate cells, such as, but not limited to, promoter enhancer segments from cytomegaloviruses (e.g., the immediate early promoter, in conjunction with intron-A), simian virus 40 (e.g., the early promoter), and retroviruses (e.g., Rous sarcoma virus). Other transcription control regions include those derived from vertebrate genes such as actin, heat shock protein, bovine growth hormone and rabbit alpha-globin, as well as other sequences capable of controlling gene expression in eukaryotic cells. Additional suitable transcription control regions include tissue-specific promoters and enhancers as well as inducible promoters (e.g., promoter inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Once an AVP, or a fragment thereof has been produced by recombinant expression or by chemical peptide synthesis, it can be purified, if necessary, by any method known in the art for purification of a peptide molecule, for example, by chromatography (e.g., ion exchange, affinity, and sizing column chromatography), centrifugation, differential solubility, or by any other standard technique for the purification of proteins. Further, the AVP, or a fragment thereof, can be fused to heterologous polypeptide sequences described herein or otherwise known in the art to facilitate purification or to produce a therapeutic peptide.

Once isolated, an AVP, or a fragment thereof, can, if desired, be further purified, e.g., by high performance liquid chromatography (see, e.g., Fisher, Laboratory Techniques in Biochemistry and Molecular Biology (Work and Burdon, eds., Elsevier, 1980); the disclosure of which is incorporated herein by reference), or by gel filtration chromatography, such as on a SUPERDEX™ 75 column (Pharmacia Biotech AB, Uppsala, Sweden). Similar purification steps can be taken for and AVP, or a fragment thereof, produced through chemical peptide synthesis. Once cleaved from the resin, the isolated AVP, or a fragment thereof, may be further purified as described above.

The AVPs described herein can be modified to overcome to improve their stability (e.g., storage stability and/or in vivo pharmacokinetics), such as to improve their protease resistance and to avoid degradation. The AVPs may be modified to increase enzymatic resistance using, e.g., sequence specific modifications, e.g., those affecting the primary structure of the peptide itself, and by making global modifications to the peptide, e.g., those which alter certain overall physicochemical characteristics of the peptide. Introduced strategically, such modifications can reduce the effects of natural physiological processes which would otherwise eliminate or inactivate a peptide whose action is desired, e.g., enzymatic degradation and/or clearance by renal ultrafiltration. Sequence specific modifications include, e.g., incorporation of proteolysis-resistant amino acids into the AVP (e.g., one or more D-amino acids) or more involved modifications including cyclization between naturally occurring side-chain functions, e.g., disulfide formation (Cys-Cys), or lactamization (Lys-Glu or Lys-Asp). Additional modifications include cyclization between unnatural amino acid surrogates within the peptide backbone.

Global modifications to the AVPs described herein may include peptide lipidation, e.g., palmitoylation and/or PEGylation. Palmitoylation has the effect of creating a circulating reservoir of peptide which reversibly associates with naturally abundant albumin in blood serum. A peptide associated with albumin effectively escapes renal ultrafiltration since the size of the associated complex is above the glomerular filtration cutoff. As the peptide dissociates from the surface of the albumin, it is again free to interact with endogenous receptors. PEGylation has the effect of physically shielding the peptide from proteolysis and imparts significant hydrophilicity which upon hydration greatly increases the hydrodynamic radius of the therapeutic molecule to overcome renal clearance.

Pharmaceutical Compositions

The broad-spectrum antiviral peptides and polynucleotides described herein can be prepared as compositions that contain a pharmaceutically acceptable carrier, excipient, or stabilizer known in the art (*Remington: The Science and Practice of Pharmacy* 20th Ed., 2000, Lippincott Williams and Wilkins, Ed. K. E. Hoover), in the form of a lyophilized formulation, or as an aqueous solution. Acceptable carriers, excipients, or stabilizers are non-toxic to recipients at the employed dosages and concentrations, and may include buffers such as phosphate, citrate, and other organic acids; antioxidants including ascorbic acid and methionine; preservatives (e.g., octadecyldimethylbenzyl ammonium chloride, hexamethonium chloride, benzalkonium chloride, benzethonium chloride, phenol, butyl or benzyl alcohol, alkyl parabens such as methyl or propyl paraben, catechol, resorcinol, cyclohexanol, 3-pentanol, and m-cresol); low molecular weight (less than about 10 residues) polypeptides; proteins such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, marmose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PIURONICS™ or polyethylene glycol (PEG). Pharmaceutically acceptable excipients are further described herein.

The compositions (e.g., when used in the methods described herein) generally include, by way of example and not limitation, an effective amount (e.g., an amount sufficient to mitigate infection, alleviate a symptom of infection, prevent or reduce the progression of disease, and/or reduce the risk of developing an infection) of an AVP or a fragment thereof (e.g., an AVP of Table 1), and variants thereof with at least 75% sequence identity thereto, and variants thereof.

For example, the compositions can be formulated to include between about 1 μg/ml and about 1 g/ml of the AVP (e.g., between 0.5 μg/ml and 300 μg/ml, 1 μg/ml and 50 μg/ml, 20 μg/ml and 120 μg/ml, 40 μg/ml and 200 μg/ml, 30 g/ml and 150 μg/ml, 40 μg/ml and 100 μg/ml, 50 μg/ml and 80 μg/ml, or 60 μg/ml and 70 μg/ml, or 10 mg/ml and 300 mg/ml, 20 mg/ml and 120 mg/ml, 40 mg/ml and 200 mg/ml, 30 mg/ml and 150 mg/ml, 40 mg/ml and 100 mg/ml, 50 mg/ml and 80 mg/ml, or 60 mg/ml and 70 mg/ml of the AVP).

The compositions (e.g., when used in the methods described herein) generally include, by way of example and not limitation, an effective amount (e.g., an amount sufficient to mitigate infection, and/or prevent or reduce the progression of the infection) of an AVP from Table 1 or 2, or any variants thereof with at least 75% sequence identity thereto, and variants thereof.

The pharmaceutical composition can further include an additional agent that serves to enhance and/or complement the desired effect. By way of example, to enhance the efficacy of the one or more AVPs or fragments or combinations thereof, administered as a pharmaceutical composition, the pharmaceutical composition may further contain an antiviral agent, an antiviral vaccine, an antimicrobial agent (such as an antibacterial agent or an antifungal agent), an anti-inflammatory agent, or an antiparasitic agent.

For example, as used herein, an antiviral agent can be Abacavir, Acyclovir, Adefovir dipivoxil, Amantadine, Amprenavir, Asunaprevir, Atazanavir, Boceprevir, Brivudine, Cidofovir, Daclatasvir, Darunavir, Dasabuvir, Delavirdine, Didanosine, Docosanol, Dolutegravir, Dolutegravir, Efavirenz, EIDD-2801, Elbasvir, Elvitegravir, Emtricitabine, Enfuvirtide, Entecavir, Etravirine, Famciclovir, Favipiravir (favilavir), Fosamprenavir, Foscarnet, Galidesivir, Ganciclovir, Grazoprevir, Idoxuridine, Indinavir, Lamivudine, Laninamivir octanoate, Ledipasvir, Lopinavir, Maraviroc, Nelfinavir, Nevirapine, Ombitasvir, Oseltamivir, Palivizumab, Paritaprevir, Penciclovir, Peramivir, Raltegravir, Remdesivir, Ribavirin, Rilpivirine, Rimantadine, Ritonavir, RSV-IGIV, Saquinavir, Simeprevir, SNG001, Sofosbuvir, Stavudine, Telaprevir, Telbivudine, Tenofovir alafenamide, Tenofovir disoproxil fumarate, Tipranavir, Trifluridine, Valacyclovir, Valganciclovir, Vaniprevir, Vidarabine, Zalcitabine, Zanamivir, Zidovudine, or pharmaceutically acceptable salts thereof, or a combination thereof.

For example, as used herein, an antiviral vaccine can be an Adenovirus Type 4 and Type 7 vaccine, a Dengue Tetravalent vaccine, an Ebola Zaire vaccine, a Hepatitis A vaccine, a Hepatitis B vaccine, a Human Papillomavirus Quadrivalent vaccine, an Influenza A (H1N1) vaccine, an Influenza A (H5N1) vaccine, a Japanese Encephalitis Virus vaccine, a Measles, Mumps, and Rubella Virus vaccine, a Poliovirus vaccine, a Rotavirus vaccine, a SARS-CoV-2 vaccine (e.g., Pfizer-BioNTech COVID-19 Vaccine (BNT162b2), Moderna COVID-19 Vaccine (mRNA-1273), AstraZeneca COVID-19 Vaccine (AZD1222), Janssen COVID-19 Vaccine (JNJ-78436735; Ad26.COV2.S)), a Smallpox and Monkeypox vaccine, a Smallpox (Vaccinia) vaccine, a Varicella Virus vaccine, a Yellow Fever vaccine, a Zoster vaccine, or a combination thereof.

For example, as used herein, an antibacterial agent can be Afenide, Amikacin, Amoxicillin, Ampicillin, Arsphenamine, Augmentin, Azithromycin, Azlocillin, Aztreonam, Bacampicillin, Bacitracin, Balofloxacin, Besifloxacin, Capreomycin, Carbacephem (loracarbef), Carbenicillin, Cefacetrile (cephacetrile), Cefaclomezine, Cefaclor, Cefadroxil (cefadroxyl), Cefalexin (cephalexin), Cefaloglycin (cephaloglycin), Cefalonium (cephalonium), Cefaloram, Cefaloridine (cephaloradine), Cefalotin (cephalothin), Cefamandole, Cefaparole, Cefapirin (cephapirin), Cefatrizine, Cefazaflur, Cefazedone, Cefazolin (cephazolin), Cefcanel, Cefcapene, Cefclidine, Cefdaloxime, Cefdinir, Cefditoren, Cefedrolor, Cefempidone, Cefepime, Cefetamet, Cefetrizole, Cefivitril, Cefixime, Cefluprenam, Cefmatilen, Cefmenoxime, Cefmepidium, Cefmetazole, Cefodizime, Cefonicid, Cefoperazone, Cefoselis, Cefotaxime, Cefotetan, Cefovecin, Cefoxazole, Cefoxitin, Cefozopran, Cefpimizole, Cefpirome, Cefpodoxime, Cefprozil (cefproxil), Cefquinome, Cefradine (cephradine), Cefrotil, Cefroxadine, Cefsumide, Ceftaroline, Ceftazidime, Ceftazidime/Avibactam, Cefteram, Ceftezole, Ceftibuten, Ceftiofur, Ceftiolene, Ceftioxide, Ceftizoxime, Ceftobiprole, Ceftriaxone, Cefuracetime, Cefuroxime, Cefuzonam, Cephalexin, Chloramphenicol, Chlorhexidine, Ciprofloxacin, Clarithromycin, Clavulanic Acid, Clinafloxacin, Clindamycin, Cloxacillin, Colimycin, Colistimethate, Colistin, Crysticillin, Cycloserine 2, Demeclocycline, Dicloxacillin, Dirithromycin, Doripenem, Doxycycline, Efprozil, Enoxacin, Ertapenem, Erythromycin, Ethambutol, Flucloxacillin, Flumequine, Fosfomycin, Furazolidone, Gatifloxacin, Geldanamycin, Gemifloxacin, Gentamicin, Glycopeptides, Grepafloxacin, Herbimycin, Imipenem, Isoniazid, Kanamycin, Levofloxacin, Lincomycin, Linezolid, Lipoglycopeptides, Lomefloxacin, Meropenem, Meticillin, Metronidazole, Mezlocillin, Minocycline, Mitomycin, Moxifloxacin, Mupirocin, Nadifloxacin, Nafcillin, Nalidixic Acid, Neomycin, Netilmicin, Nitrofurantoin, Norfloxacin, Ofloxacin, Oxacillin, Oxazolidinones, Oxolinic Acid, Oxytetracycline, Oxytetracycline, Paromomycin, Pazufloxacin, Pefloxacin, Penicillin G, Penicillin V, Pipemidic Acid, Piperacillin, Piromidic Acid, Pivampicillin, Pivmecillinam, Platensimycin, Polymyxin B, Pristinamycin, Prontosil, Prulifloxacin, Pvampicillin, Pyrazinamide, Quinupristin/dalfopristin, Rifabutin, Rifalazil, Rifampin, Rifamycin, Rifapentine, Rosoxacin, Roxithromycin, Rufloxacin, Sitafloxacin, Sparfloxacin, Spectinomycin, Spiramycin, Streptomycin, Sulbactam, Sulfacetamide, Sulfamethizole, Sulfamethoxazole, Sulfanilimide, Sulfisoxazole, Sulphonamides, Sultamicillin, Teicoplanin, Telavancin, Telithromycin, Temafloxacin, Tetracycline, Thiamphenicol, Ticarcillin, Tigecycline, Tinidazole, Tobramycin, Tosufloxacin, Trimethoprim, Trimethoprim-Sulfamethoxazole, Troleandomycin, Trovafloxacin, Tuberactinomycin, Vancomycin, Viomycin, or pharmaceutically acceptable salts thereof, or a combination thereof.

For example, an antifungal agent can be used with the compositions described herein and include those that are used by medical professionals in the treatment of microbial infections, such as candidiasis, including, for example, an azole (e.g., a triazole, such as fluconazole, albaconazole, efinaconazole, epoxiconazole, isavuconazole, itraconazole, posaconazole, propiconazole, ravuconazole, terconazole, and voriconazole; an imidazole, such as bifonazole, butoconazole, clotrimazole, eberconazole, econazole, fenticonazole, flutrimazole, isoconazole, ketoconazole, luliconazole, miconazole, omoconazole, oxiconazole, sertaconazole, sulconazole, and tioconazole; and a thiazole, such as abafungin), a polyene (e.g., amphotericin B, candicidin, filipin, hamycin, natamycin, nystatin, and rimocidin), an allylamine (e.g., amorolfin, butenafine, naftifine, and terbinafine), an echinocandin (e.g., anidulafungin, biafungin (e.g., CD101), caspofungin, and micafungin), lanosterol demethylase inhibitors (e.g., VT-1161) and other antifungal agents, including, but not limited to, benzoic acid, ciclopirox olamine, enfumafungin (e.g., SCY-078), 5-flucytosine, griseofulvin, haloprogin, tolnaftate, aminocandin, chlordantoin, chlorphenesin, nifuroxime, undecylenic acid, and crystal violet, and pharmaceutically acceptable salts or esters thereof.

For example, as used herein, an anti-inflammatory agent can be corticosteroids (e.g., glucocorticoids (e.g., dexamethasone, prednisone, and hydrocortisone)) and non-steroidal anti-inflammatory drugs (e.g., aspirin, propionic acid derivatives such as ibuprofen, fenoprofen, ketoprofen, flurbiprofen, oxaprozin and naproxen, acetic acid derivatives such as sulindac, indomethacin, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib).

For example, as used herein, an antiparasitic agent can be albendazole, amphotericin B, artemether, atovaquone, chloroquine, hydroxychloroquine, ivermectin, lumefantrine, mebendazole, mefloquine, miltefosine, nitazoxanide, paromomycin, praziquantel, primaquine, proguanil, pyrimethamine, quinidine, quinine, tinidazole, or pharmaceutically acceptable salts thereof, or a combination thereof.

Methods of Treatment

Generally, a composition containing an AVP can be administered (e.g., intravenously or orally) to a subject (e.g., a human or other mammal, such as a bovine, equine, canine, ovine, or feline in need thereof) as a medicament (e.g., for treating a medical condition (e.g., a viral infection)). The medical condition may be, e.g., meningitis, encephalitis, urinary tract infection (e.g., bladder infection), respiratory illness (e.g., bronchitis, croup, flu, pneumonia), liver disease (e.g., hepatitis, cirrhosis), measles, acquired immunodeficiency syndrome (AIDS), coronavirus disease 2019 (COVID-19), sepsis (e.g., septic shock), viral hemorrhagic fever, skin disorder (e.g., cold sores, genital sores, rash), or a digestive system disorder (e.g., gastroenteritis). The subject may be at risk for viral infection (e.g., respiratory illness) due to their age, a compromised immune system, heart disease, diabetes, autoimmune condition, lung condition, chronic kidney or liver disease, travel or residence in an endemic region, travel or residence in a region experiencing an outbreak, exposure to body fluids of infected individual (e.g., injection drug use, sexual contact), exposure to zoonotic vector (e.g., mosquito, bat, nonhuman primate), admission to a health care facility (e.g., an intensive care unit or long-term health care facility), or the subject may one that has previously received an antiviral treatment (e.g., an antiviral drug and/or a corticosteroid) that did not resolve the infection. The infection may also be one caused by a drug-resistant pathogen. The subject may be one that is experiencing severe organ problems (e.g., organ failure, such as failure of the lungs, kidney, bladder, and/or digestive system), or at a high risk of infection, such as a subject undergoing surgery, organ transplantation, and/or chemotherapy. For example, the subject may be one that is undergoing a surgery (e.g., organ transplantation), and the AVP composition is administered to treat or reduce the risk of viral infection pre- or post-surgery. The subject may also be treated for a different condition (e.g., cancer), and the AVP composition is administered (e.g., prophylactically) to treat or reduce the risk of viral infection following a treatment (e.g., surgery).

For example, a composition containing an AVP described herein may be administered to a subject in need thereof (e.g., a subject, such as a human of other mammal (e.g., a non-human primate, bovine, equine, canine, ovine, or feline) that has been diagnosed with a medical condition) by a variety of routes, such as local administration at or near the site affected by the medical condition (e.g., injection near a viral infection), intravenous, parenteral, intradermal, transdermal, intramuscular, intranasal, subcutaneous, percutaneous, intratracheal, intraperitoneal, intraarterial, intravascular, inhalation, perfusion, lavage, topical, and oral administration. The most suitable route for administration in any given case may depend on the particular AVP or composition administered, the subject, pharmaceutical formulation methods, administration methods (e.g., administration time and administration route), the subject's age, body weight, sex, severity of the medical condition (e.g., severity of the viral infection), the subject's diet, and the subject's excretion rate. Compositions may be administered once, or more than once (e.g., once annually, twice annually, the times annually, bi-monthly, monthly, bi-weekly, weekly, daily, or more than once daily). For local administration, AVPs may be administered by any means that places the AVP in a desired location, including catheter, syringe, shunt, stent, microcatheter, pump, implantation with a device, or implantation with a scaffold.

A composition containing an AVP described herein may be administered to provide pre-exposure prophylaxis or after a subject has been diagnosed as having a viral infection (e.g., infection by SARS-CoV-2 or other virus disclosed herein, or a variant thereof) or after exposure of a subject to an infective agent, such as a virus (e.g., a coronavirus, such as a SARS-CoV-2 or other virus disclosed herein, or a variant thereof). The composition containing an AVP may be administered, for example, 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, or even 3, 4, or 6 months pre-exposure to a virus, or may be administered to the subject 15-30 minutes or 1, 2, 3, 4, 5, 6, 7, 8, 9, 10, 12, 20, 24, 48, or 72 hours, 2, 3, 5, or 7 days, 2, 4, 6 or 8 weeks, 3, 4, 6, or 9 months, 1, 2, 3, 4, 5, 6, 7, 8, 9, 10, 15, or 20 years or post-exposure to a virus (e.g., SARS-CoV-2 or other virus disclosed herein, or a variant thereof).

The methods described herein may involve coordinated administration of (i) an AVP, and (ii) an antiviral agent (e.g., an agent that treats viral infection) or an antiviral vaccine. The AVP and antiviral agent are generally as described elsewhere herein, but can be, as examples, an AVP described herein (e.g., an AVP of any one of SEQ ID NOs: 1-47 or 54-59, such as the AVPs of SEQ ID NOs: 1-28), and/or variants thereof, and oseltamivir phosphate. In another example, the AVP and antiviral vaccine can be an AVP described herein (e.g., an AVP of any one of SEQ ID NOs:

1-47 or 54-59, such as the AVPs of SEQ ID NOs: 1-28), and/or variants thereof, and a SARS-CoV-2 vaccine.

There are many different approaches to coordinated administration of an AVP and an antiviral agent that can be used in the intervention of infection. For example, the antiviral agent may be administered first, followed by administration of the AVP. In another example, the AVP and the antiviral agent may be administered concurrently (e.g., in the same pharmaceutical composition or in separate pharmaceutical compositions). In another example, the AVP may be administered first, followed by administration of an antiviral agent.

For instance, the method may include treatment with an antiviral agent prior to AVP administration. Taking this approach facilitates treatment of an acute episode quickly with the antiviral agent, while supplementing the action of the antiviral agent with the AVP in addressing the acute attack.

In one example, a subject can be treated with an antiviral agent 1-4 times (e.g., 2-3 times) before AVP administration, and the antiviral treatment takes place, for example, within a time frame of 1, 2, or 3 hours, days, or weeks prior to AVP administration. Thus, in a specific example, a treatment with an antiviral agent can be carried out on days −14, −11, and −8 relative to day 0, which is the day on which administration of the AVP takes place. Any of the antiviral treatment and/or AVP treatment can vary (e.g., 1 or 2 days) before or after the days noted above.

In another example, antiviral treatment takes place concurrently with AVP administration, in addition to (or instead of) prior antiviral treatment according to, for example, a schedule as noted above. Thus, in one specific example, antiviral treatment takes place on days −14, −11, and −8 (+1 or 2 days for each day of administration), and also on day 0, the same day as AVP administration. The simultaneous treatment with an antiviral agent and an AVP described herein (e.g., in the same pharmaceutical composition or in separate pharmaceutical compositions), can continue, and be monitored by one skilled in the art, until effective treatment of the infection.

In another example, AVP administration takes place before a subject is treated with an antiviral agent, for example, within a time frame of 1, 2, or 3 hours, days, or weeks prior to the antiviral agent. Thus, in a specific example, AVP administration can be carried out on days −14, −11, and −8 relative to day 0, which is the day on which administration of the antiviral agent takes place. Any of the AVP treatment and/or antiviral treatment can vary (e.g., 1 or 2 days) before or after the days noted above.

The AVP described herein may be used for a treatment of an infection after the treatment with traditional antivirals has failed.

Compositions as described herein can be delivered to a mammalian subject (e.g., a human or other mammal) using a variety of known routes and techniques. For example, a composition can be provided as an injectable solution, suspension, or emulsion, and administered via intramuscular, subcutaneous, intradermal, intracavity, parenteral, epidermal, intraarterial, intraperitoneal, or intravenous injection using conventional methods, such as a syringe, or using a liquid jet injection system. Compositions can also be administered topically to skin or mucosa! tissue, such as nasally, intratracheally, intestinal, rectally, or vaginally, or provided as a finely divided spray suitable for respiratory or pulmonary administration. Other modes of administration include oral administration, suppositories, and active or passive transdermal delivery techniques.

The compositions described herein can be administered to a subject (e.g., a human subject or other mammal, such as a bovine, equine, canine, ovine, or feline, that has or is at risk of developing a viral infection) in an amount that is compatible with the dosage formulation and that will be prophylactically and/or therapeutically effective. An appropriate effective amount will fall in a relatively broad range but can be readily determined by one of skill in the art by routine trials. The "Physician's Desk Reference" and "Goodman and Gilman's The Pharmacological Basis of Therapies" are useful for the purpose of determining the amount needed. An adequate dose of the active antiviral agents described herein may vary depending on such factors as preparation method, administration method, severity of symptoms, administration time, administration route, rate of excretion, and responsivity. Generally, the antiviral agent will be administered according to the label approved by the relevant regulatory authority. An adequate dose of the AVPs described herein may vary depending on the administration route, age of the subject, the severity of infection, and the identity of the infecting pathogen. A physician or veterinarian of ordinary skill in the art can determine the administration dose effective for treatment.

Dosage and Administration

The pharmaceutical compositions described herein can be administered to a subject (e.g., a human or other mammal, such as a non-human primate, bovine, equine, canine, ovine, or feline) in a variety of ways. For example, the pharmaceutical compositions may be formulated for and/or administered orally, buccally, sublingually, parenterally, intravenously, subcutaneously, intramedullary, intranasally, as a suppository, using a flash formulation, topically, intradermally, subcutaneously, via pulmonary delivery, via intraarterial injection, ophthalmically, optically, intrathecally, or via a mucosal route.

In general, the dosage of a pharmaceutical composition containing an AVP described herein, such as, e.g., an AVP of any one of SEQ ID NOs: 1-47 or 54-59, such as the AVPs of SEQ ID NOs: 1-28, e.g., an AVP of SEQ ID NO: 15 or 21, and/or a variant thereof with at least 75% sequence identity thereto) in a pharmaceutical composition described herein may be in the range of from about 1 pg to about 10 g (e.g., 1 pg-10 pg, e.g., 2 pg, 3 pg, 4 pg, 5 pg, 6 pg, 7 pg, 8 pg, 9 pg, 10 pg, e.g., 10 pg-100 pg, e.g., 20 pg, 30 pg, 40 pg, 50 pg, 60 pg, 70 pg, 80 pg, 90 pg, 100 pg, e.g., 100 pg-1 ng, e.g., 200 pg, 300 pg, 400 pg, 500 pg, 600 pg, 700 pg, 800 pg, 900 pg, 1 ng, e.g., 1 ng-10 ng, e.g., 2 ng, 3 ng, 4 ng, 5 ng, 6 ng, 7 ng, 8 ng, 9 ng, 10 ng, e.g., 10 ng-100 ng, e.g., 20 ng, 30 ng, 40 ng, 50 ng, 60 ng, 70 ng, 80 ng, 90 ng, 100 ng, e.g., 100 ng-1 μg, e.g., 200 ng, 300 ng, 400 ng, 500 ng, 600 ng, 700 ng, 800 ng, 900 ng, 1 μg, e.g., 1-10 μg, e.g., 1 μg, 2 μg, 3 μg, 4 μg, 5 μg, 6 μg, 7 μg, 8 μg, 9 μg, 10 μg, e.g., 10 μg-100 μg, e.g., 20 μg, 30 μg, 40 μg, 50 μg, 60 μg, 70 μg, 80 μg, 90 μg, 100 μg, e.g., 100 μg-1 mg, e.g., 200 μg, 300 μg, 400 μg, 500 μg, 600 μg, 700 μg, 800 μg, 900 μg, 1 mg, e.g., 1 mg-10 mg, e.g., 2 mg, 3 mg, 4 mg, 5 mg, 6 mg, 7 mg, 8 mg, 9 mg, 10 mg, e.g., 10 mg-100 mg, e.g., 20 mg, 30 mg, 40 mg, 50 mg, 60 mg, 70 mg, 80 mg, 90 mg, 100 mg, e.g., 100 mg-1 g, e.g., 200 mg, 300 mg, 400 mg, 500 mg, 600 mg, 700 mg, 800 mg, 900 mg, 1 g, e.g., 1 g-10 g, e.g., 2 g, 3 g, 4 g, 5 g, 6 g, 7 g, 8 g, 9 g, 10 g). For example, the AVP may be administered in any of the amounts described above at a volume in the range of 1 μl to 500 ml (e.g., 1-10 μl, e.g., 1 μl, 2 μl, 3 μl, 4 μl, 5 μl, 6 μl, 7 μl, 8 μl, 9 μl, 10 μl, e.g., 10 μl-100 μl, e.g., 20 μl, 30 μl, 40 μl, 50 μl, 60 μl, 70 μl, 80 μl, 90 μl, 100 μl, e.g., 100 μl-1 ml, e.g., 200 μl, 300 μl, 400 μl, 500 μl, 600 μl, 700 μl, 800 μl, 900 μl, 1 ml, e.g., 1 ml-10 ml, e.g., 2 ml, 3 ml, 4 ml, 5 ml, 6 ml, 7 ml, 8 ml, 9 ml, 10 ml, 10 ml-100 ml, e.g., 20 ml, 30 ml, 40 ml, 50 ml, 60 ml, 70 ml, 80 ml, 90 ml, 100 ml, e.g., 100 ml-500 ml, e.g., 200 ml, 300 ml, 400 ml, 500 ml).

The pharmaceutical composition may also be administered in a unit dose form or as a dose per mass or weight of the subject from about 0.01 mg/kg to about 100 mg/kg (e.g., 0.01-0.1 mg/kg, e.g., 0.02 0.03 mg/kg, 0.04 mg/kg, 0.05 mg/kg, 0.06 mg/kg, 0.07 mg/kg, 0.08 mg/kg, 0.09 mg/kg, 0.1 mg/kg, e.g., 0.1-1 mg/kg, e.g., 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, e.g., 1-10 mg/kg, e.g., 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, e.g., 10-100 mg/kg, e.g., 20 mg/kg, 30 mg/kg, 40 mg/kg, 50 mg/kg, 60 mg/kg, 70 mg/kg, 80 mg/kg, 90 mg/kg, 100 mg/kg). The dose may also be administered as a dose per mass or weight of the subject per unit day (e.g., 0.1-10 mg/kg/day).

The dosage regimen may be determined by the clinical indication being addressed, as well as by various subject variables (e.g., weight, age, sex) and clinical presentation (e.g., extent or severity of disease). Furthermore, the pharmaceutical compositions may be administered continuously or divided into dosages given per a given time frame. The composition may be administered (e.g., systemically), for example, one or more times every hour, day, week, month, or year.

Kits

Also featured are kits containing an AVP described herein, such as, e.g., an AVP of any one of SEQ ID NOs: 1-47 or 54-59, such as the AVPs of SEQ ID NOs: 1-28, e.g., an AVP of SEQ ID NO: 15 or 21, and/or a variant thereof with at least 75% sequence identity thereto), e.g., for use in the instant methods. Kits of the invention include one or more containers comprising, for example, AVPs, polynucleotides encoding one or more AVPs, combinations thereof, and fragments thereof, and, optionally, instructions for use in accordance with any of the methods described herein.

Generally, these instructions comprise a description of administration or instructions for performance of an assay. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also envisioned The kits may be provided in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (e.g., the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). Kits may optionally provide additional components such as buffers and interpretive information. Normally, the kit comprises a container and a label or package insert(s) on or associated with the container.

EXAMPLES

The following examples are put forth to provide those of ordinary skill in the art with a description of how the compositions and methods described herein may be used, made, and evaluated, and are intended to be purely exemplary of the invention and are not intended to limit the scope of what the inventors regard as their invention.

Example 1. Segmented Peptide Analysis and Design of Gain-of-Function AVPs

Gain-of-function peptides that preferentially bind the viral envelope with minimal cellular binding were designed and sequence motifs that drive antiviral activity were identified. IT1b (SEQ ID NO: 42), an interfacially active peptide, was segmented into six segment peptides that were tested for antiviral activity (FIG. 1A). IT1b contains distinct regions that can be isolated and assayed. Peptides from the N-terminal, middle, and C-terminal regions were synthesized. Full length IT1b was also included in these assays as a benchmark.

Lassa pseudovirus (LASVpv) was used to test for antiviral activity. To conduct this assay, LASVpv was treated with serial dilutions of IT1b peptide segments, incubated for 1 hour, then added to HEK cells. After 72 hours of incubation at 37° C., cells were lysed, and luciferase expression was measured using BRIGHT-GLO™ as a measure of infectivity. The Lassa pseudovirus neutralization assay was performed as described in Example 15.

Our screens revealed that full length IT1b was far more potent than all the segments, suggesting that antiviral activity is a combination of traits not isolated to one segment (FIG. 1B). Full length IT1b had an ECso nearly an order of magnitude lower than the next most active peptide (i.e., Cterm-Cat). The screening results also revealed that, of the segmented peptides, the C-terminal peptides are the most potent inhibitors of viral activity, the cationic middle segment (Mid-Cat) have moderate potency, and the N-terminal segments are weak inhibitors. The middle segment (Mid) showed no antiviral activity.

The segmented peptide analysis using IT1b guided the intelligent design of six sets of novel AVPs, which were named gain-of-function peptides (SEQ ID NOs: 2-28). These novel peptides were used to determine which specific motifs drive antiviral activity. The template peptide TL3 (Template Leucine 3) was designed based on common traits of interfacially active peptides (SEQ ID NO: 30-42, 44-47). This peptide includes RRGW-and-WGRR terminal cassettes. Double arginines with a glycine spacer between an aromatic residue is a motif present in most of the interfacially active peptides. The core of the peptide consists of one central arginine with three leucines on each side. This sequence models the core of many interfacially active peptides; mostly hydrophobic with one polar or charged residue. Six total leucines were chosen because of the divisibility of this number. Test residues can be evenly spaced between one, two, or three leucines, which were used to test saturation of specific amino acids.

Example 2. Viral Inhibition Assays with Gain-of-Function AVPs

Figure 2B:
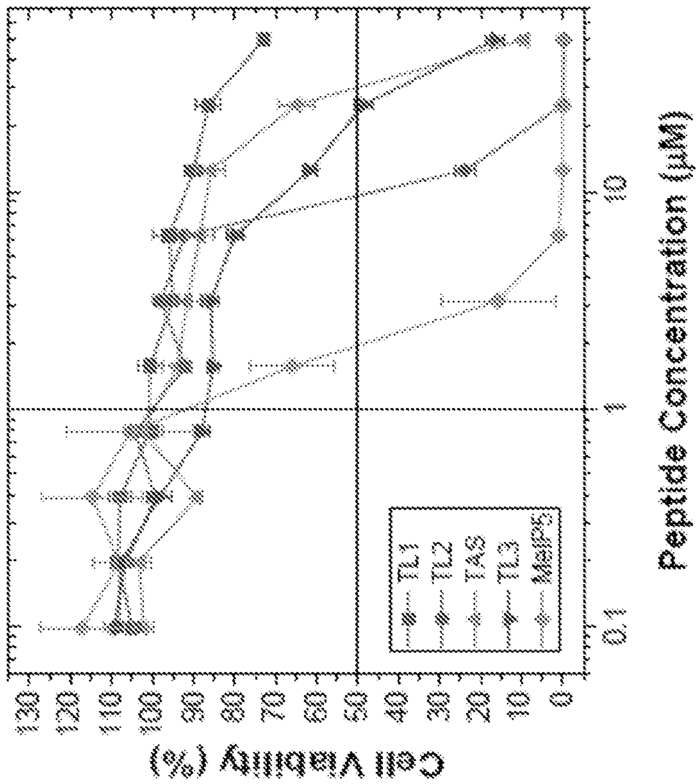
FIGS. 2A-2L are graphs showing the percentage of virus inhibition and percentage of cell viability for peptides in Table 1 (SEQ ID NOs: 2-28). LASVpv was incubated with serial dilutions of peptide for 1 hour then added to HEK cells. TL3 served as an internal reference. Infectivity was quantified by measuring luciferase expression translated from the LASVpv genome approximately 72 hours after infection. HEK cells were also treated with peptide alone and cell viability was determined by CELLTITER-GLO® approximately 72 hours after treatment. Inhibition measurements were fit to nonlinear curves which are shown here as solid lines (n=4-8, mean±SE).
Figure 2A:
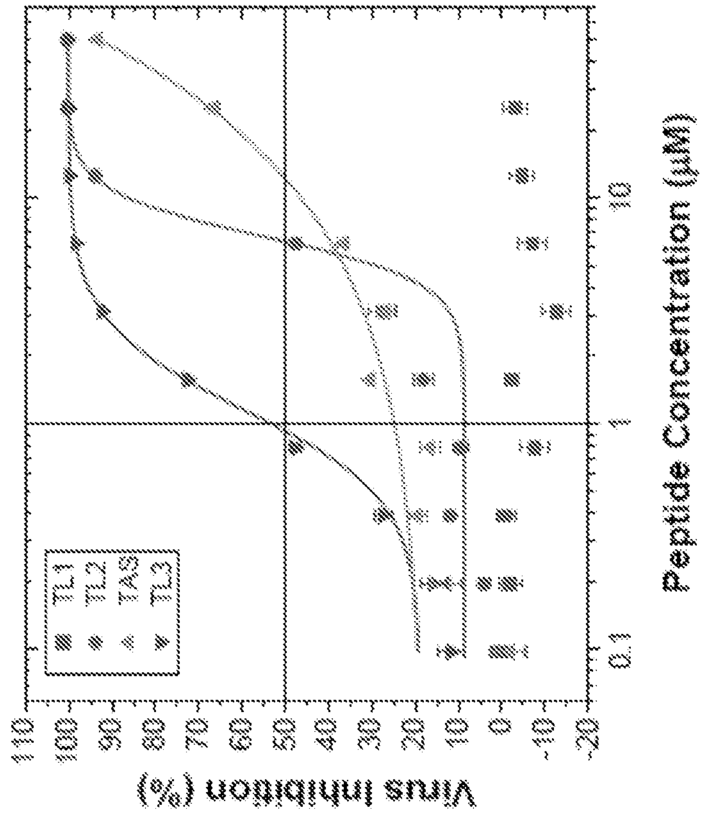
Figure 2D:
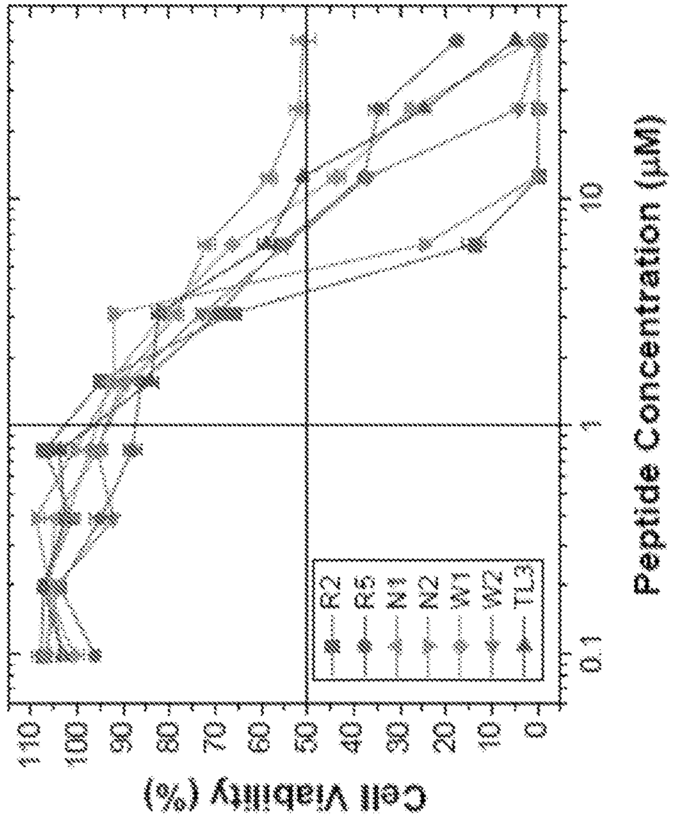
Figure 2C:
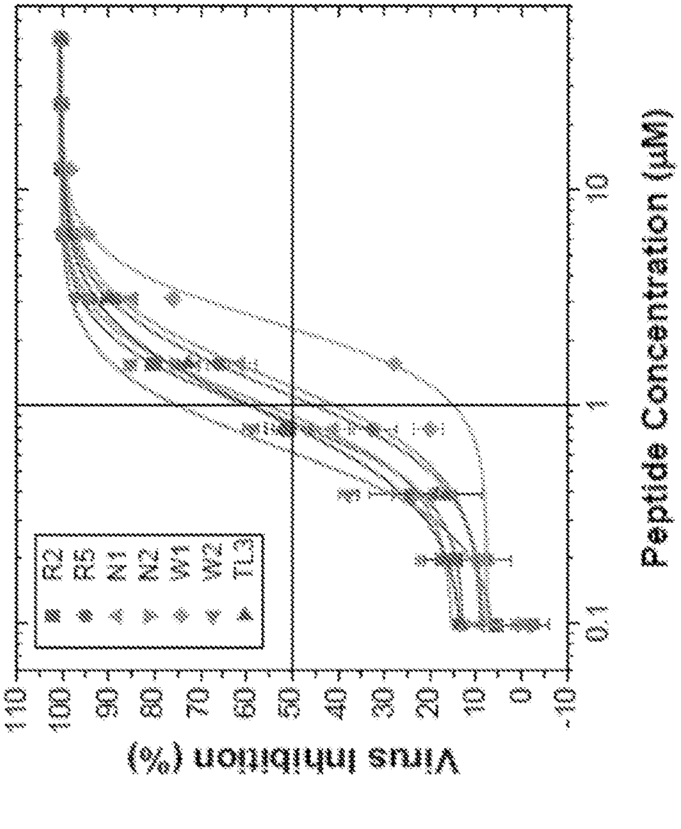
Figure 2E:
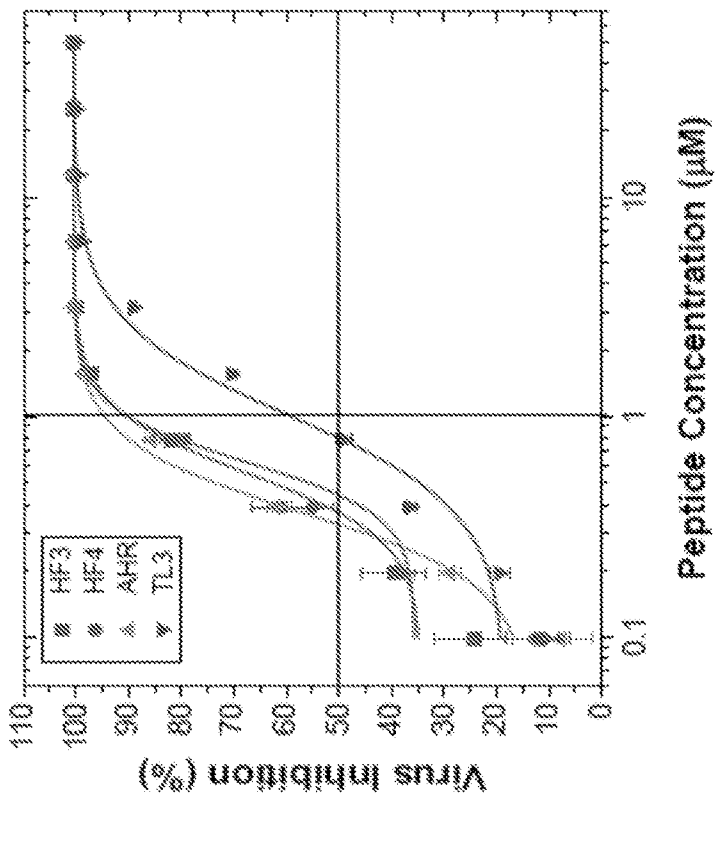
Figure 2F:
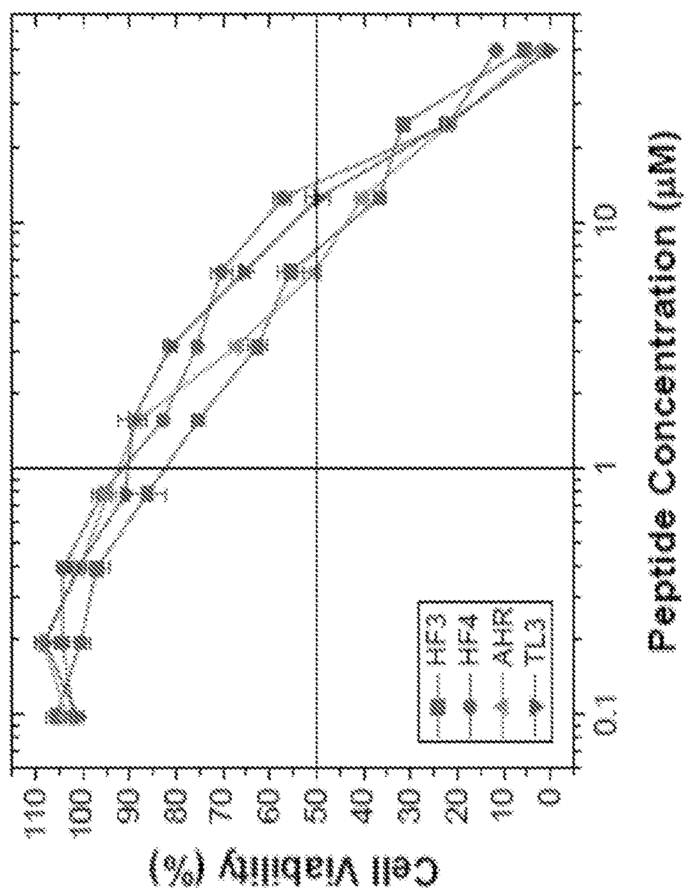
Figure 2G:
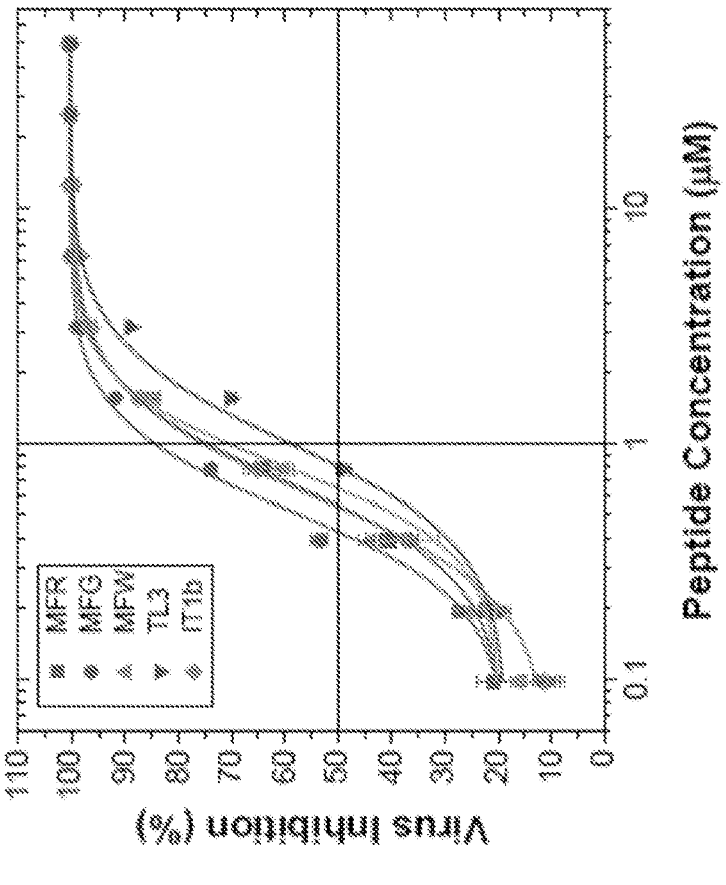
Figure 2H:
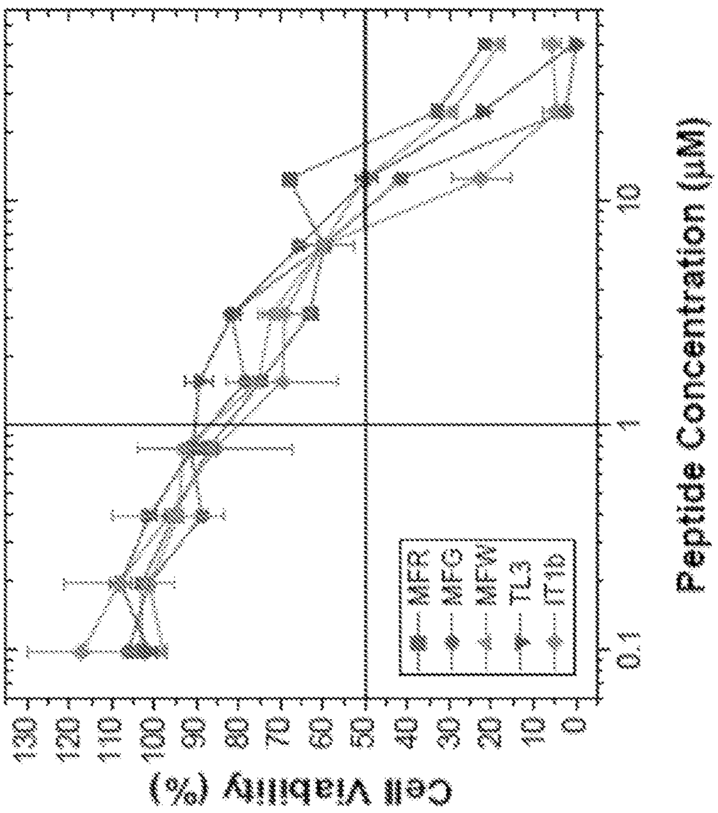
Figure 2I:
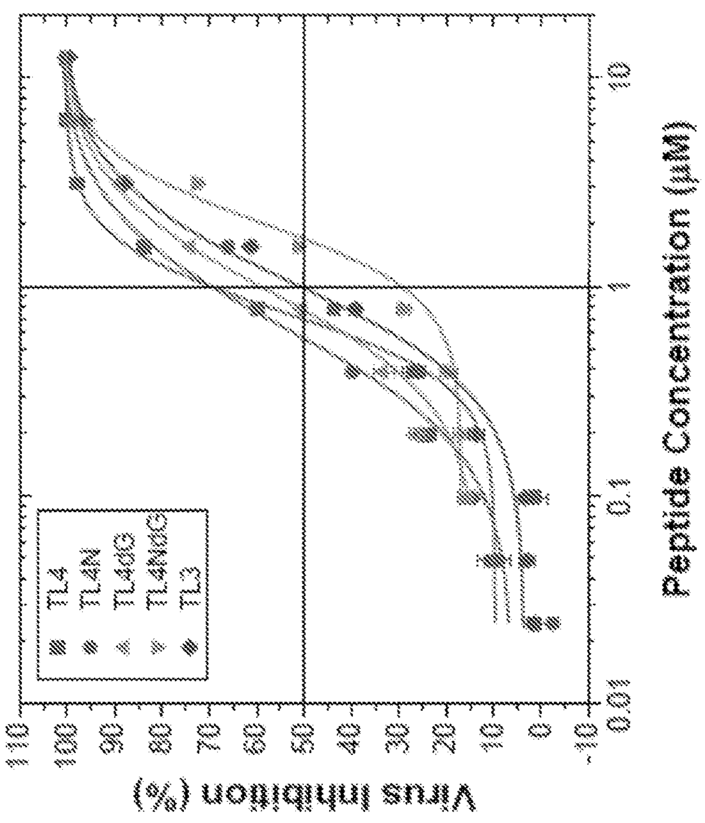

Gain-of-function AVPs (SEQ ID NOs: 2-28) were screened for antiviral activity against Lassa pseudovirus using virus inhibition assays. For the six sets of AVPs in Example 1, virus inhibition assay results for the first set of AVPs (FIG. 2A), second set of AVPs (FIG. 2C), third set of AVPs (FIG. 2E), fourth set of AVPs (FIG. 2G), fifth set of AVPs (FIG. 21), and sixth set of AVPs (FIG. 2K) are provided. TL3 was tested with all test peptide sets to serve as an internal reference. Peptides were tested for viral inhibition using the same methods described for segmented IT1b peptides in Example 1. The Lassa pseudovirus neutralization assay was performed as described in Example 15.

From the results of the first set of AVPs (FIG. 2A), these experiments revealed that a higher number of leucines in the hydrophobic core leads to greater antiviral activity. From the second set (FIG. 2C), we found that replacing the central arginine with asparagine decreases antiviral activity and replacing the central arginine with asparagine decreases antiviral activity. All peptides in the third set showed a dramatic increase in antiviral activity over TL3 (FIG. 2E), suggesting that the addition of multiple hydrophobic regions to the peptide dramatically increases activity. From the fourth set {FIG. 2G), which were designed to be a simplified version of IT1b, we found that antiviral activity is not dependent on a specific sequence but rather is a combination of molecular traits. From the fifth set (FIG. 21), we observed that all peptides, with the exception of TL4NdG, were more active than TL3. From the sixth set (FIG. 2K), we found that increased antiviral activity is likely due to the lengthening of the hydrophobic face and not the addition of an aromatic residue.

Example 3. Broad-spectrum Viral Inhibition Using Gain-of-Function AVPs

Four peptides were selected from the six test groups to measure broad-spectrum antiviral activity against dengue virus (DENV), herpes simplex virus (HSV), and adenovirus (AdV) using plaque assays (FIGS. 3A-3D). Plaque assays were performed as described in Example 15.

To determine the broad-spectrum activity of the interfacially active peptides, viruses with Class II and III fusion proteins were tested. A non-enveloped virus was also used to test the antiviral activity of the peptides. Peptide activity was tested against viruses containing each class of fusion protein to determine if one class is more susceptible to peptide induced inhibition. Dengue virus serotype 2 (DENV) was chosen to represent viruses with a Class II fusion protein (Hrobowski et al. (2005) *Viral. J.* 2:49). Herpes simplex virus type 1 (HSV-1) was chosen to represent viruses with a Class III fusion protein and also contains a large dsDNA genome (Backovic et al. (2009) *Curr. Opin. Struct. Biol.* 19(2):189-196; Patel et al. (2019) *Curr. Opin. Infect. Dis.* 32(1):51-55). Human adenovirus 5 was chosen to represent non-enveloped viruses to test whether AVPs inhibit virus only through destabilization of the viral envelope.

Figure 3A:
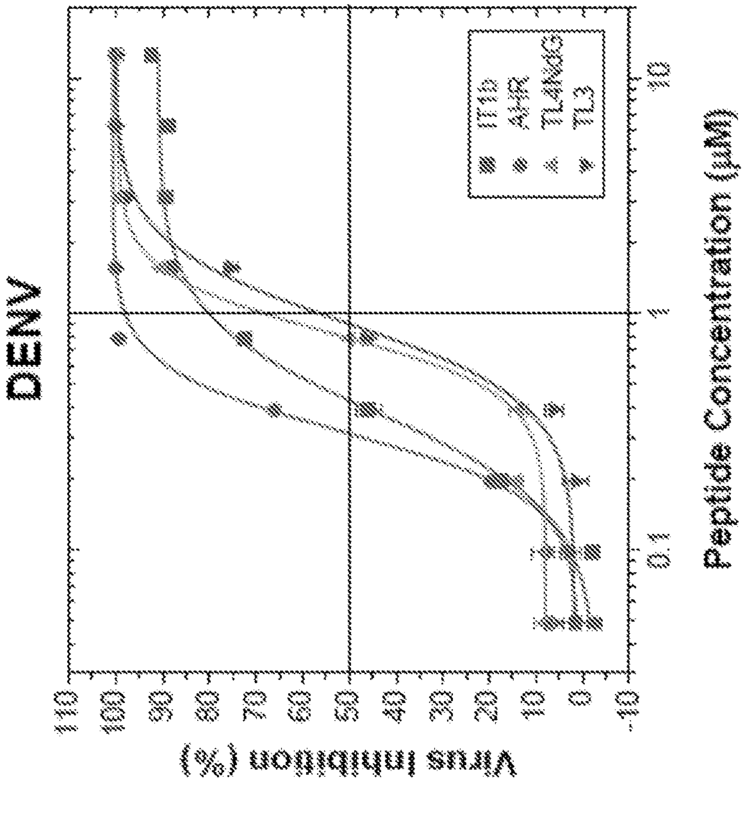
FIGS. 3A-3C are graphs showing peptide inhibition of diverse viruses using plaque assays. IT1b (SEQ ID NO: 42), AHR (SEQ ID NO: 15 or 21), TL4NdG (SEQ ID NO: 23), and TL3 (SEQ ID NO: 2) were tested against dengue virus type 2 (FIG. 3A), herpes simplex virus type 1 (FIG. 3B), and human adenovirus 5 (FIG. 3C). Plaque assays were used to quantify infectivity (n=6, mean±SE). Serial dilutions of peptide were incubated with virus for 1 hour, the inoculum was transferred to cells for 1 hour then was removed. Avicel overlay was added to cells and then incubated until viral plaques were visible by crystal violet staining. Inhibition measurements were fit to nonlinear curves which are shown here as solid lines.
Figure 3B:
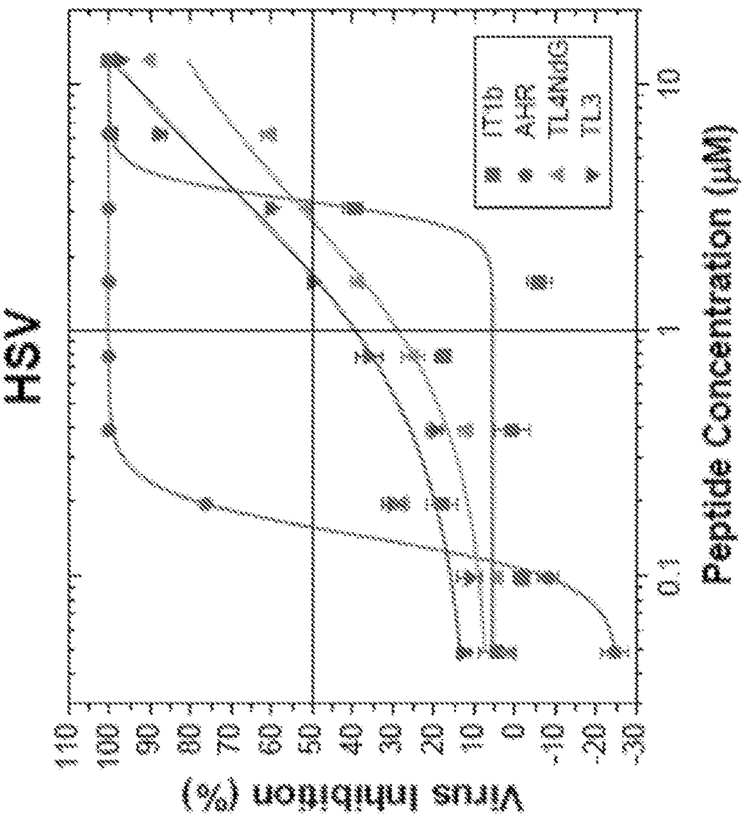
Figure 3D:
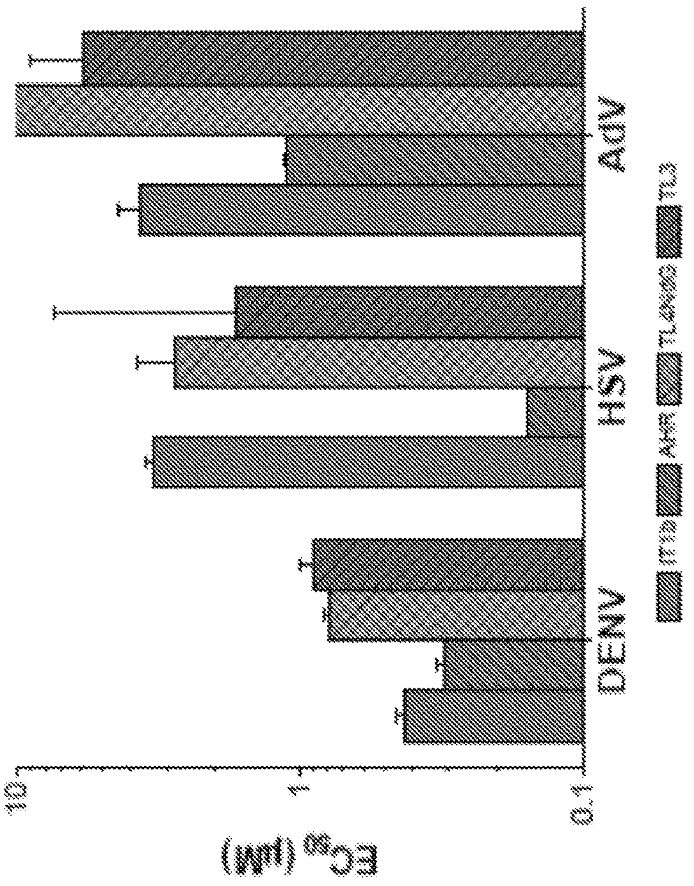
FIG. 3D is a graph showing ECso values that were calculated from nonlinear curve fits of the data shown in FIGS. 3A-3C. The ECso of TL4NdG against adenovirus was not calculated and is represented as >10 μM.
Figure 3C:
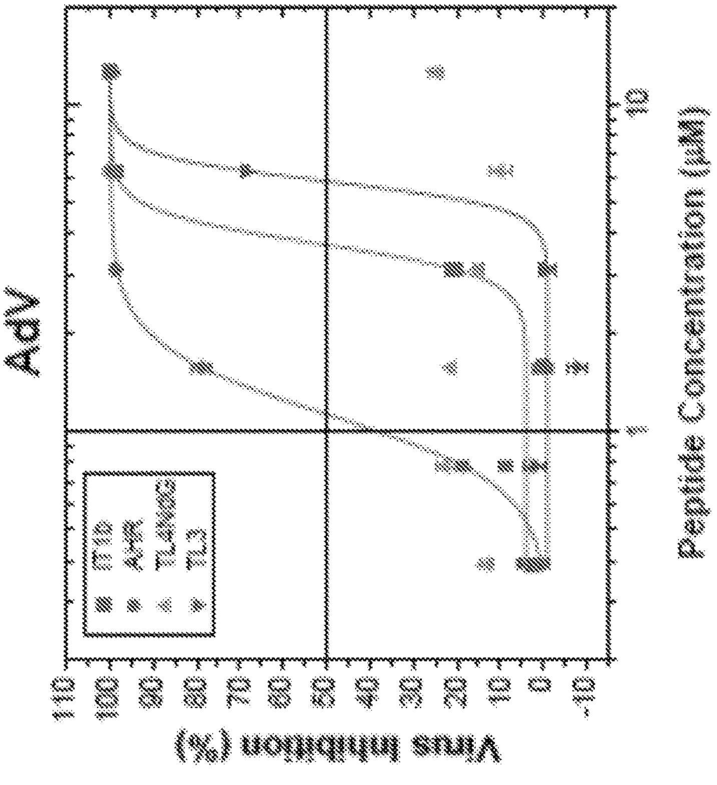

IT1b was selected so the gain-of-function peptides could be compared to interfacially active peptides. TL3 was selected because it is the template sequence from which most of the test peptides were designed. AHR was selected because it is the most potent antiviral test peptide. TL4NdG was selected because it is the least cytotoxic test peptide. DENV, HSV, and AdV were used to test for broad-spectrum antiviral activity. Our assays revealed that AHR is the most potent inhibitor of all three viruses. AHR was the most potent anti-DENV peptide with an ECso of 310 nM (FIG. 3D). AHR was also a significantly more potent inhibitor of HSV ($EC_{50}$ of 157 nM) and AdV ($EC_{50}$ of 1.1 μM) compared to the other three peptides. TL3 and TL4NdG have moderate activity against DENV and HSV. Against AdV, TL3 is weakly active while TL4NdG displays no activity. IT1b is a strong inhibitor of DENV but a weak inhibitor of HSV and AdV. Based on these data, multiple hydrophobic segments are the biggest driver of antiviral activity in the peptides tested.

Figure 7A:
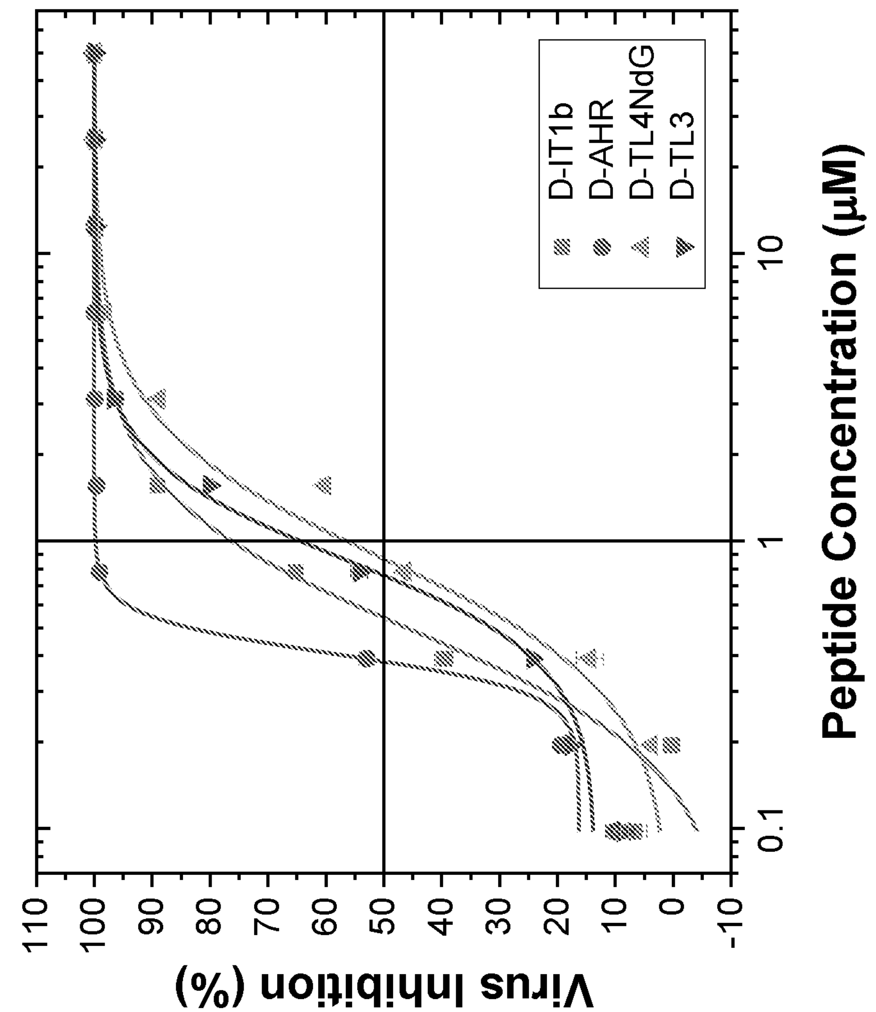
FIG. 7A is a graph showing virus inhibition of Lassa pseudovirus with AVPs composed of D-amino acids. Lassa pseudovirus was incubated with serial dilutions of peptide for 1 hour then added to cells. Infectivity was quantified by measuring luciferase expression translated from the pseudovirus genome approximately 72 hours after infection. Inhibition measurements were fit to nonlinear curves which are shown as solid lines. n=12, mean±SE.
Figure 7B:
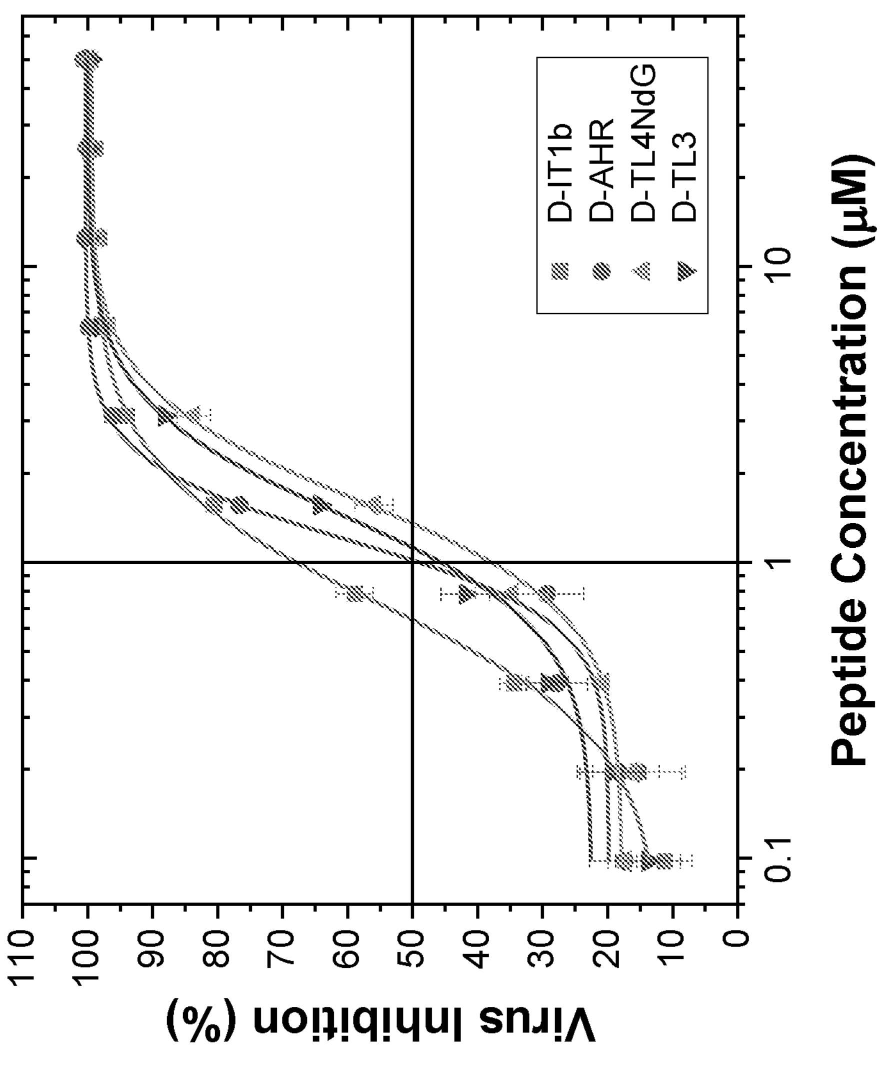
FIG. 7B is a graph showing virus inhibition of SARS-CoV-2 pseudovirus with AVPs composed of D-amino acids. SARS-CoV-2 pseudovirus was incubated with serial dilutions of peptide for 1 hour then added to cells. Infectivity was quantified by measuring luciferase expression translated from the pseudovirus genome approximately 72 hours after infection. Inhibition measurements were fit to nonlinear curves which are shown as solid lines. n=4, mean±SE.

Additionally, the four peptides selected from the test groups were synthesized as D-amino acid versions and tested for virus inhibition of Lassa pseudovirus and SARS-CoV-2 pseudovirus. D-IT1b (SEQ ID NO: 43), D-AHR (SEQ ID NO: 16), D-TL4NdG (SEQ ID NO: 24), and D-TL3 (SEQ ID NO: 3) all demonstrated potent virus inhibition of Lassa pseudovirus (FIG. 7A) and SARS-CoV-2 pseudovirus (FIG. 7B). The Lassa pseudovirus propagation, Lassa pseudovirus neutralization assay, SARS-CoV-2 pseudovirus propagation, and SARS-CoV-2 neutralization assay were performed as described in Example 15.

Figure 2J:
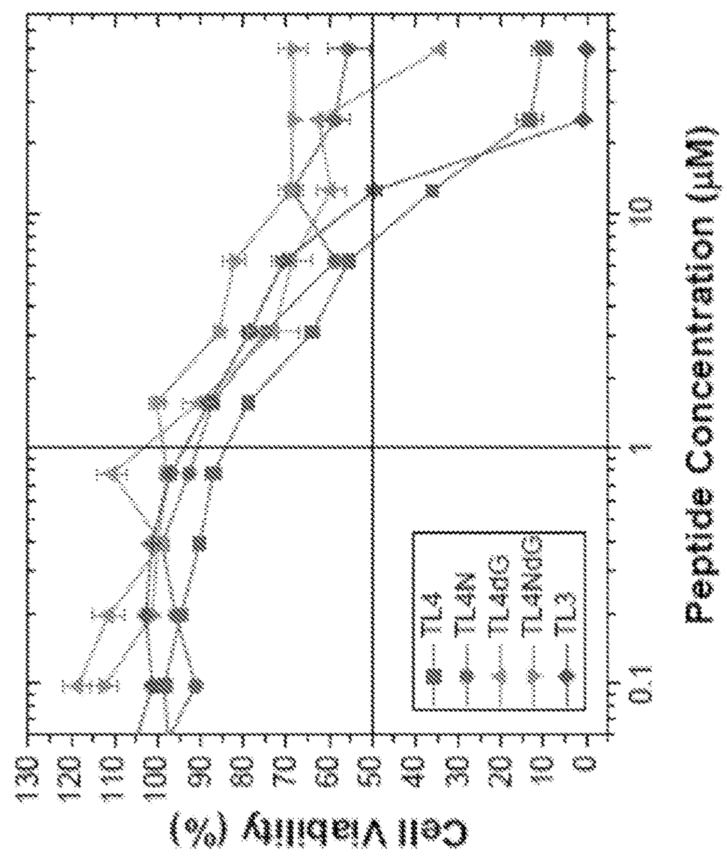
Figure 2L:
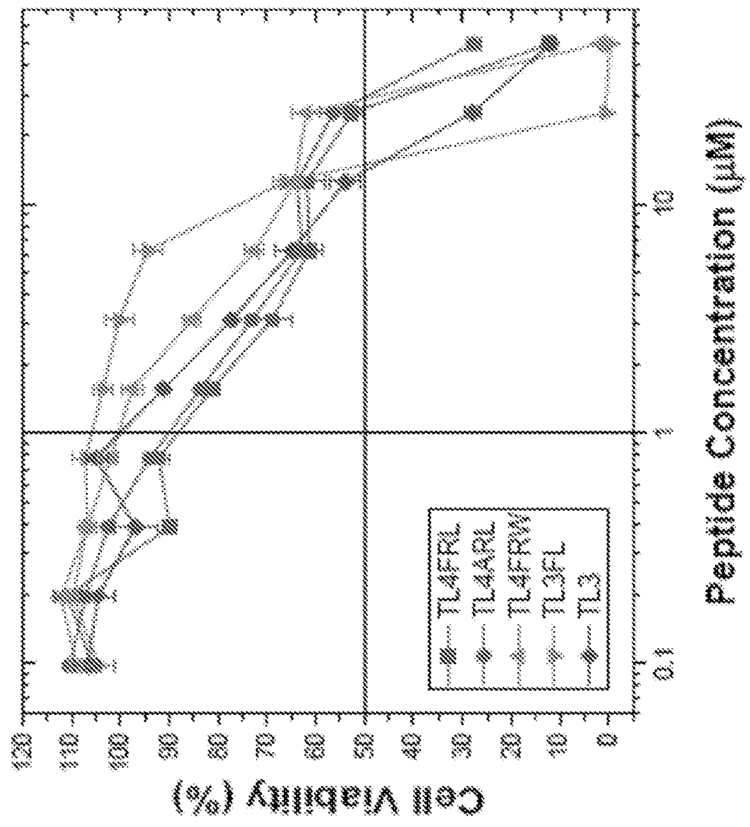
Figure 2K:
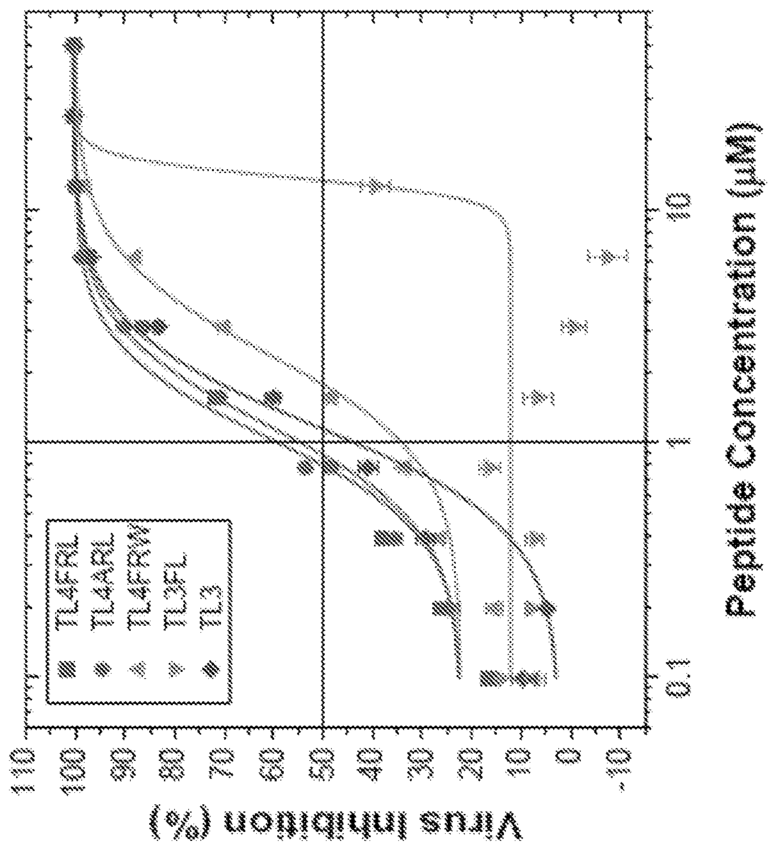

Example 4. Cytotoxicity Assays and Therapeutic Indices of Gain-of-Function AVPs For the cytotoxicity assays, HEK cells were first seeded in 96-well plates in DMEM with 10% FBS at a density of $1\times10^4$ cells/well and were incubated overnight. Peptide was first serially diluted in DMEM. The culture media was then aspirated from the cells and replaced with peptide solutions. After 3 days of incubation at 37° C., 50 μL CELLTITER-GLO® (Promega), prediluted 1:10 in Glo Lysis Buffer (Promega), was added to cells and luminescence was measured using a microplate reader. CCso values were calculated by linear regression constructed from data points directly above and below 50% inhibition. 25 μM MelP5 was used as a negative control for viability, and peptide-free samples were used as a positive control for viability. Cytotoxicity assays reveal that TL4NdG and TL4N are much less cytotoxic than TL3 (FIGS. 21 and 2J). TL4NdG is the least cytotoxic peptide tested. TL4dG is less cytotoxic than TL3 but is slightly more cytotoxic than TL4NdG and TL4N. TL4 has a similar cytotoxicity profile to that of TL3.

When analyzing test peptide screening results (FIG. 23), we found that 17% (4/24) of test peptides have greater antiviral activity than IT1b. All of these peptides were from groups that contain long sequences with multiple hydrophobic regions. 83% (20/24) of test peptides were less toxic than IT1b. All peptides that are more toxic than IT1b have the LLX motif, where X is either arginine or asparagine, seen in TL2. 61% (14/23) of test peptides have a greater therapeutic index than IT1b. Of the four peptides that have greater antiviral activity than IT1b, three have greater therapeutic indices. TL4N had the highest selectivity index at >88.7. The $EC_{50}$ for this peptide is only 5% greater compared to IT1b, while the $CC_{50}$ is over 500% greater than that of IT1b. Also, the sequence of TL4N is 32% shorter than IT1b making TL4N a more cost-effective inhibitor with greater therapeutic potential.

Figure 6:
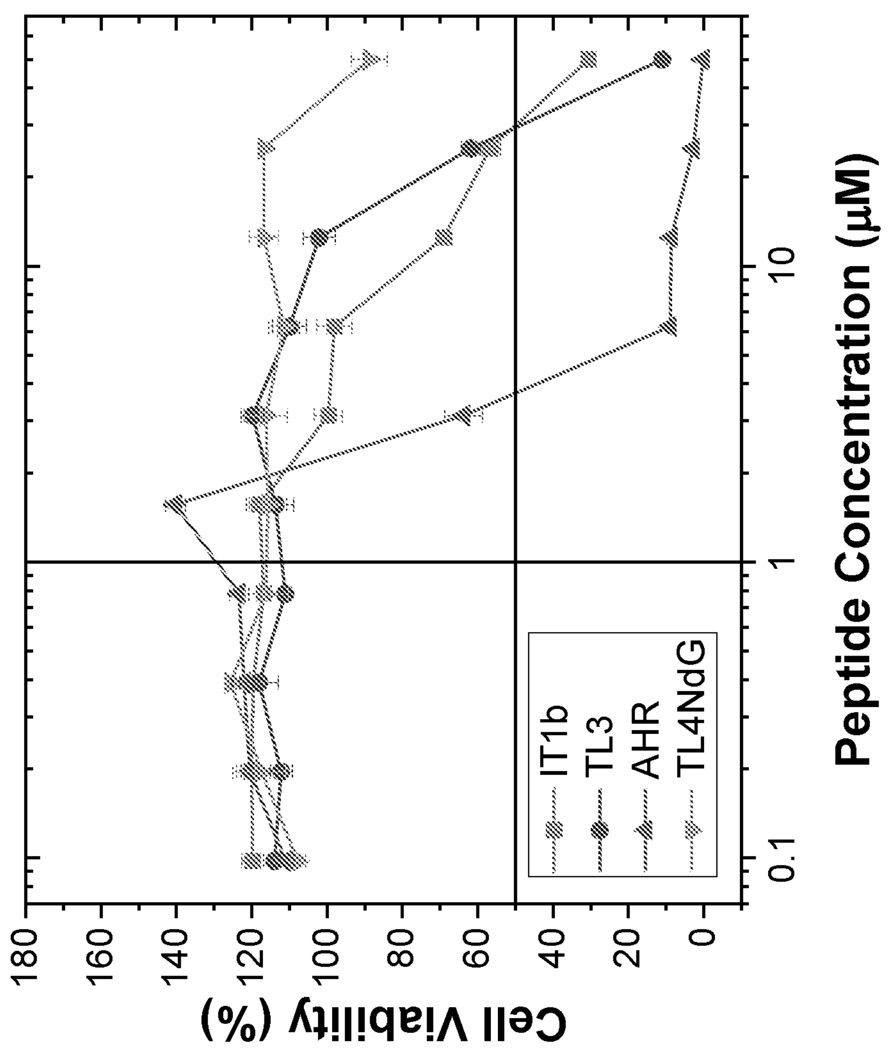
FIG. 6 is a graph showing the cytotoxicity of AVPs against Vero E6 cells. Vero E6 cells were treated with serial dilutions of peptide IT1b, TL3, AHR, or TL4NdG. Percentage cell viability was quantified using CELLTITER-GLO® approximately 72 hours after treatment. n=8, mean±SE.
Figure 7C:
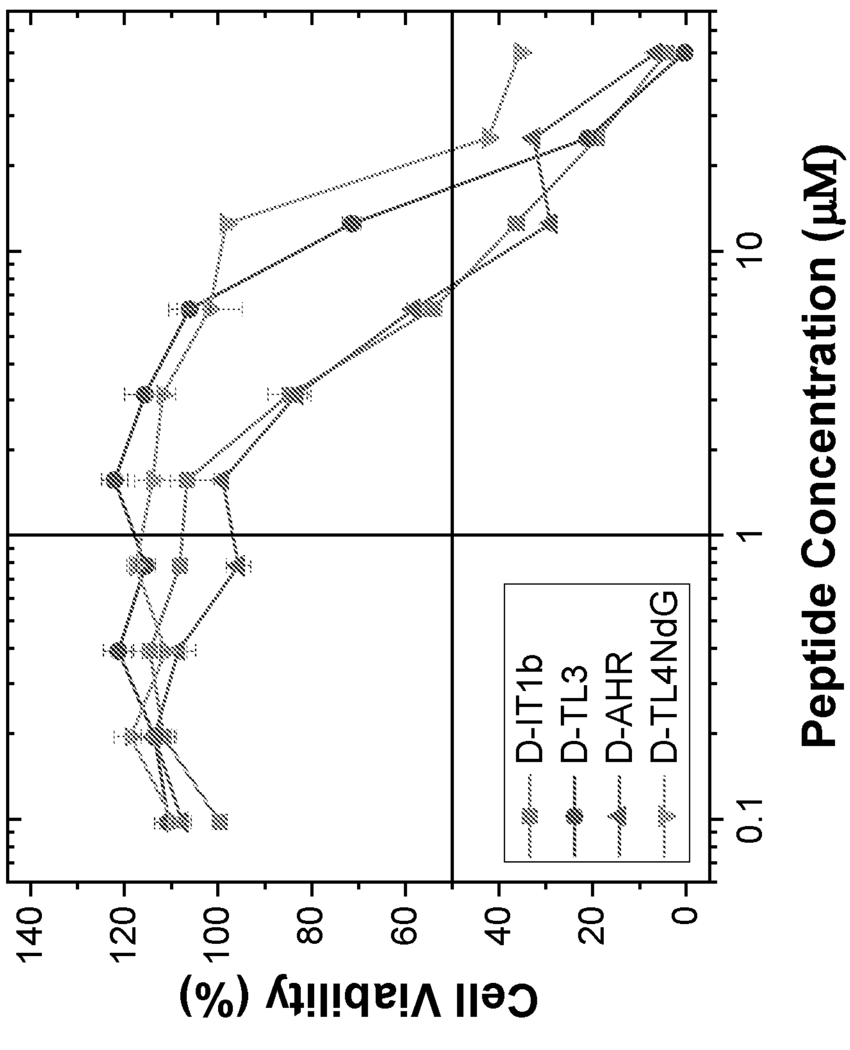
FIG. 7C is a graph showing the cytotoxicity of AVPs composed of D-amino acids against HEK 293T/17 cells. HEK 293T/17 cells were treated with serial dilutions of peptides. Cell viability was quantified using CELLTITER-GLOR approximately 72 hours after treatment. n=12, mean±SE.

The four peptides selected from the test groups were also evaluated using cytotoxicity assays in Vero E6 cells. The cytotoxicity assays in Vero E6 cells were performed using the same methods described above in connection with HEK cells. High cell viability was observed for IT1b, TL3, AHR, and TL4NdG at peptide concentrations at or below 2 μM (FIG. 6). Furthermore, D-amino acid versions were synthesized and tested for cytotoxicity against HEK 293T/17 cells. D-IT1b (SEQ ID NO: 43), D-AHR (SEQ ID NO: 16), D-TL4NdG (SEQ ID NO: 24), and D-TL3 (SEQ ID NO: 3) demonstrated high cell viability at peptide concentrations approximately below 4 μM (FIG. 7C).

Example 5. Serum Stability Analysis

We tested the antiviral activity of the four representative peptides with increasing concentrations of FBS. HEK cells were first seeded in 96-well plates at a density of $1\times10^4$ cells/well in DMEM 10% FBS and were incubated overnight. Lassa pseudovirus was added at a density of $1\times10^3$ $TCID_{50}$/well to serial dilutions of peptide in media with varying concentrations of FBS and incubated for 1 hour. Lassa pseudovirus propagation was performed as described in Example 15. This media was made by mixing 2×MEM with either 0, 20, 50, or 100% FBS in H2O. The culture media was then aspirated from cells and replaced with virus-peptide solutions. Infectivity was quantified by measuring luciferase expression translated from the pseudovirus genome approximately 72 hours after infection using Bright-Glo™ (Promega), prediluted 1:5 in Glo Lysis Buffer (Promega), using a microplate reader. Peptide-free samples were used as a negative control for inhibition, while peptide and virus free samples were used as a positive control for inhibition.

Figure 4A:
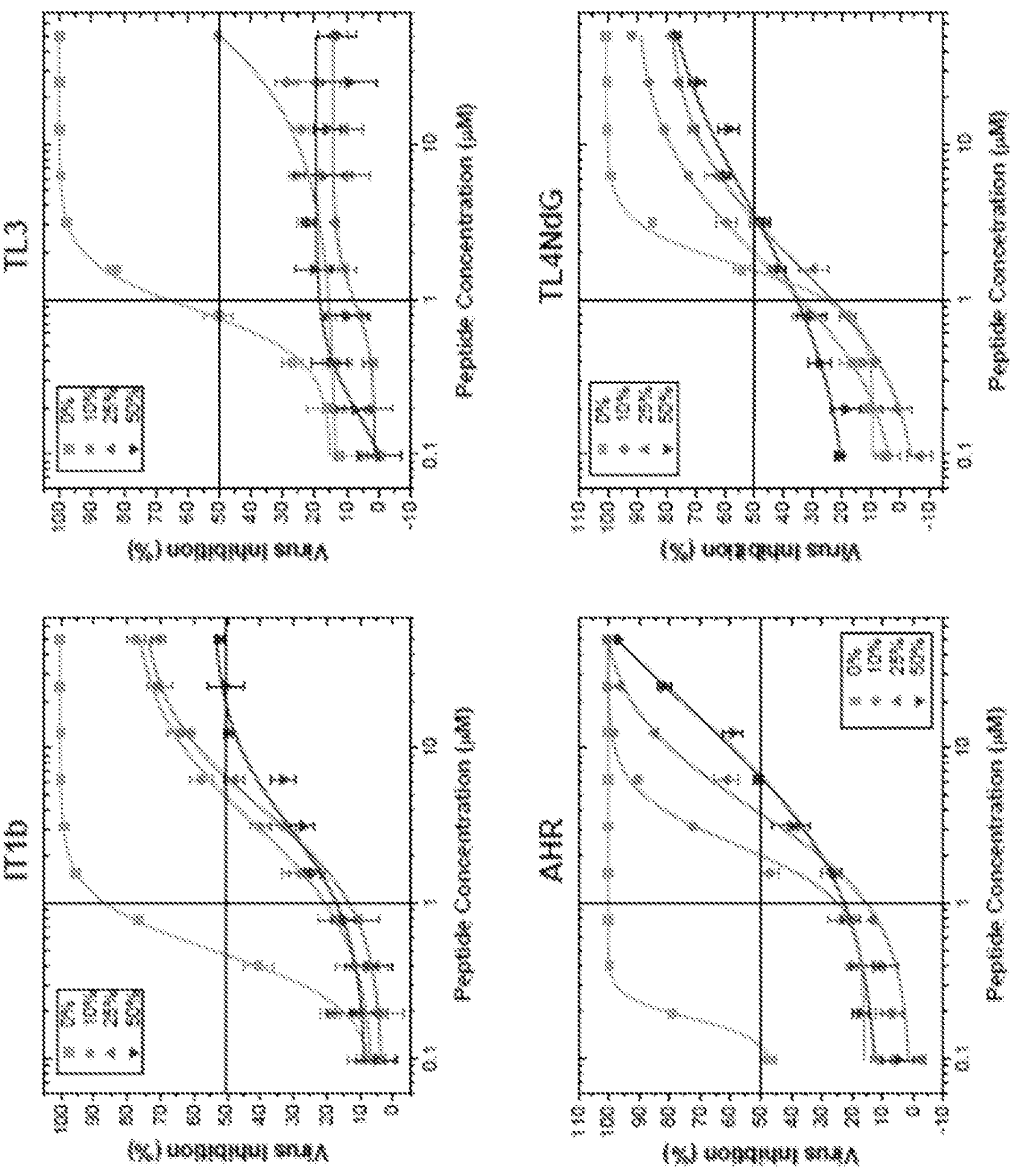
FIG. 4A is a set of graphs showing the percentage of virus inhibition in varying serum concentrations for IT1b, TL3, AHR, and TL4NdG. LASVpv virus was incubated with serial dilutions of peptide for 1 hour in media with the indicated concentrations of FBS then added to HEK cells. Infectivity was quantified by measuring luciferase expression translated from the LASVpv genome approximately 72 hours after infection (n=4, mean±SE). Inhibition measurements were fit to nonlinear curves which are shown here as solid lines. The graph legends represent percent of FBS used in each data series.

Of the four AVPs tested, AHR (SEQ ID NO: 15) retains the most antiviral activity as serum concentration increases (FIG. 4A). In all serum concentrations, inhibition remained at approximately 100% at 50 μM peptide. At 50% FBS, AHR has an $EC_{50}$ of less than 10 μM. Interestingly, TL4NdG (SEQ ID NO: 23) is only minimally affected by serum concentration compared the other peptides. Although the $EC_{50}$ at 0% FBS is the highest for all of the peptides tested, the $EC_{50}$ at 50% FBS is the lowest. Similar to IT1b, 100% inhibition is not observed for TL4NdG in any series with FBS, but greater than 50% inhibition is observed in all FBS concentrations at 50 μM. These results show that AVPs can retain antiviral activity even in the presence of high concentrations of serum.

Figure 11:
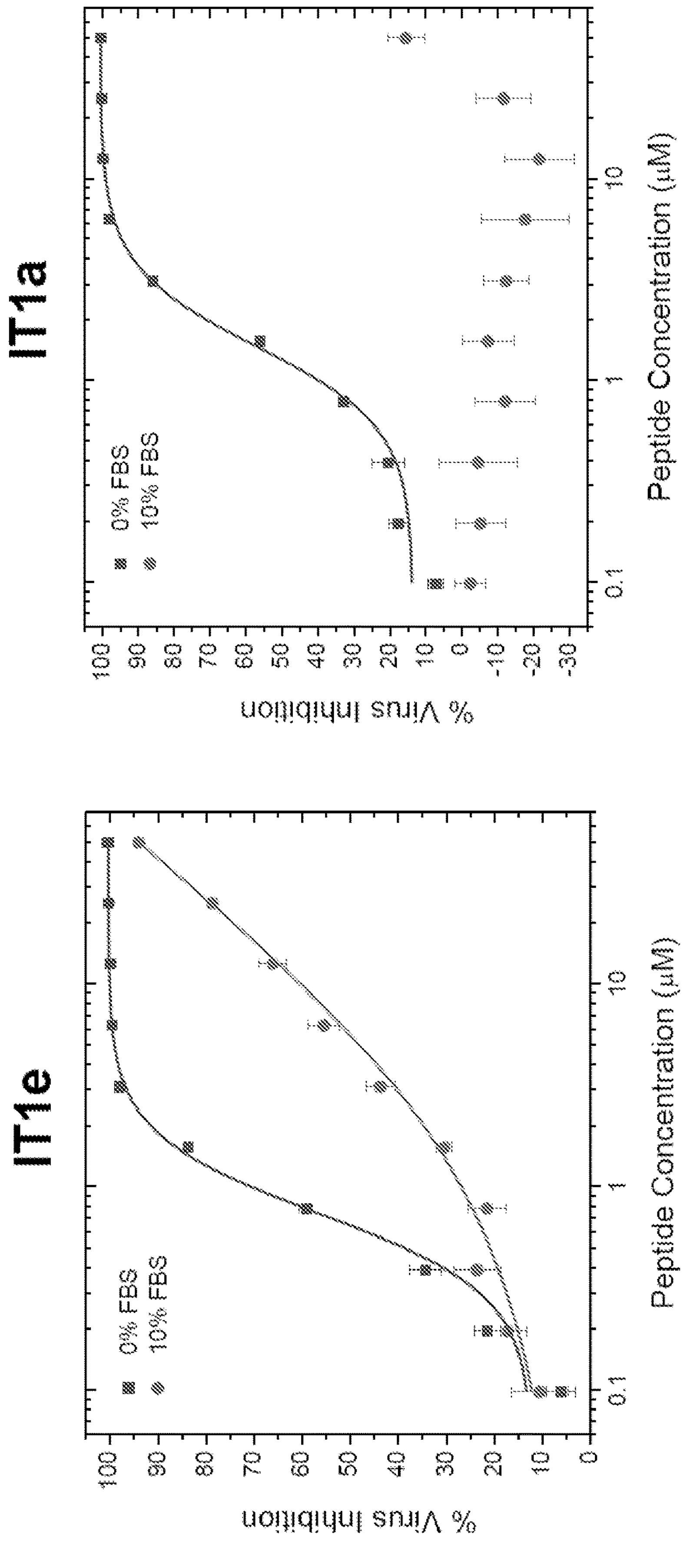
FIG. 11 is a pair of graphs showing the effect of FBS concentration on peptide antiviral activity. Lassa pseudovirus was incubated with varying concentrations of peptide (IT1e or IT1a) for 1 hour using either serum-free media or media with 10% FBS, then added to HEK 293T/17 cells. Infectivity was quantified by measuring luciferase expression translated from the LASVpv genome approximately 72 hours after infection.

For the interfacially active peptides IT1e (SEQ ID NO: 46) and IT1a (SEQ ID NO: 41), the effect of FBS concentration on peptide antiviral activity was observed. LASVpv was incubated with varying concentrations of peptide for 1 hour using either serum free media or media with 10% FBS, then added to cells. Infectivity was quantified by measuring luciferase expression translated from the LASVpv genome approximately 72 hours after infection. For both IT1e and IT1a (FIG. 11), we found reduced antiviral activity in the presence of 10% FBS.

For cytotoxicity assays, HEK cells were first seeded in 96-well plates in DMEM 10% FBS at a density of $1\times10^4$ cells/well and were incubated overnight. Peptide was first serial diluted in media with varying concentrations of FBS. This media was made by mixing 2×MEM with either 0, 20, 50, or 100% FBS in $H_2O$. The culture media was then aspirated from cells and replaced with peptide solutions. After 3 days of incubation at 37° C., 50 μL CELLTITER-GLO® (Promega), prediluted 1:10 in Glo Lysis Buffer (Promega), was added to cells and luminescence was measured using a microplate reader. 25 μM MelP5 was used as a negative control for viability, and peptide free samples were used as a positive control for viability.

Figure 4B:
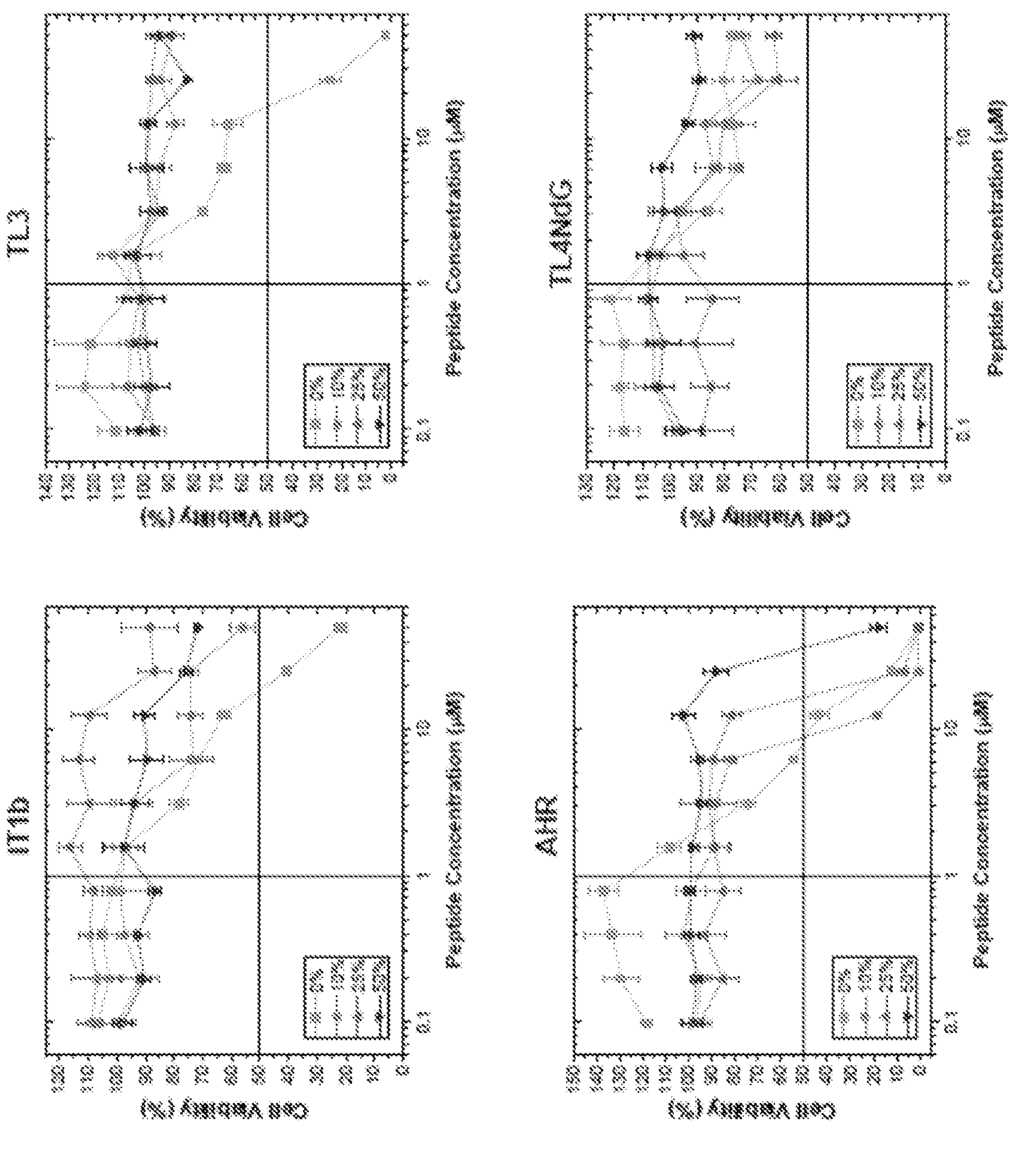
FIG. 4B is a set of graphs showing the percentage of cell viability in varying serum concentrations for IT1b, TL3, AHR, and TL4NdG. HEK cells were treated with serial dilutions of peptide in media containing varying concentrations of FBS. Cell viability was quantified using CELLTITER-GLO® approximately 72 hours after treatment (n=4, mean±SE). The graph legends represent percent of FBS used in each data series.

To complement the inhibition measurements with varying serum concentrations, we measured the cytotoxicity of each representative peptide under these serum conditions (FIG. 4B). IT1b becomes far less cytotoxic as serum concentration increases. TL3 is completely noncytotoxic in 10%, 25%, and 50% FBS, but does display cytotoxicity in 0% FBS. AHR is cytotoxic in all serum concentrations at high peptide concentrations, though cytotoxicity steadily diminishes as serum concentration increases. TL4NdG cytotoxicity is essentially unchanged by serum concentration. Cytotoxicity trends generally follow virus inhibition trends which indicates that peptides are non-specifically binding serum components.

Example 6. Cell Density Analysis with Gain-of-Function AVPs

Figure 5A:
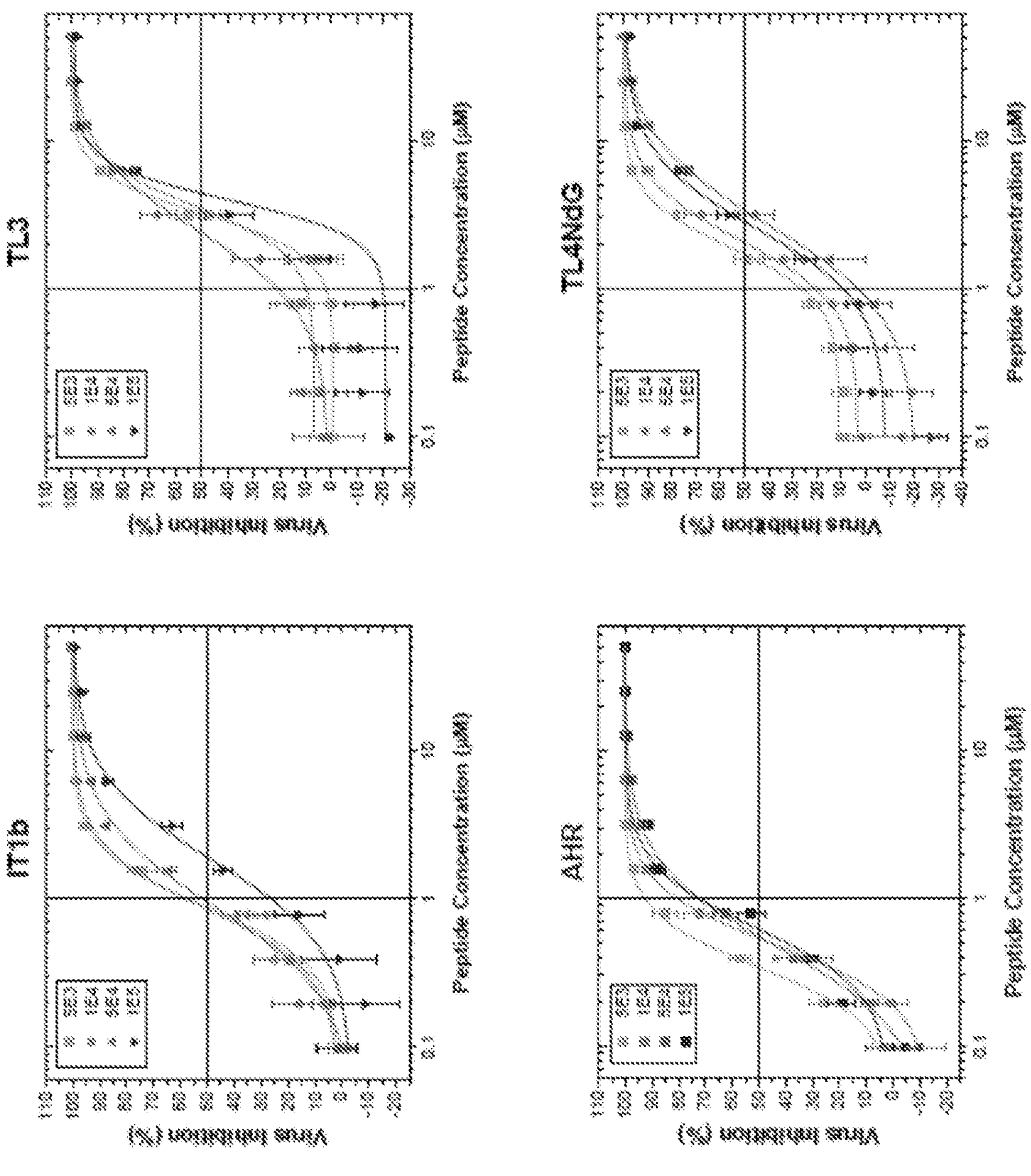
FIG. 5A is a set of graphs showing the percentage of virus inhibition with varying cell densities for IT1b, TL3, AHR, and TL4NdG. HEK cells were plated at varying cell densities and incubated overnight. Serial dilutions of peptide were added to cells for 1 hour followed by the addition of virus. Infectivity was quantified by measuring luciferase expression translated from the LASVpv genome approximately 72 hours after infection (n=4, mean±SE). Inhibition measurements were fit to nonlinear curves which are shown here as solid lines. Cell densities are expressed in E notation ($AEB=A\times10^{8}$) in units of cells/well.

To understand the level of specificity to which peptides preferentially bind and inhibit virus, we performed virus inhibition assays with varying cell densities. For the inhibition assays, HEK cells were first seeded in 96-well plates at a density of either $5\times10^3$, $1\times10^4$, $5\times10^4$, or $1\times10^5$ cells/well in DMEM 10% FBS and were incubated overnight. The culture media was then aspirated from the cells and replaced with serial dilutions of peptide in DMEM and incubated for 1 hour. Lassa pseudovirus was then added to cells at a density of $1\times10^3$ TCIDso/well in DMEM. Lassa pseudovirus propagation was performed as described in Example 15. Infectivity was quantified by measuring luciferase expression translated from the pseudovirus genome approximately 72 hours after infection using Bright-Glo™ (Promega), prediluted 1:5 in Glo Lysis Buffer (Promega), using a microplate reader. Peptide free samples were used as a negative control for inhibition, while peptide and virus free samples were used as a positive control for inhibition. We found that, in general, AVP peptide antiviral activity is unaffected by cell density (FIG. 5A). Inhibition curves remained relatively unchanged despite large increases in cell concentrations.

Figure 5B:
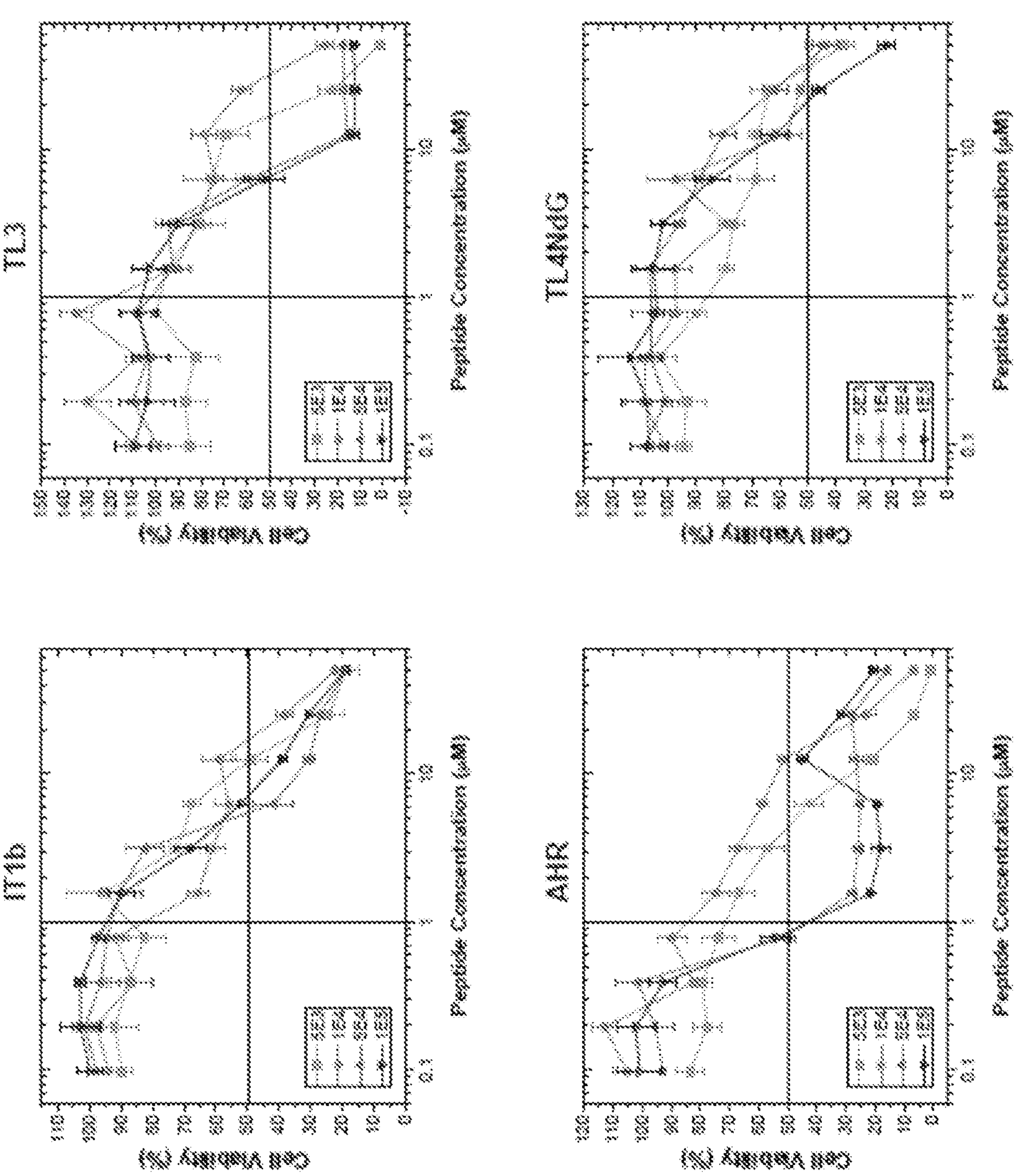
FIG. 5B is a set of graphs showing the percentage of cell viability in varying cell densities for IT1b, TL3, AHR, and TL4NdG. HEK cells were plated at varying cell densities and incubated overnight. Cells were then treated with serial dilutions of peptide. Viability was quantified using CELL-TITER-GLOR approximately 72 hours after treatment (n=4, mean±SE).

For the cytotoxicity assays, HEK cells were first seeded in 96 well plates in DMEM 10% FBS at a density of either $5\times10^3$, $1\times10^4$, $5\times10^4$, or $1\times10^5$ cells/well and were incubated overnight. Peptide was first serial diluted in DMEM. The culture media was then aspirated from the cells and replaced with peptide solutions. After 3 days of incubation at 37° C., 50 μL CELLTITER-GLO® (Promega), prediluted 1:10 in Glo Lysis Buffer (Promega), was added to cells and luminescence was measured using a microplate reader. 25 μM MelP5 was used as a negative control for viability, and peptide free samples were used as a positive control for viability. IT1b and TL4NdG cytotoxicity remained consistent as cell density increases, while TL3 and AHR cytotoxicity increases as cell density increases (FIG. 5B).

Example 7. Viral Infection Analysis with Interfacially Active AVPs

We tested three families of peptides (Table 3) that were selected from previous high-throughput screens for antiviral activity against Lassa pseudovirus (LASVpv). These peptides were selected from library screen positives due to having membrane activity in synthetic vesicles or sterilizing activity against bacteria by membrane permeabilization (SEQ ID NOs: 30-42, 44-47). A control group was also tested that contained peptides that possess a variety of attributes that differ from the library peptides, such as negative charge, alpha helical secondary structure, and the ability to spontaneously translocate membranes (SEQ ID NOs: 48-51, 53). None of the peptides tested here were known to have antiviral activity previous to this work.

The Lassa pseudovirus is constructed from two plasmids: pNL4-3.Luc.R-.E-(NL4) and Lassa glycoprotein precursor (GPC) plasmid. The Lassa GPC plasmid is constructed from pcDNA3.1 (+) with CMV intron A, upstream of the Lassa GPC gene, to aid in Lassa glycoprotein expression (Illick et al. (2008) *Viral. J.* 5:161). NL4 contains the HIV-1 genome with defective Net, Env, and Vpr genes (He et al. (1995) *J. Viral.* 69 (11): 6705-6711; Connor et al. (1995) *Virology.* 206(2):935-944), which causes the progeny pseudovirus to be replication incompetent. NL4 plasmid also contains a luciferase reporter gene, providing this pseudovirus system with accurate and sensitive measurement of infection. Cotransfection of these two plasmids with lipofectamine in HEK 293T/17 cells yields LASVpv. Due to lack of a glycoprotein gene in the progeny virus, LASVpv can only undergo one round of replication. This pseudovirus system allows quantification of viral entry inhibition.

TABLE 3

| Name | Sequence | SEQ ID NO: | N | Charge | WWIHS | SS | Membrane Activity PC Bilayer | Membrane Activity Bacteria | Membrane Activity RBCs |
|---|---|---|---|---|---|---|---|---|---|
| Vesicle-selected (VS) Membrane Permeabilizing Peptides | | | | | | | None (N), Low (L), Medium (M), High (H) | | |
| *VDVY* | RRGWVLDLVLYYGRR | 30 | 15 | +4 | −3.0 | β | M | H | H |
| *ARVA | RRGWALRLVLAY | 31 | 12 | +4 | −3.8 | β | M | H | M |
| *arva | rrgwalrlvlay | 32 | 12 | +4 | −3.8 | β | M | H | M |
| ARYV | WALRLYLGVY | 33 | 9 | +2 | −6.5 | β | M | H | M |
| VVRG | WVLVLRLGY | 34 | 9 | +2 | −5.7 | β | M | H | H |
| Biologically Selected (BS) Antimicrobial Peptides (BS) | | | | | | | | | |
| *NRRV* | RRGWNLRLRLVYGER | 35 | 15 | +7 | −1.3 | β | L | H | M |
| *ARNY* | RRGWALRLNLYYGRR | 36 | 15 | +7 | −2.9 | β | L | H | H |
| *GRVY* | RRGWRLNLNLYYGRR | 37 | 15 | +7 | −3.4 | β | M | H | H |
| *RNNY* | RRGWRLNLNLYYGRR | 38 | 15 | +6 | −2.7 | β | L | H | H |
| *TNTN* | RRGWTLNLTLNYGRR | 39 | 15 | +5 | −2.7 | β | L | H | M |
| *NATT* | RRGWNLALTLTYGRR | 40 | 15 | +5 | −2.5 | β | L | H | M |
| Synthetically Evolved, 2nd Iteration (It) Pore-forming Peptides | | | | | | | | | |
| ITI-a | RRGFSLKLLLSYRGWALLRLGYGRR | 41 | 15 | +8 | −4.6 | β | H | H | M |
| ITI-b | RRGFSLKLALLKDGWLLLRLGYGRR | 42 | 15 | +8 | −3.0 | β | H | H | M |
| ITI-c | RRGFSLKLALLYRSWLLLLRLGYGRR | 44 | 15 | +8 | −5.9 | β | H | M | M |
| ITI-d | RRGFSLKLRLLYRGWGLALRLGYGRR | 45 | 15 | +9 | −3.9 | β | H | H | H |
| ITI-e | RRGFSLKLKLLYRGWALALRLGYGRR | 46 | 15 | +9 | −3.6 | β | H | H | H |
| ITI-f | RRGFSLKLALLKDGWLLLLRLGYGRR | 47 | 15 | +7 | −3.5 | β | H | H | M |
| Miscellaneous and Control Peptides | | | | | | | | | |
| TP2 | PLIYLRLLRGQF | 49 | 12 | +3 | −4.1 | rC | N | L | L |
| Arg9 | RRRRRRRRRWC | 51 | 11 | +10 | +3.0 | rC | L | L | L |
| Mel-L16G | GIGAVLKVLTTGLPAGISWIKRKRQQ | 50 | 26 | +6 | +0.5 | α | L | H | L |
| MelN4 | GIGAVLKGLATGLPAGISWIKQQAQL | 52 | 26 | +3 | −2.0 | α | L | L | L |
| Mellttin | GIGAVLKVLTTGLPALISWIKRKRQQ | 53 | 26 | +6 | −8.3 | α | H | H | H |

Figure 8:
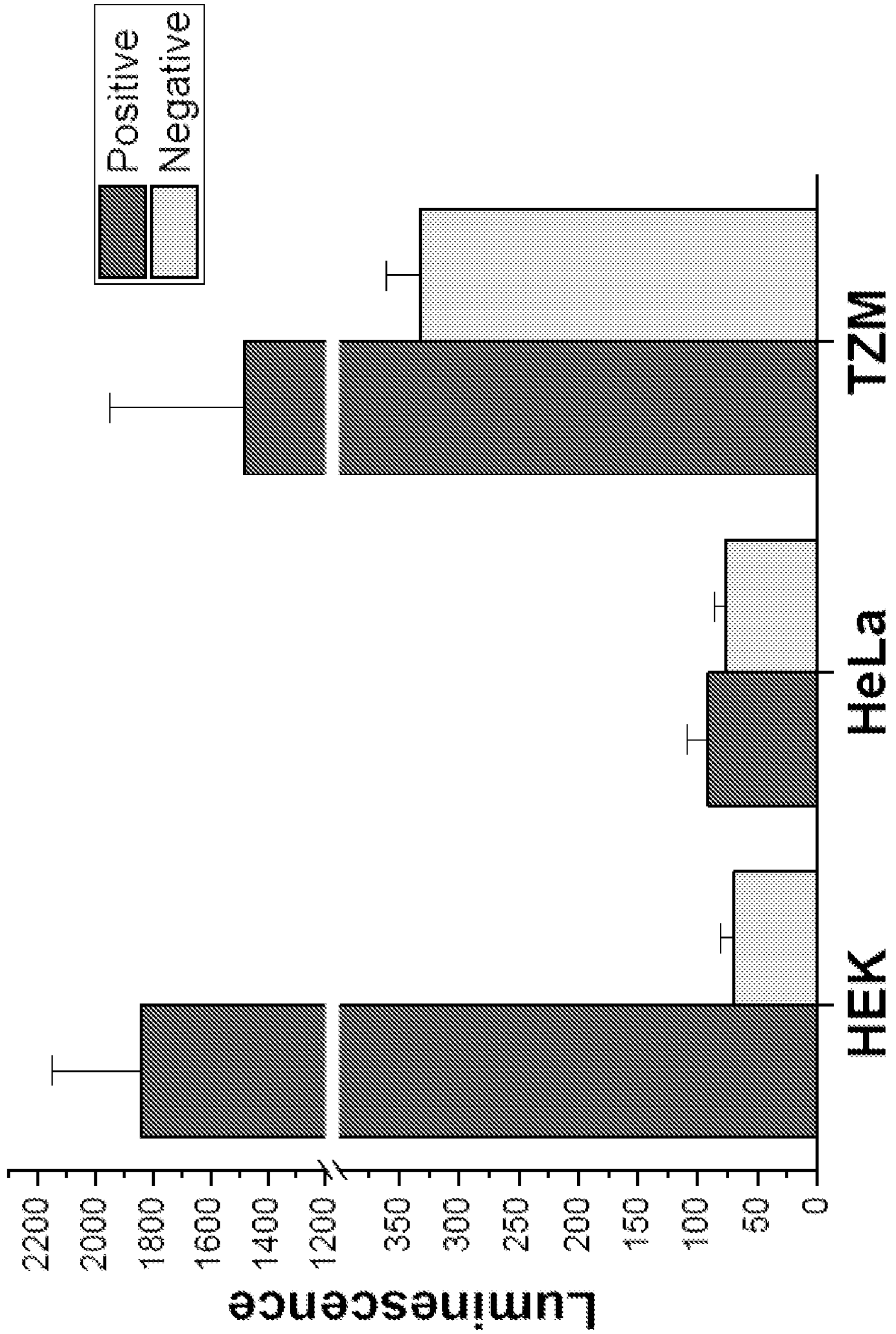
FIG. 8 is a graph showing Lassa pseudovirus luciferase expression in multiple cell lines. Various cell lines were infected with LASVpv (Positive) or media (Negative). Luciferase expression (Positive) translated from the pseudovirus genome, and background levels (Negative) were measured approximately 72 hours after infection (n=4, mean±SD).
Figure 9B:
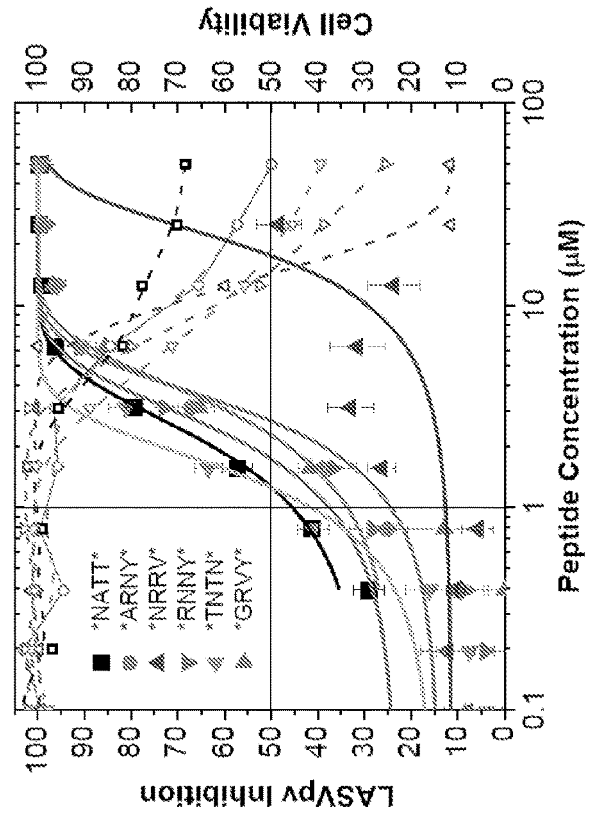
FIGS. 9A-9D are graphs showing virus inhibition of Lassa pseudovirus with AVPs and cytotoxicity of AVPs. Virus was incubated with varying concentrations of peptide for 1 hour then added to cells. Infectivity was quantified by measuring luciferase expression translated from the LASVpv genome approximately 72 hours after infection. Cells were also treated with peptide alone and percentage of cell viability was determined by ALAMARBLUE™ approximately 72 hours after treatment. Infectivity is shown as solid points and respective nonlinear curve fits are shown as solid lines. Cell viability is shown as empty points with dashed lines. Peptide families tested were IT (FIG. 9A), BS (FIG. 9B), VS (FIG. 9C), as well as miscellaneous and control peptides (FIG. 9D) (n=4-8, mean±SE).
Figure 9A:
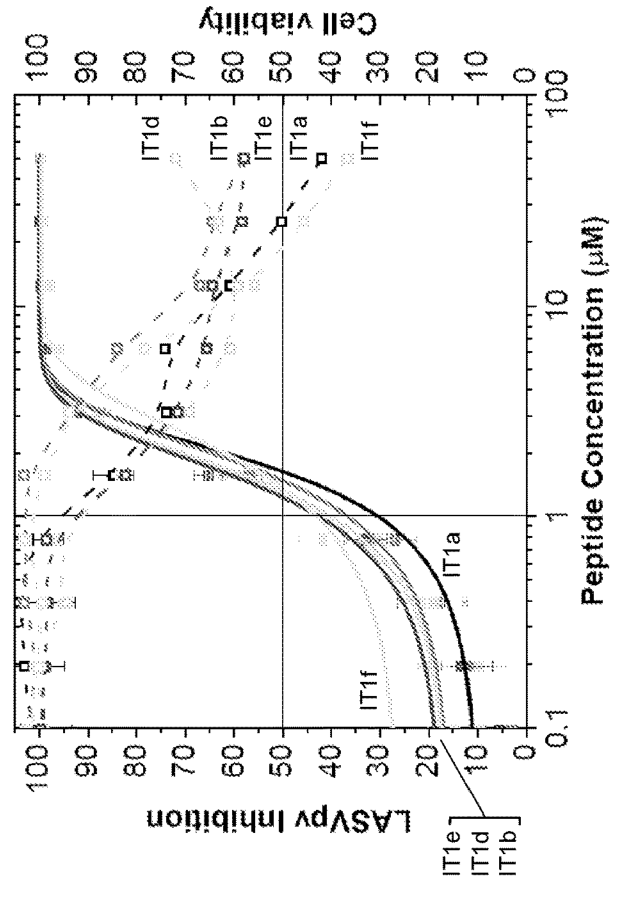
Figure 9C:
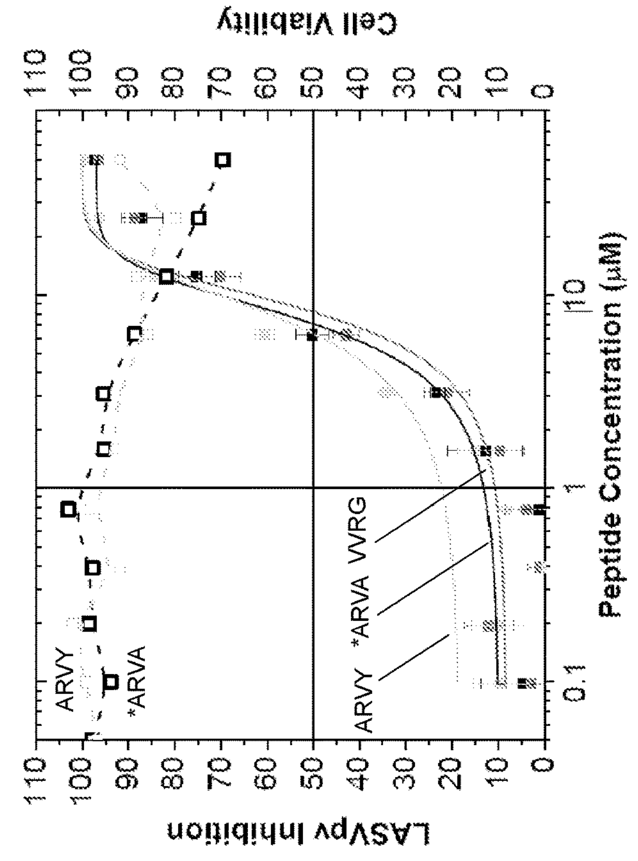
Figure 9D:
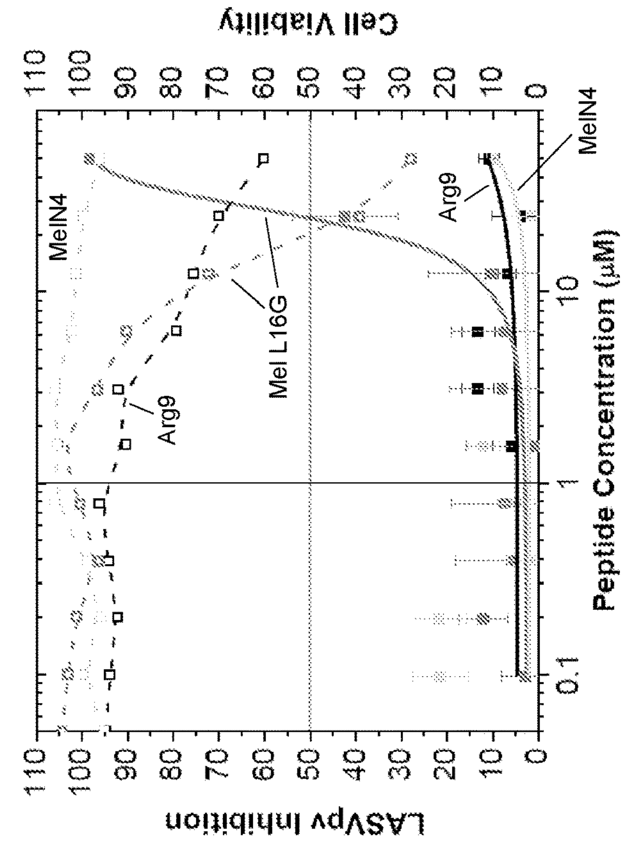

To screen for inhibition, we added LASVpv, at 1000× TCID50, to a serial dilution of peptides, incubated this solution for 1 hour, then added to HEK cells (FIG. 8). Lassa pseudovirus propagation was performed as described in Example 15. 72 hours after infection, cells were lysed and luciferase expression was measured using Bright-Gia™, a luciferin reagent. Luminescence from luciferase was measured in a microplate reader. We calculated percent inhibition by comparing analyte values to positive and negative control luminescence values. The positive control consisted of cells and virus and excluded peptide. The negative control consisted of cells and excluded virus and peptide. Four parameter logistic curves were fit to inhibition values to analyze the data. We found that all interfacially active peptides cause inhibition of LASVpv. 13 of the 14 peptides tested have an $EC_{50}$ between 1 and 10 μM (FIGS. 9A-9D). The miscellaneous peptides Arg9 and MeIN4 show little to no activity. MeII16G is inhibitory but was much less active than a large majority of the interfacially active peptides.

Example 8. Broad-spectrum Viral Inhibition Using Interfacially Active AVPs

To test the antiviral activity of these peptides on a replication-competent virus, we performed influenza inhibition assays. The influenza virus inhibition assay was performed as described in Example 15. This cell-culture based assay measures cytopathic effects (CPE) from the virus by fixing and staining an infected cell monolayer with DAPI. Infected cells are destroyed and washed away during the fixation, while live cells, which are still attached to the plate, will incorporate the fluorescent dye. H3N2 influenza virus, at 50×TCID50, was incubated with serial diluted peptide for 1 hour, then added to MDCK cells. This cell line was chosen because of the well-established use in the literature due to its high susceptibility to influenza virus infection (Ilyushina et al. (2012) *J. Viral.* 86(21):11725-11734). Approximately 48 hours after infection, cells were fixed and stained. DAPI fluorescence was measured in a microplate reader to quantify CPE.

Figure 12A:
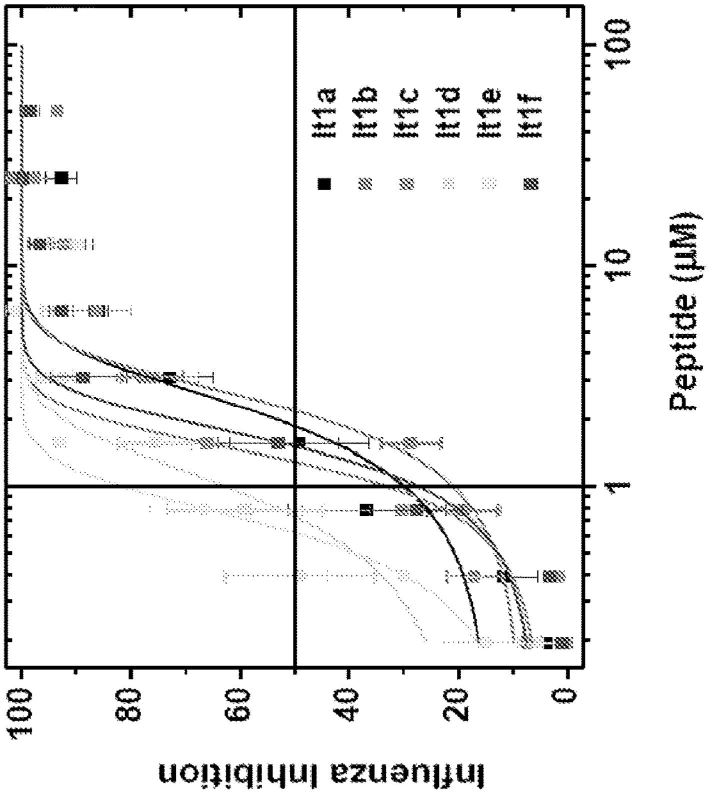
FIGS. 12A-12D are graphs showing influenza virus inhibition with AVPs. H3N2 influenza virus inhibition was measured for the IT family of peptides (FIG. 12A), the biologically selected (BS) family of peptides (FIG. 12B), the vesicle-selected (VS) family of peptides (FIG. 12C), and a set of control peptides (FIG. 12D). Buffer mock infection was used as a negative inhibition control (Mock), and a 1/50,000 dilution of a human convalescent antibody was used as a positive inhibition control (Antibody). Virus was incubated in 96-well plates with serially diluted peptide for 30 minutes and was then added to cell monolayers at 50×TCIDso for 1 hour. After 48 hours at 37° C. the supernatants were removed, the plates were then washed, fixed with 4% paraformaldehyde, and stained with DAPI. DAPI fluorescence enables the measurement of the number of intact cells remaining in the well that did not succumb to viral cytopathic effects.
Figure 12B:
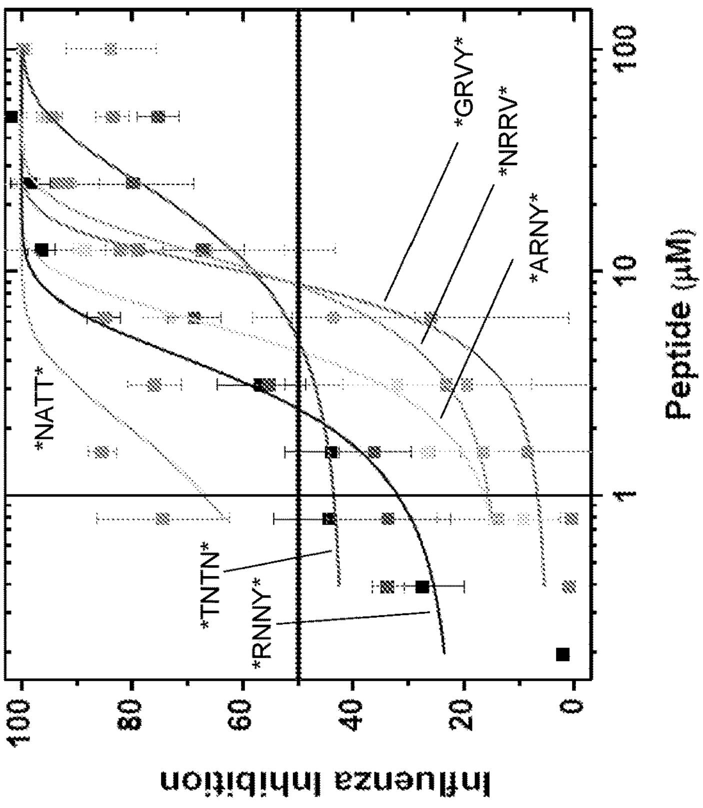
Figure 12D:
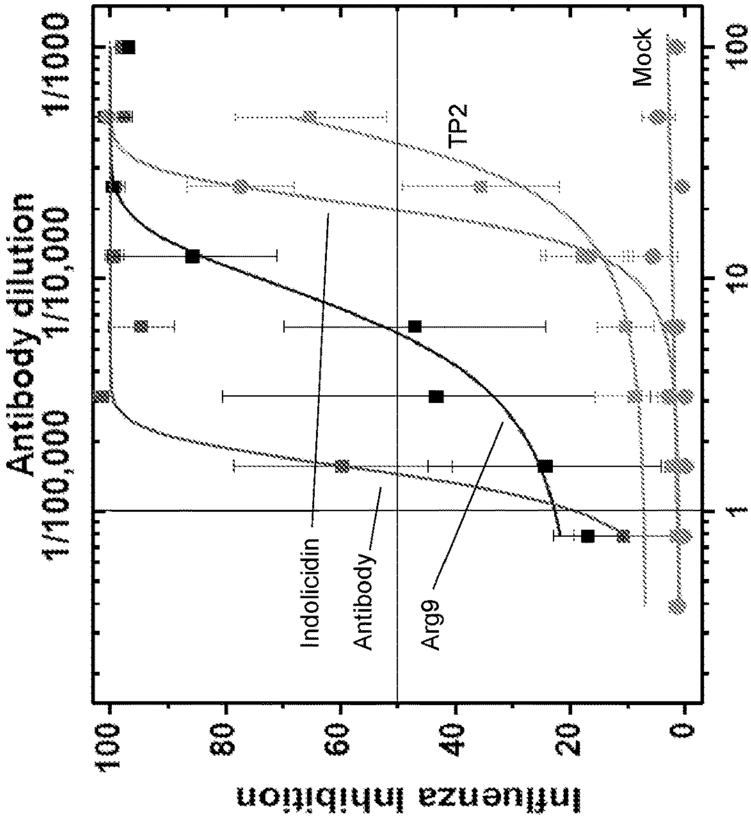
Figure 12C:
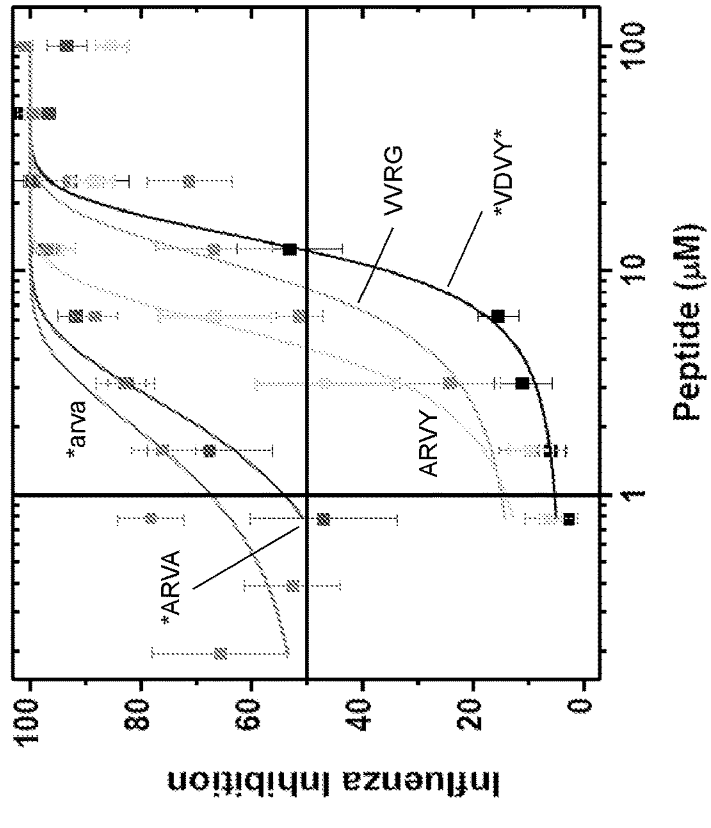

Untreated virus completely destroys the cell monolayer while virus treated with a human convalescent antibody (diluted 1/50,000) is neutralized. All interfacially active peptides inhibit H3N2 with ECso values ranging from 20 μM to ≤1 μM (FIGS. 12A-12C). Cell monolayers remain intact at high peptide concentrations for most cases, suggesting minimal cytotoxicity in this concentration range. Interestingly, Arg9 has significant activity against H3N2 (FIG. 12D) but no activity against LASVpv. TP2 has some antiviral activity against H3N2 but is less potent than the interfacially active peptides. We have shown that interfacially active peptides are able to inhibit LASVpv and influenza virus and, thus, could be used as broad-spectrum antiviral therapeutics.

To determine the broad-spectrum activity of the interfacially active peptides, broad-spectrum antiviral activity against dengue virus (DENV), herpes simplex virus (HSV), and adenovirus (AdV). We used plaque assays to determine peptide antiviral activity against each virus. To perform the assay, cell monolayers are first infected with virus. A semi-solid overlay is then added on top of the monolayer to prevent the spread of virus to non-neighboring cells. After a specific incubation time, which varies by virus, the overlay is removed, and cells are fixed and stained. Plaques are identified as distinct zones of the monolayer that have been cleared. Commonly, viral titers are reported as plaque forming units per milliliter (PFU/ml). Plaque assays were performed as described in Example 15.

Figure 13A:
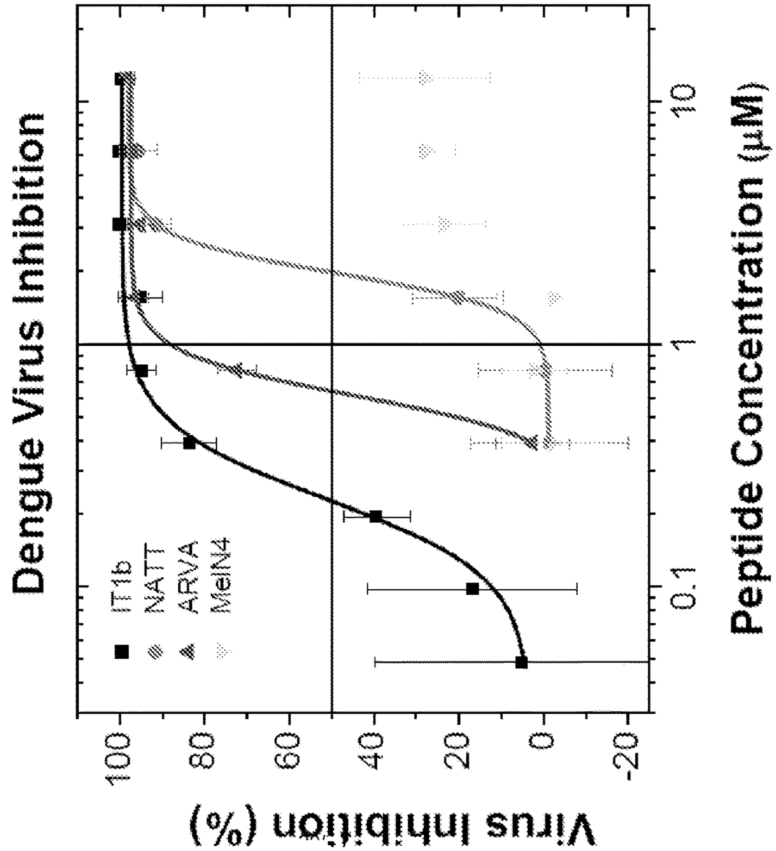
FIGS. 13A-13C are graphs showing virus inhibition of dengue virus, herpes simplex virus, and adenovirus with AVPs. Peptides were tested against dengue virus type 2 (FIG. 13A), herpes simplex virus type 1 (FIG. 13B), and human adenovirus 5 (FIG. 13C) (n=6, mean±SE). Plaque assays were used to quantify infectivity. From each family, representative peptides at varying concentrations and virus were incubated for 1 hour. The inoculum was then transferred to VERO E6 cells for 1 hour, then was washed from the cells. AVICEL® overlay was added to the cells and then incubated until viral plaques were visible by crystal violet staining.
Figure 13B:
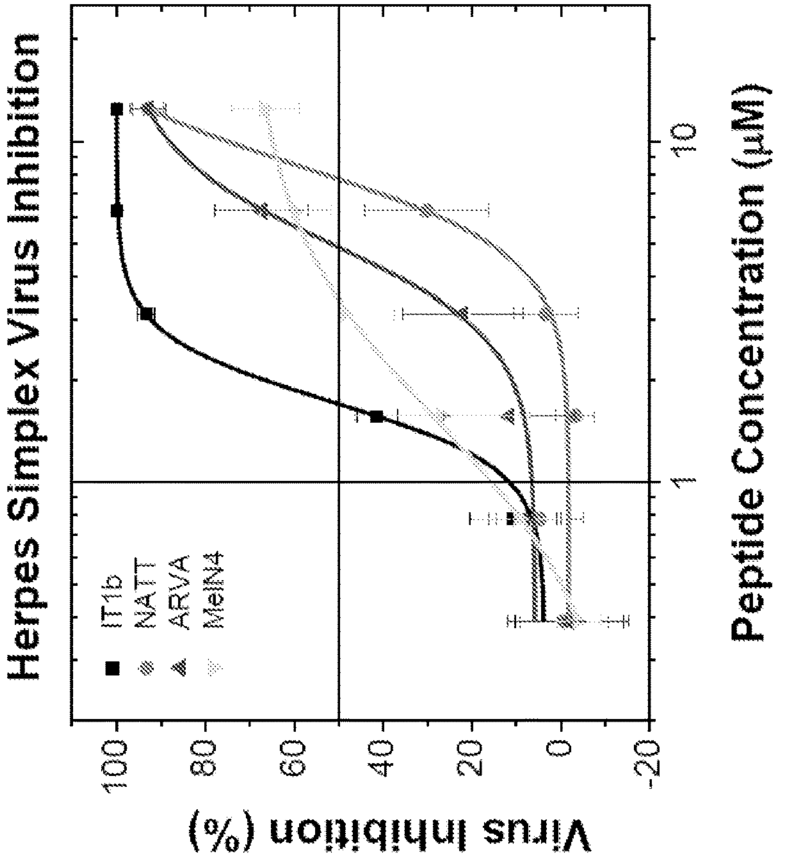
Figure 13C:
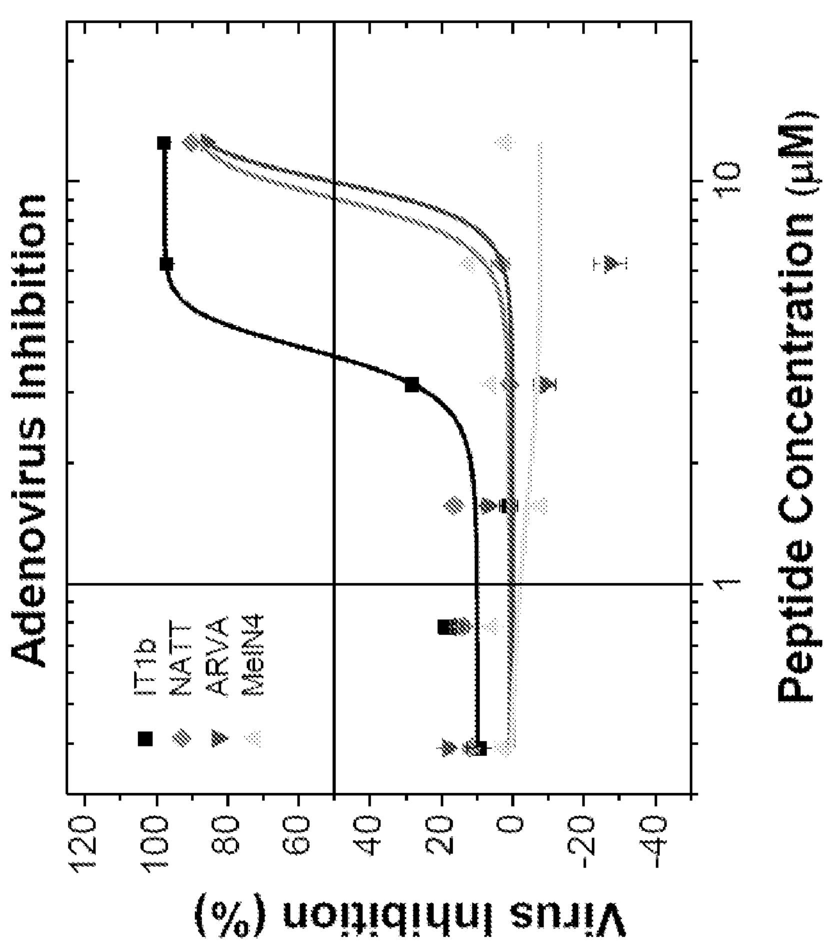

For these experiments, we used a representative set of peptides. IT1b from the IT family, ARVA from the VS family, NATT from the BS family, and MeIN4 from the control family. These were chosen as representatives based on inhibition and cytotoxicity profiles. DENV inhibition challenges reveal that all interfacially active peptides cause significant inhibition. In fact, these peptides are more active against DENV than any other virus tested (FIG. 13A). MeIN4 shows little activity against this virus. HSV-1 challenges (FIG. 13B) reveal antiviral activity profiles similar to those seen in influenza challenges. Interestingly, when challenging adenovirus, we found that all peptides, except MeIN4, inhibit the nonenveloped virus (FIG. 13C). The activity is much lower than that seen with other enveloped viruses. This finding shows that interfacially active peptides could be interacting with multiple components of the virus, and that inhibition is not limited to envelope destabilization.

Example 9. Cytotoxicity Assays with Interfacially Active AVPs

Figure 10A:
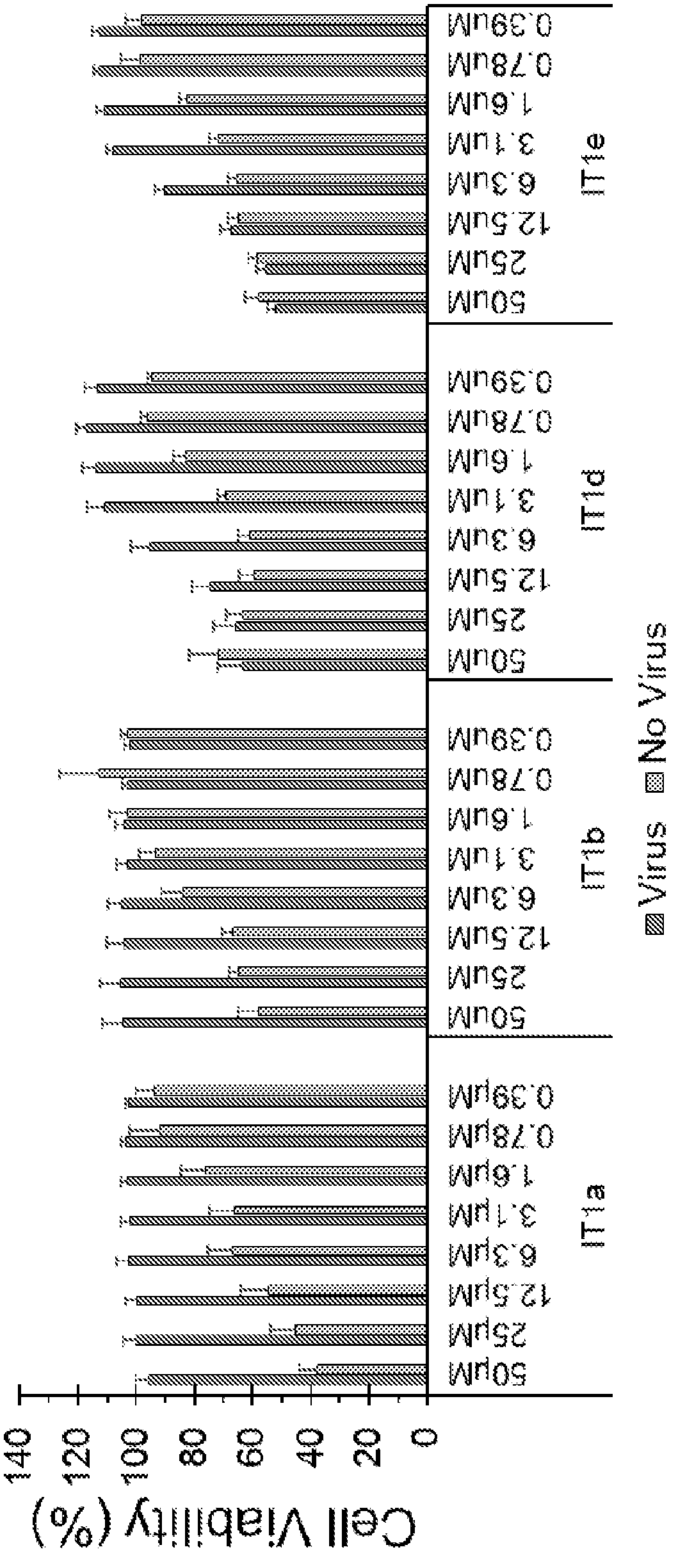
FIGS. 10A-10D are graphs showing viability of AVP-treated cells in the presence and absence of LASVpv. Peptide was added to cells at various concentrations. In half the samples, virus was added along with peptide, while the other half received a virus-free peptide treatment (data from FIGS. 9A-9D dotted lines). Selected peptides from IT (FIG. 10A), BS (FIG. 10B), VS (FIG. 10C) families were tested, as well as miscellaneous and control peptides (FIG. 10D). Cell viability was determined by ALAMARBLUE™ approximately 72 hours after treatment (n=4-8, mean±SE).
Figure 10B:
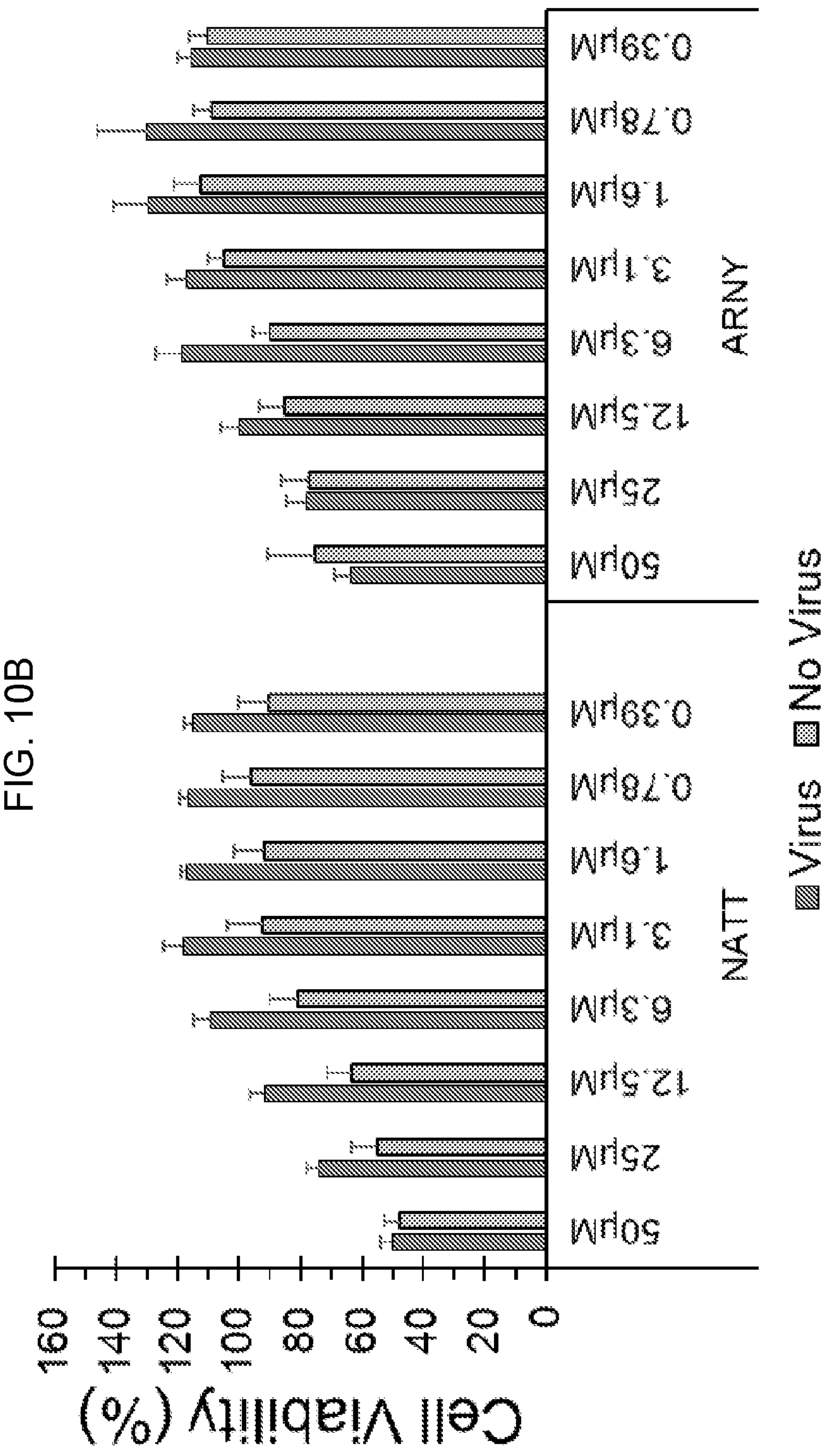
Figure 10C:
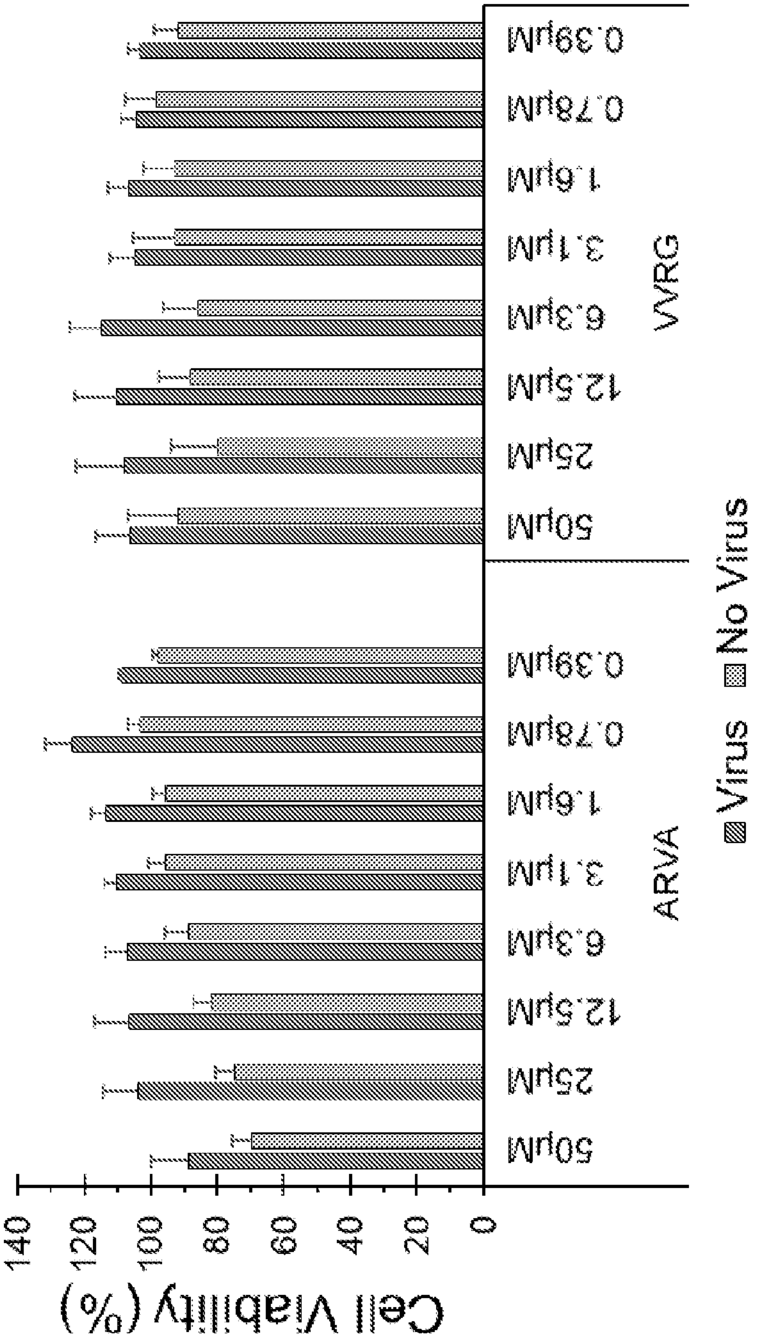
Figure 10D:
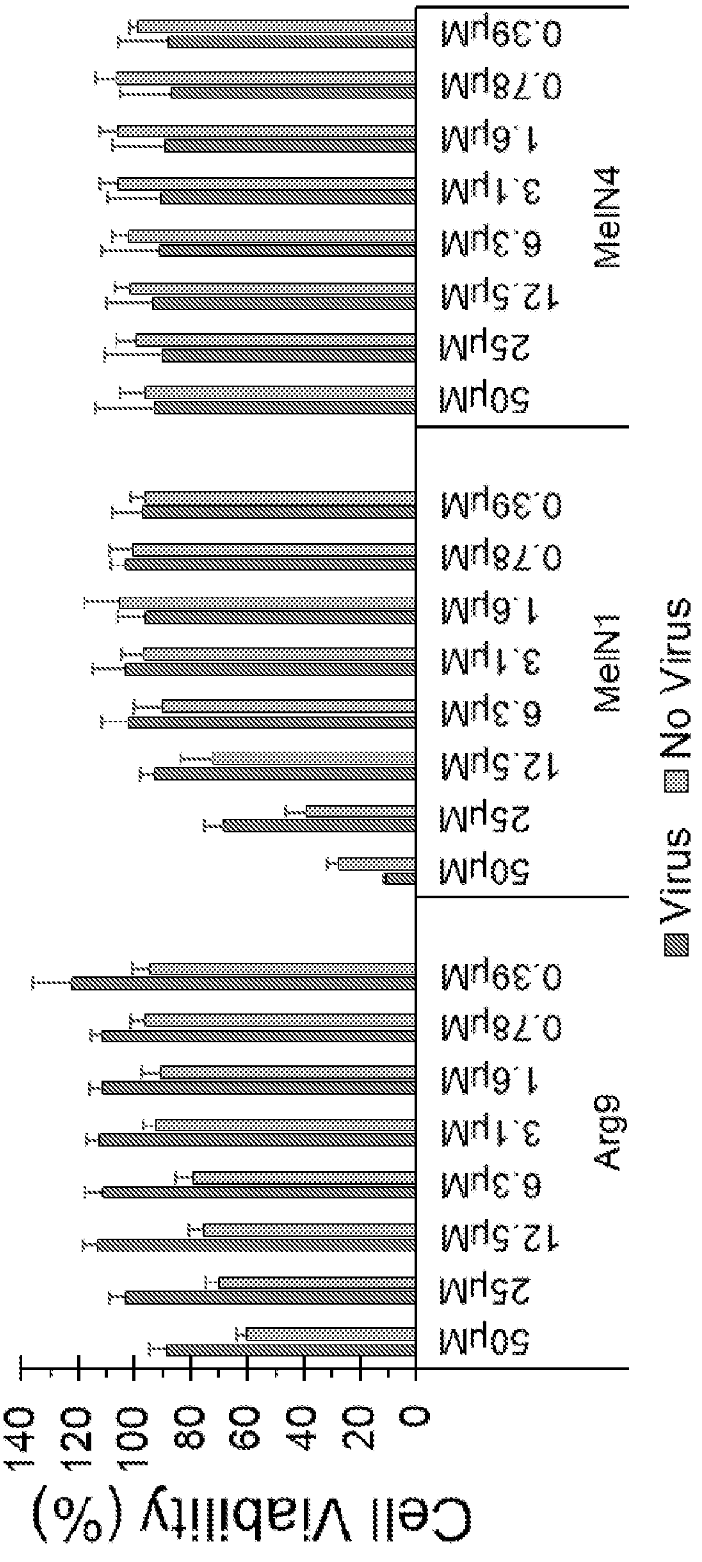

In parallel to measuring virus inhibition in Example 7, we also quantified peptide cytotoxicity using ALAMARBLUE™ reagent (FIGS. 9A-9D), used for measuring cell viability. ALAMARBLUE™ (resazurin), which is nonfluorescent, is reduced to resorufin in live cells (Chen et al. (2018) *Biotechnol. Bioeng.* 115(2):351-358). Resorufin is highly fluorescent and serves as a marker of viability (O'Brien et al. (2000) *Eur. J. Biochem.* 267(17):5421-5426). In these experiments, serial dilutions of peptides were incubated with HEK cells for 72 hours. ALAMARBLUE™ was then added to cells, incubated for 4 hours, and fluorescence was measured using a microplate reader. Of the 13 interfacially active peptides that have an antiviral $EC_{50}$ below 10 μM, 12 have cell viability measurements of over 80% at their respective $EC_{50}$ values. In addition to these measurements, we also measured peptide cytotoxicity in the presence of virus (FIGS. 10A-10D). This assay was performed using the same protocol as the virus inhibition assay described above in Example 7, with an ALAMARBLUE™ addition as opposed to Bright-Gia™ addition after 72 hours of incubation. Interestingly, for some peptide series, cell viability varies in the presence and absence of virus (e.g., IT1a, IT1b; FIG. 10A), while for others there is no difference (e.g., NATT, ARNY; FIG. 10B). This suggests that, in some cases, virus is interacting with peptide and lowering the cytotoxic potential.

TABLE 4

Therapeutic indices of interfacially active peptides.

| Name | $EC_{50}$ INFV | $EC_{50}$ LASVpv | $EC_{50}$ Tox | Index |
|---|---|---|---|---|
| Vesicle-selected (VS) Membrane Permeabilizing Peptides | | | | |
| *VDVY* | 12.0 | 5.0 | >100 | >20 |
| *ARVA | 0.9 | 6.2 | >75 | >12 |
| *arva | 0.4 | nd | nd | nd |
| ARYV | 3.7 | 7.9 | nd | nd |
| VVRG | 6.1 | nd | nd | nd |
| Biologically Selected (BS) Antimicrobial Peptides(BS) | | | | |
| *NRRV* | 8.0 | 26 | 15 | 0.6 |
| *ARNY* | 4.5 | 2.2 | >100 | >45 |
| *GRVY* | 9.1 | 2.1 | nd | nd |
| *RNNY* | 2.3 | 2.1 | 19 | 9 |
| *TNTN* | 6.1 | 1.1 | 22 | 20 |
| *NATT* | 0.7 | 1.2 | 43 | 36 |
| Synthetically Evolved, $2^{nd}$ Iteration (It) Pore-forming Peptides | | | | |
| IT1-a | 1.6 | 1.6 | 19 | 12 |
| IT1-b | 2.3 | 1.4 | >75 | >54 |
| IT1-c | 1.2 | nd | nd | nd |
| IT1-d | 0.4 | 1.3 | >100 | >77 |
| IT1-e | 0.6 | 1.2 | >50 | >42 |
| IT1-f | 1.5 | 1.1 | 20 | 18 |
| Miscellaneous and Control Peptides | | | | |
| Arg9 | 6.7 | >100 | >75 | Nd |
| Mel-L16G | nd | 28 | 21 | 0.8 |
| MelN4 | nd | >100 | >100 | Nd |

In Table 4, we provide the $EC_{50}$ values for inhibition of competent influenza virus ($EC_{50}$ INFV), inhibition of LASVpv ($EC_{50}0$ LASVpv), and cytotoxicity ($EC_{50}$ Tox). These values are from FIGS. 9 and 12. The pseudo therapeutic index (Index) shows the ratio of $EC_{50}$ for cytotoxicity to $EC_{50}$ for LASVpv inhibition. Some values were not determined (nd) in this study.

Taken together, these data show that cationic membrane active peptides with 13-sheet secondary structure possess broad-spectrum antiviral activity, the majority of which have low cytotoxicity. Nearly all library peptides tested have activity against enveloped viruses with Class I, II, and III fusion proteins. ECso values average around 1-5 μM and range from 30 μM (*NRRV*inhibition of LASVpv) to 225 nM (IT1b inhibition of DENV). Control peptides that do not possess moderate hydrophobicity with 13-sheet secondary structure, such as the polycationic peptide Arg9, and conformationally inhibited melittin analogs MeIl16G and MeIN4, do not cause significant virus inhibition. DENV is most susceptible to peptide-inducted inhibition. This could be due to a structural or sequence motifs of Class II fusion proteins or DENV fusion protein specifically. Interestingly, interfacially active peptides inhibit a non-enveloped virus, adenovirus. Although peptide antiviral activity is much lower than observed with enveloped viruses, $EC_{50}$ values are below 10 μM. This finding suggests that these peptides can interact with other viral components such as proteins and glycoconjugates.

Example 10. Peptide Wash Inhibition Assay

Figure 14:
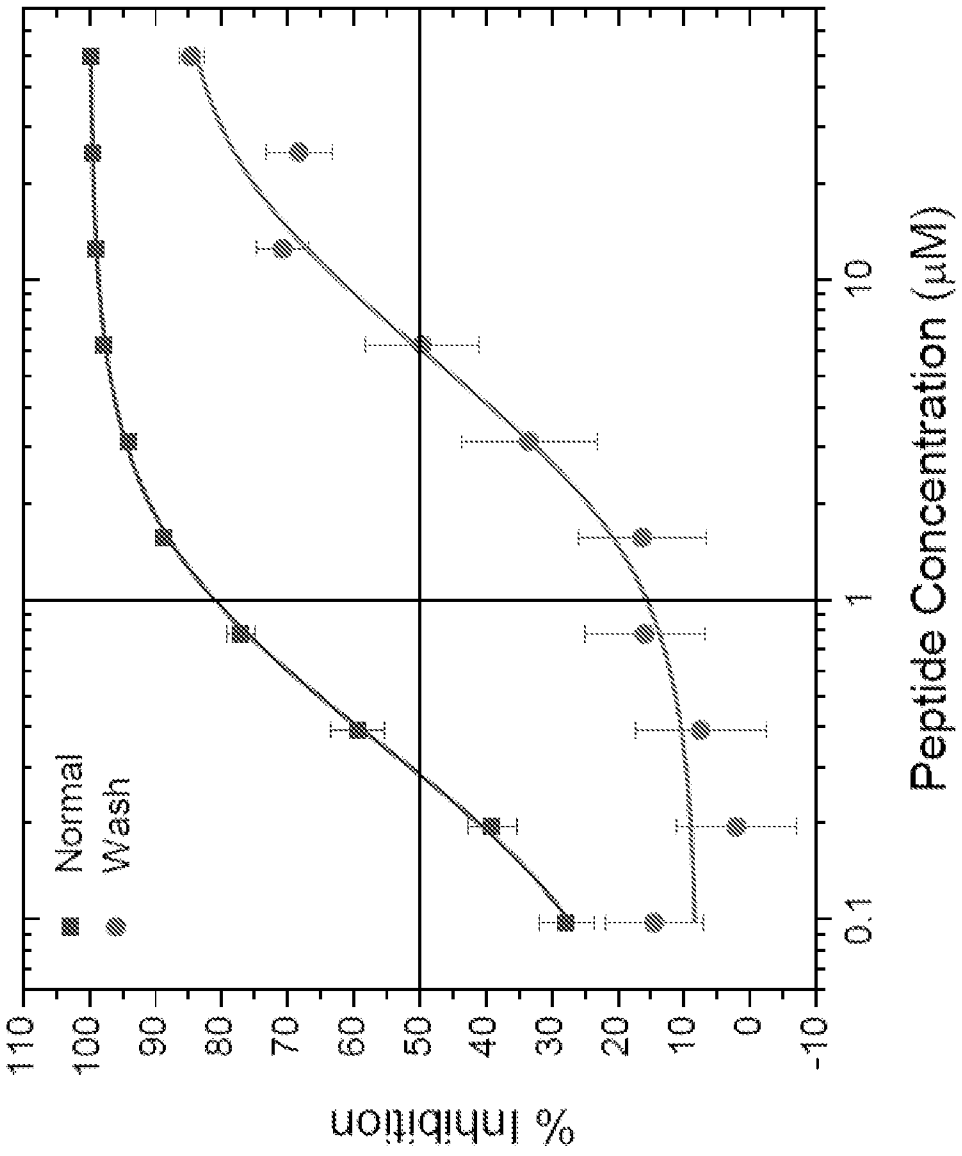
FIG. 14 is a graph showing virus inhibition assay with unbound peptide remaining with or washed from cells. For the "Normal" curve, IT1b was incubated with LASVpv for 1 hour then added to HEK cells. For the "Wash" curve, IT1b was incubated on cells for 1 hour, cells were then washed with PBS to remove excess peptide, and LASVpv was then added to these cells. Infectivity of both "Normal" and "Wash" conditions was quantified by measuring luciferase expression translated from the LASVpv genome approximately 72 hours after infection. n=8, mean±SE.

To uncover the site of inhibition, we first tested IT1b inhibition of LASVpv with HEK cells under two different scenarios (FIG. 14). In the first scenario we treated virus with peptide, incubated for 1 hour, then added this solution to cells. This is the same protocol used for inhibition curves in FIG. 9. We name this series "Normal." In the second scenario, we first incubated peptide with cells for 1 hour, washed unbound peptide from solution, then added virus to cells. We name this series "Wash." Both series were incubated for approximately 72 hours at 37° C. Cells were then lysed, and luciferase expression was measured using Bright-Glo™. We found a dramatic difference in antiviral activity between these two series. The ECso for Normal (283 nM) is approximately 20× lower than Wash (6.1 μM).

To conduct the peptide wash inhibition assay, HEK cells were first seeded in 96-well plates at a density of $1\times10^4$ cells/well in DMEM with 10% FBS and were then incubated overnight. Peptide was added to cells at varying concentrations in DMEM and incubated for 1 hour. Cells were then carefully washed twice with PBS to remove unbound peptide. Lassa pseudovirus was then added to cells at a concentration of $1\times10^3$ $TCID_{50}$/well. Lassa pseudovirus propagation was performed as described in Example 15. Infectivity was quantified by measuring luciferase expression translated from the pseudovirus genome approximately 72 hours after infection using 100 μL BRIGHT-GLO™ (Promega), prediluted 1:5 in Glo Lysis Buffer (Promega) and measured in a microplate reader.

Based on these data, the peptide does not appear to bind strongly to cells and most peptide is being washed out of solution in the Wash series. We also observe that IT1b, in this experiment, is more potent than observed in FIG. 9. This shift in IT1b activity could be due to the use of slightly different materials such as new plasmid preparations to make pseudovirus, the use of different passage numbers of the cell line, and the age of synthesized peptide.

Example 11. Time of Addition Assay

Figure 15:
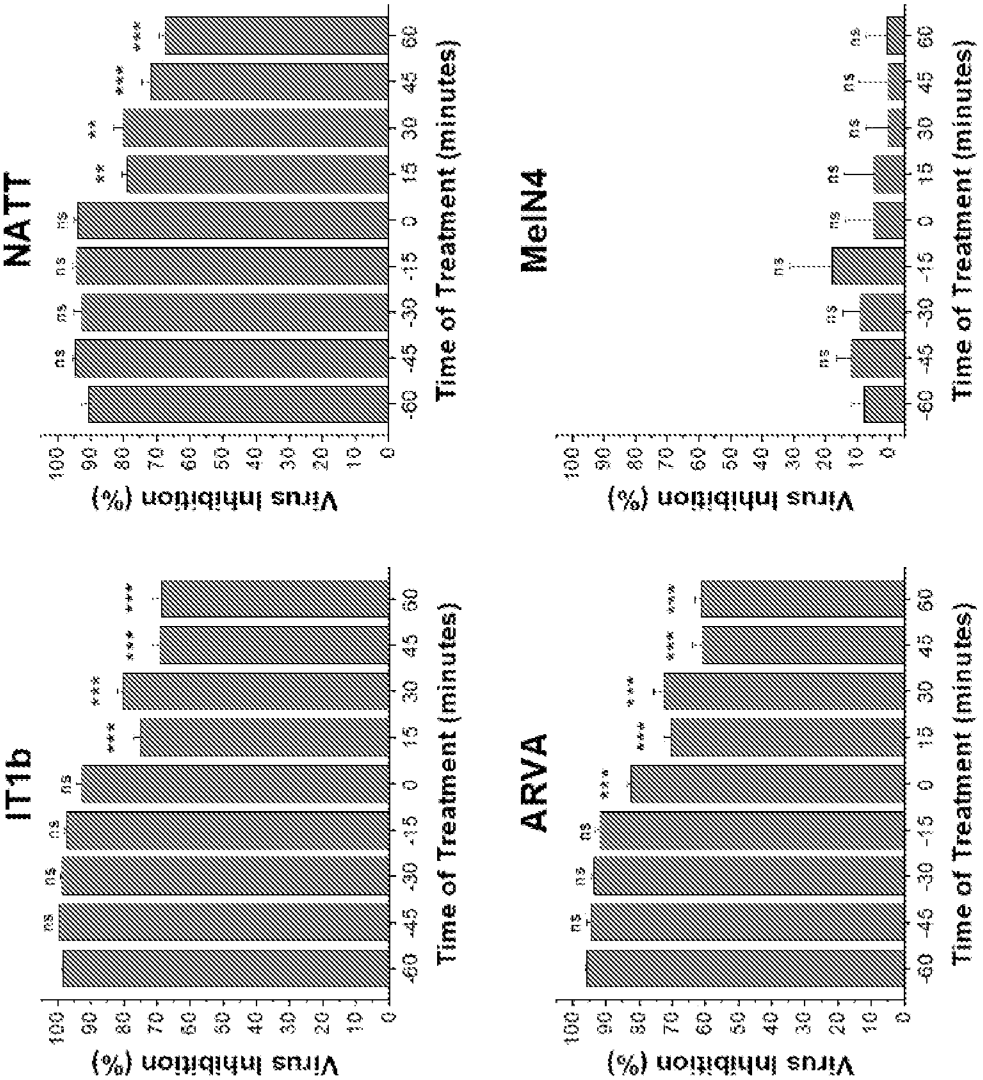
FIG. 15 is a set of graphs showing time of addition assay results for selected AVPs. Peptides were added to HEK cells at various time points before, during, and after LASVpv infection. Infectivity was quantified approximately 72 hours after infection by measuring luciferase expression translated from the LASVpv genome (n=4, mean±SE). Significance relative to the −60 minutes time point was determined by one-way ANOVA with Dunnett's post test.*, p<0.05; , p<0.01; *, p<0.001; n.s., no statistical difference.
Figure 16:
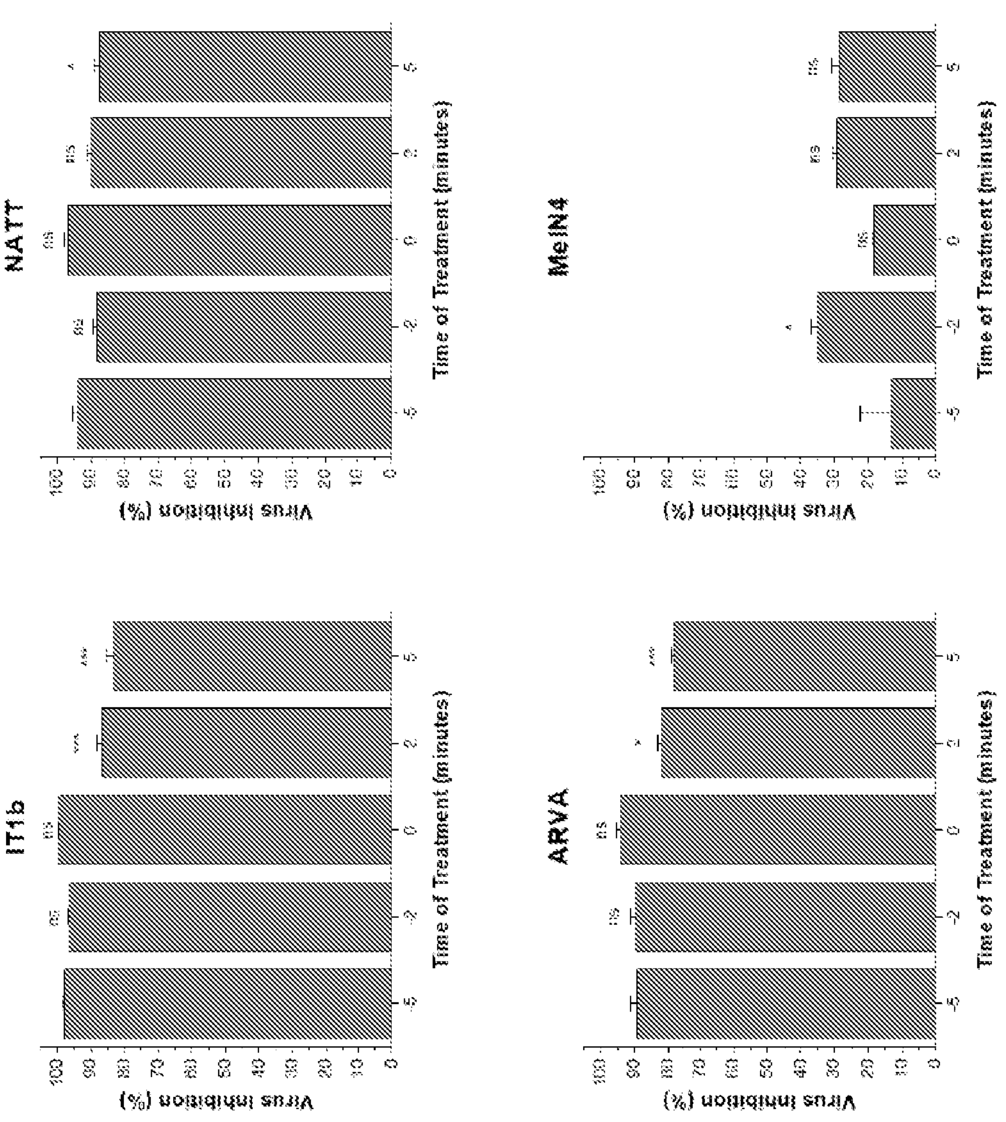
FIG. 16 is a set of graphs showing time of addition assay results for selected AVPs under a narrow time range. The time of addition assay (shown in FIG. 15) was repeated with smaller time intervals (n=4, mean±SE). Significance relative to −5 minutes was determined by one-way ANOVA with Dunnett's post test.*, p<0.05; ***, p<0.001; n.s., no statistical difference.

To determine the speed at which virus inhibition is occurring, we performed time of addition assays (FIG. 15). These experiments help determine the speed at which peptide inhibits virus and reveal if peptide is being bound then sequestered, and possibly degraded, by the cell. This information gives us further insight into the location of inhibition whether it be on the virus or cell. In previous LASVpv inhibition experiments, virus is first incubated with peptide then added to cells. For these experiments, peptides were added to HEK cells at 15-minute time intervals before and after infection with LASVpv, spanning from 60 minutes before infection to 60 minutes after infection. Infectivity was quantified approximately 72 hours post-infection by measuring luciferase expression translated from the LASVpv genome. Lassa pseudovirus propagation to generate LASVpv was performed as described in Example 15. We found that LASVpv inhibition is similar at each time point before infection (−60, −45, −30, and −15 minutes). Inhibition begins to slightly decrease as time after infection increases (15, 30, 45, and 60 minutes). To determine the time at which initial decrease of inhibition occurs, we repeated this experiment over a narrower time window (FIG. 16). Loss of inhibition can be seen in some cases in as little as 2 minutes. All library representative peptides show a decrease in inhibition after 5 minutes.

Figure 17:
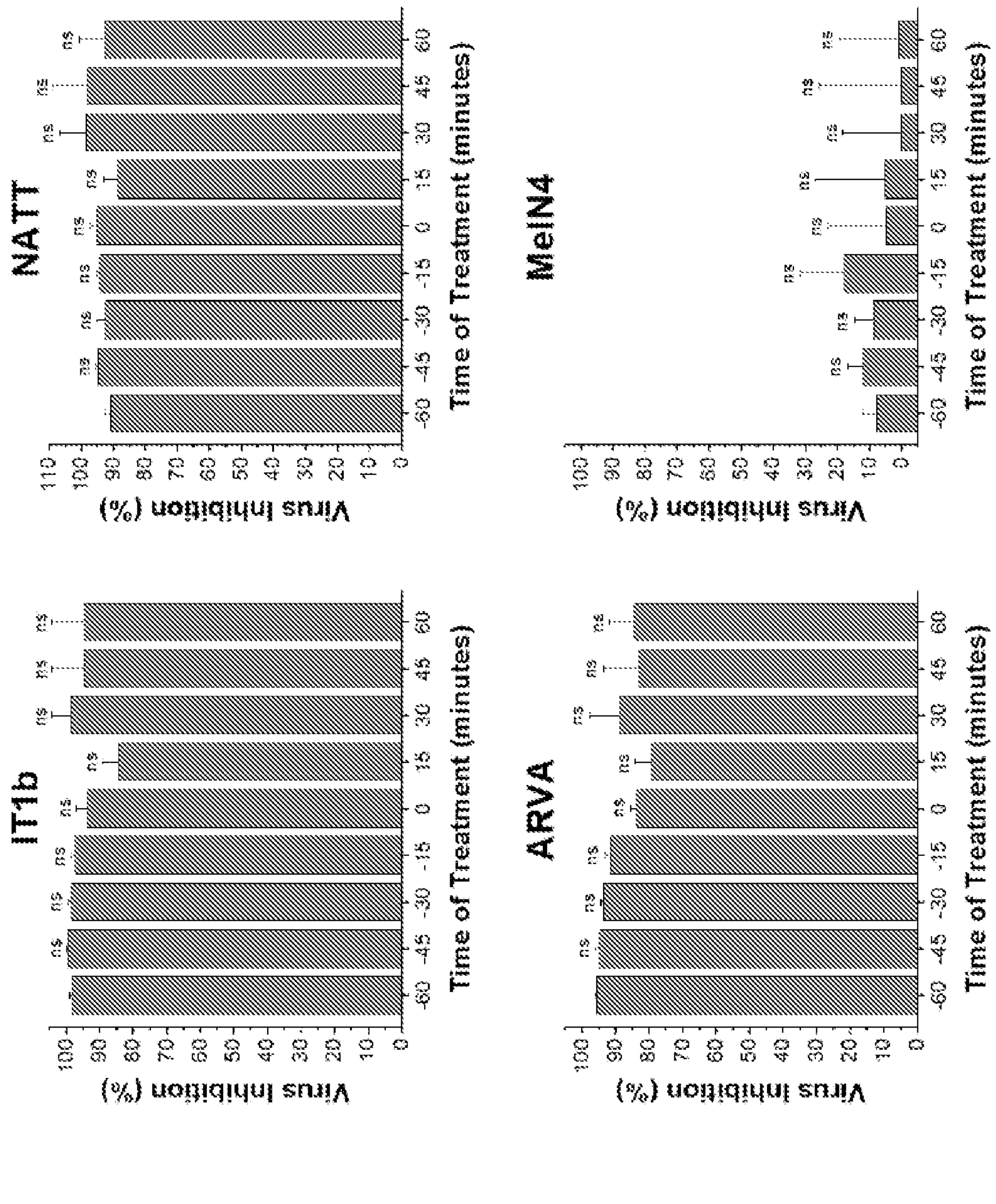
FIG. 17 is a set of graphs showing normalized time of addition assay results. The amount of virus washed from each well (i.e., virus left in suspension) was calculated based on the levels of infectivity compared to unwashed wells (Table 5). Virus inhibition measurements from FIG. 16 were normalized to the calculated levels of virus left in suspension at each measured time point (mean±SD). Significance relative to −60 minutes was determined by one-way ANOVA with Dunnett's post test. *, $p<0.05$; , $p<0.01$; *, $p<0.001$; n.s., no statistical difference.

The peptides may be inhibiting virus in the extracellular space and a decrease in inhibition over time may be due to the adsorption of virus into cells, leaving less virus to interact with peptides. We measured LASVpv titers in the supernatant at specific time intervals after initial infection (Table 5) and, over the course of an hour, viral titers drop by over 25%. When viral titers are normalized to inhibition values at the respective time intervals, inhibition remains unchanged (FIG. 17). Based on these data, we conclude that inhibition of virus infectivity occurs rapidly in the extracellular space.

TABLE 5

| Time of Virus Incubation (minutes) | Virus Left in Suspension (%) | Standard Deviation |
|---|---|---|
| 0 | 98.70 | ±0.48 |
| 15 | 88.87 | ±2.39 |
| 30 | 81.36 | ±3.50 |
| 45 | 73.06 | ±5.35 |
| 60 | 72.58 | ±4.64 |

Example 12. Binding Assay

Figure 18:
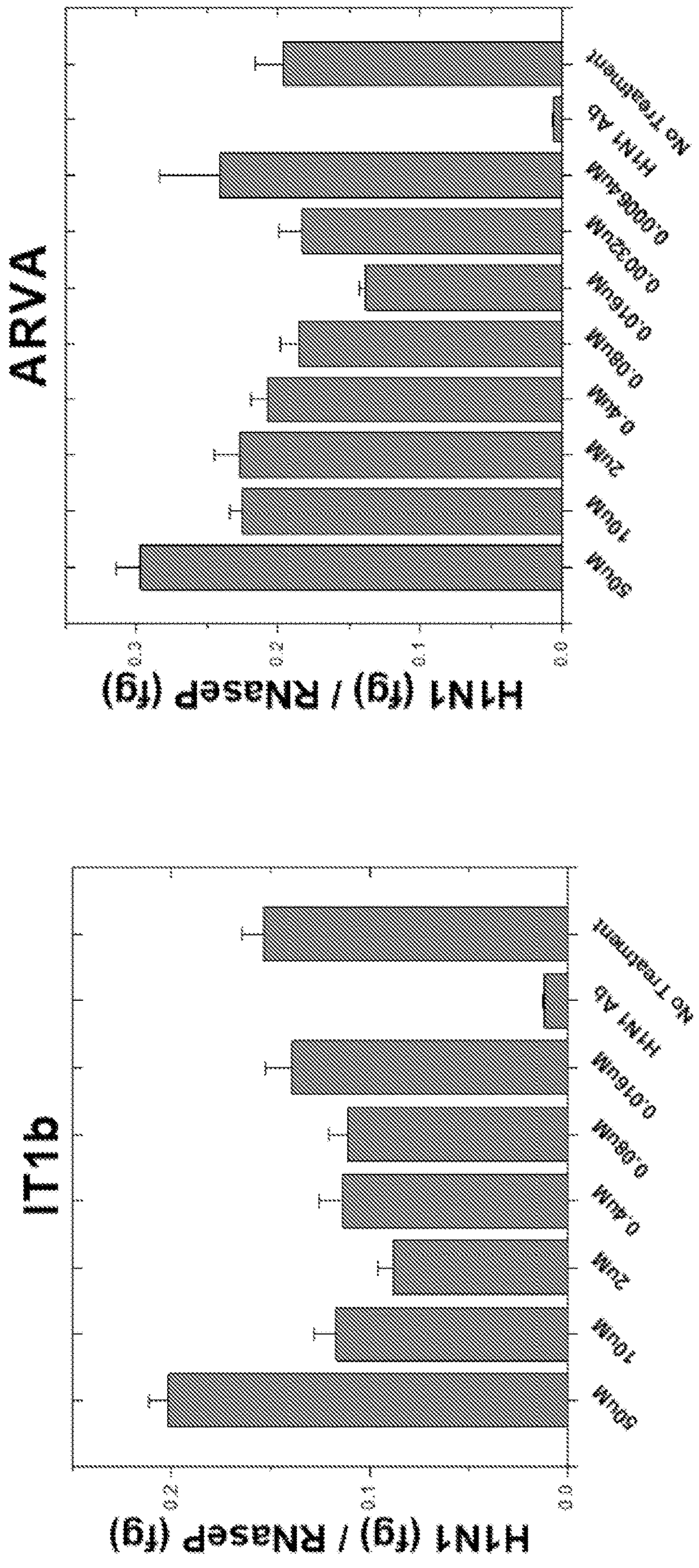
FIG. 18 is a pair of graphs showing peptide-virus binding assay results for the AVP peptides IT1b and ARVA. H1N1 was treated with peptide for 1 hour then added to HEK cells. Cells were then scraped and added on top of a silicon oil mixture. The silicon oil mixture is at a specific viscosity that allows cells to pellet but retains virions at the surface. The pellet was isolated and analyzed by qRT-PCR. H1N1 genome is plotted as a ratio of RNaseP mRNA (which is a constitutively expressed gene), to represent the relative amount of virus bound to a cell. Anti-influenza A polyclonal antibodies (H1N1 Ab) were used as a negative control for binding, and no treatment was used as a positive control for binding. n=9-15, mean±SD.

To further explore the mechanism of action of the interfacially active peptides, we examined their effect on virus-cell binding, the first step of the viral replication cycle. The binding assay was performed as described in Example 15. Peptide and H1N1 were incubated for 1 hour, then added to HEK cells for an additional hour. Cells were then scraped into suspension with unbound virus and peptide. This suspension was added on top of a silicone oil mixture. Under centrifugation, the density and viscosity of the silicon oil mixture allows cells to sediment through the oil into a pellet, carrying bound virus, while unbound virus and peptide remain at the surface of the silicon oil mixture. After centrifugation, the samples were rapidly frozen in liquid nitrogen. Pellets were isolated then analyzed by qRT-PCR. In each sample we quantified the H1N1 genome and compared it to RNaseP, a constitutively expressed gene, to determine the relative amount of virus bound to a cell (FIG. 18). This ensured a consistent quantification across samples despite potential discrepancies in cell number when scraping and collecting samples. Polyclonal Influenza A antiserum (H1N1 Ab) was used as a negative binding control and a peptide-free sample was used as a positive binding control. The antibody effectively blocked binding, and no virus is measured in the pellet. In contrast, peptide treatment causes no apparent concentration-dependent decrease in binding. Although concentration dependent trends are not directly observed, both data sets display parabolic trends. Binding data show that virus is attached to cells at high peptide concentration.

Example 13. Influenza Entry Inhibition Analysis by Confocal Microscopy

We used fluorescence confocal microscopy to examine the effect of peptide treatment on virus-cell binding and fusion. For these experiments, H1N1 envelope was labeled with the self-quenching dye rhodamine-18 (R18). Upon membrane fusion, R18 diffuses into the adjoining membrane and becomes fluorescent (Spence et al. (2014) J. Viral. 88 (15): 8556-8564; Hoekstra et al. (1984) Biochemistry 23 (24): 5675-5681). Peptide was first added to virus at 37° C. for 1 hour. This solution was then added to A549 cells then incubated at 4° C. to allow binding but not uptake of virus. Cells were then washed to remove unbound virus and peptide. Cascade blue labeled dextran was then added to cells to visualize cell boundaries. Cells were first imaged at room temperature, then incubated for 2 hours at 37° C. to allow the uptake and fusion of bound virus, then imaged again after the incubation. The sensitivity of the instrument was set so that R18 fluorescence could only be detected after the 2-hour incubation, and not during the initial binding stage. We determined viral-host fusion by monitoring R18 fluorescence localized to the cell's interior. Confocal microscopy was performed as described in Example 15.

Figure 19:
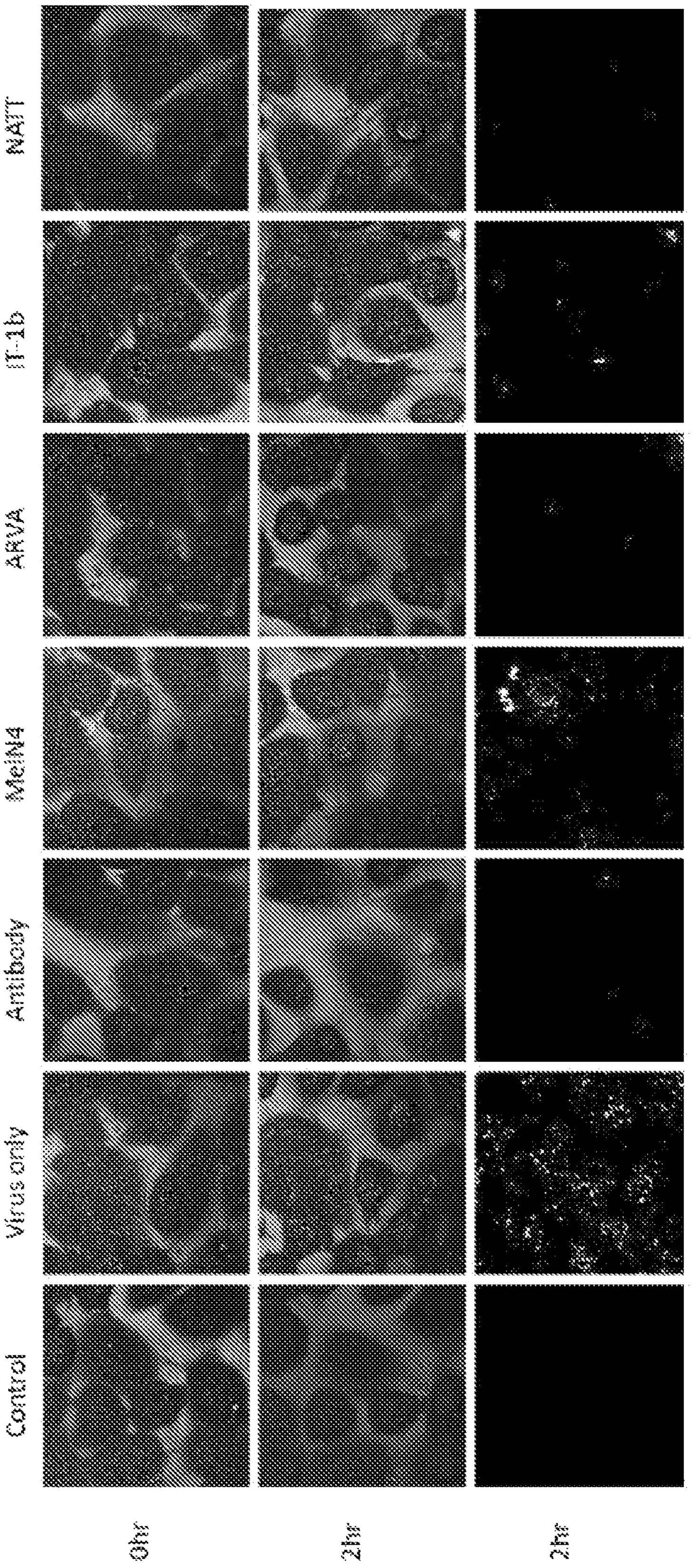
FIG. 19 is a set of representative confocal microscopy images showing R18-labeled H1N1 influenza virus that was treated with AVPs. R18-labeled H1N1 flu virus was pre-incubated with peptides for 1 hour at 37° C. This solution was then added to A549 cells for 1 hour at 4° C. to allow virus to bind but prevent uptake into the cell. After the incubation, cells were washed to clear unbound virus and peptide. Confocal microscopy images were taken at O and 2 hours while incubating cells at 37° C. Blue channel shows dextran-cascade blue to indicate cell borders; red channel shows R18-labeled viral particles that have undergone membrane disruption.

In peptide-free samples with virus, only a few particles are initially visible following the incubation at 4° C. (0 hours) (FIG. 19). After the 2-hour incubation at 37° C., many fluorescent particles are visible in the cell. Treatment with human convalescent antibody completely blocks virus entry (Antibody). Treatment with library peptides significantly reduces the number of visible virus particles when compared to untreated control. MeIN4 somewhat blocks virus fusion but not to the extent of the library peptides; this is not unexpected due to the low level of inhibition measured for other interfacially active peptides. From these observations, we conclude that interfacially active peptides effectively block fusion, and possibly binding, with host cells.

Example 14. Electron Microscopy Analysis

Figure 20:
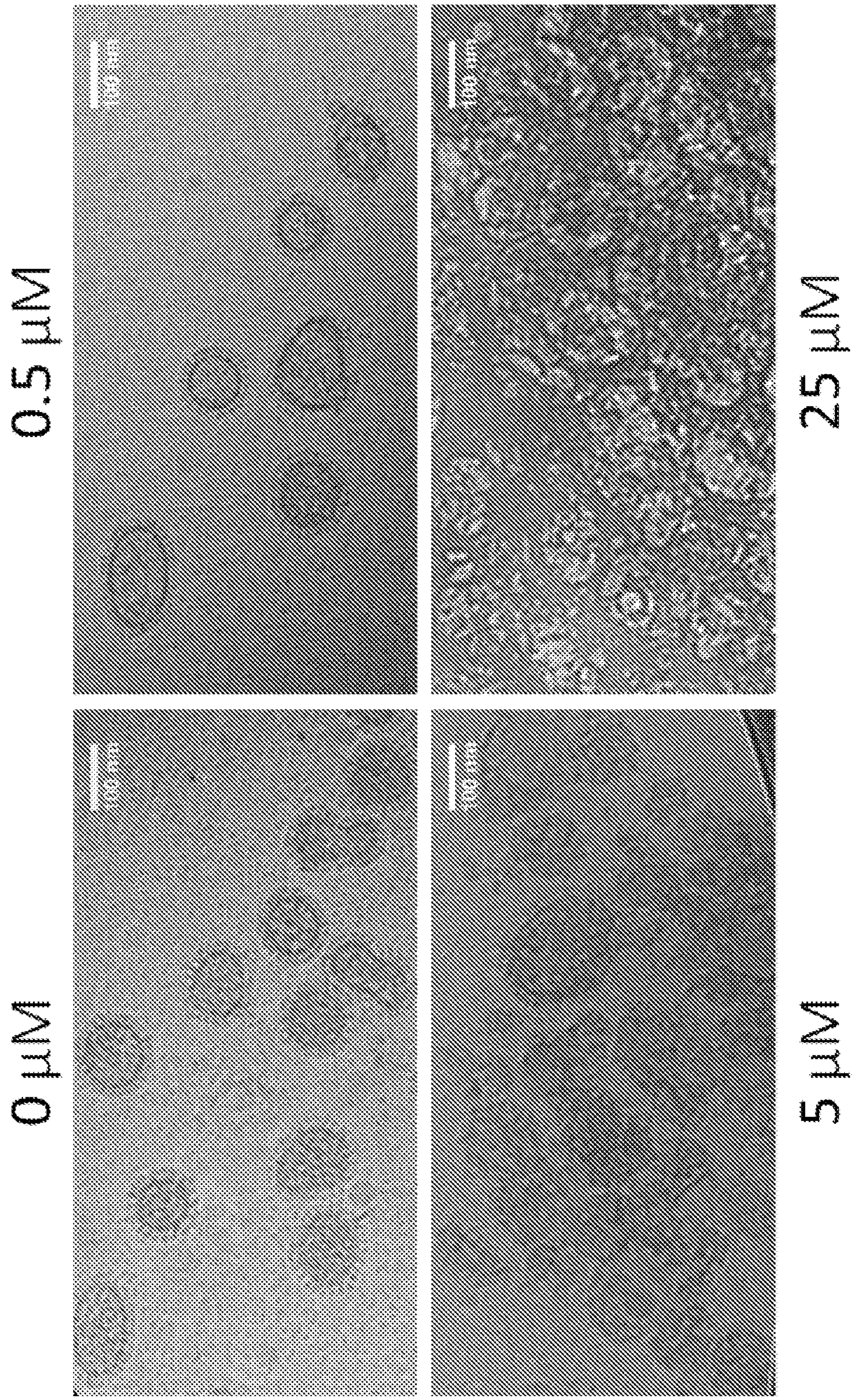
FIG. 20 is a set of representative cryo-electron microscopy images showing peptide-treated virions. H1N1 influenza virus was incubated with the indicated concentrations of NATT peptide (SEQ ID NO: 40) for 30 minutes then inactivated by UV radiation. Samples were then rapidly frozen in liquid ethane and visualized by cryo-electron microscopy.

To determine if peptides are acting directly on the viral envelope or proteins, we used cryo-electron microscopy to visualize peptide-treated virions. Cryo-electron microscopy allows us to observe changes in virus morphology that may occur during treatment. These changes could include virus aggregation, membrane destabilization, and surface protein denaturation. Electron microscopy was performed as described in Example 15. We treated H1N1 with varying concentrations of NATT for 30 minutes. This solution was UV-inactivated, rapidly frozen in liquid ethane, and imaged using an electron microscope. Peptide-free virions are easily located and are evenly dispersed in the field-of-view. The majority of virions are relatively circular with easily distinguishable surface proteins. Virions treated with 0.5 μM NATT, a concentration below the $EC_{50}$, appear very similar to the untreated sample (FIG. 20). Virions were evenly dispersed and circular. At 5 μM peptide, a concentration slightly above the $EC_{50}$, virions form clusters and few individuals are observed outside of these clusters. Virions also appear elongated with areas of concave envelope curvature. At 25 μM, a concentration well above the $EC_{50}$, structural integrity of virions is completely destroyed; no intact virions are observed. Disfigured virions and presumed viral components form large aggregates.

Figure 21A:
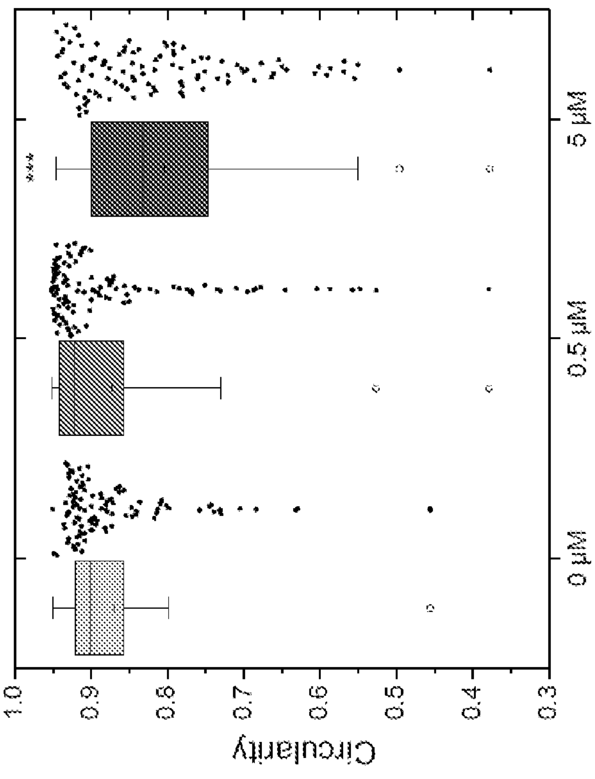
FIGS. 21A-21B are a graph showing envelope circularity measurements of peptide-treated virions and a set of representative cryo-electron microscopy images showing peptide-treated virions displaying a wide range of circularity.
Figure 21B:
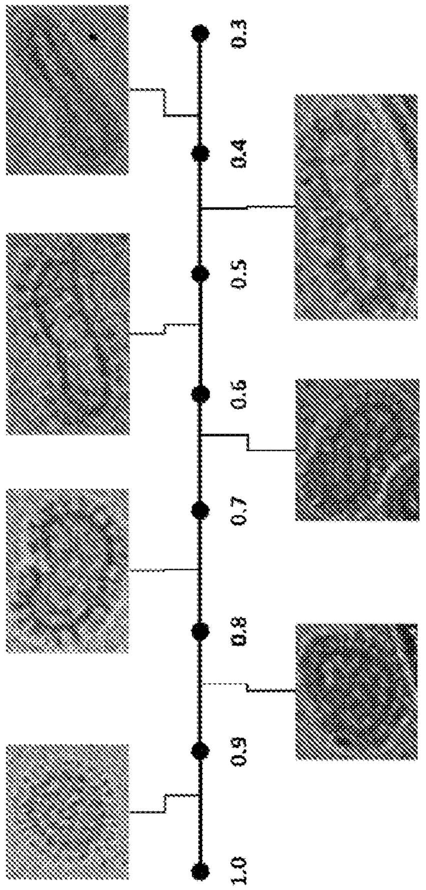

To quantitively determine if significant morphology changes resulted from increased peptide concentration, we measured the circularity of peptide-treated virions (FIG. 20). Images from samples in FIG. 20 were analyzed in ImageJ, a scientific program for image processing and analysis. Virion envelopes were traced freehand in the software and circularly was calculated from that trace (FIG. 21A). Each virion was traced three times, and the circularity of each trace was averaged. This was done to minimize error due to variance in tracing. Representative virions with a wide range of circularities were selected as visual references (FIG. 21B). We find that virions treated with 0.5 μM peptide are no different than untreated virions with an average circularity of 0.873 and 0.870 respectively. 5 μM treated virions are significantly less circular than untreated and 0.5 μM treated virions, with an average circularity of 0.805. The 25 μM treated sample cannot be measured because no intact virions are visible. Based on these data, we conclude that peptides are directly interacting with the virus, destroying structural integrity, and causing virus aggregation.

Figure 22:
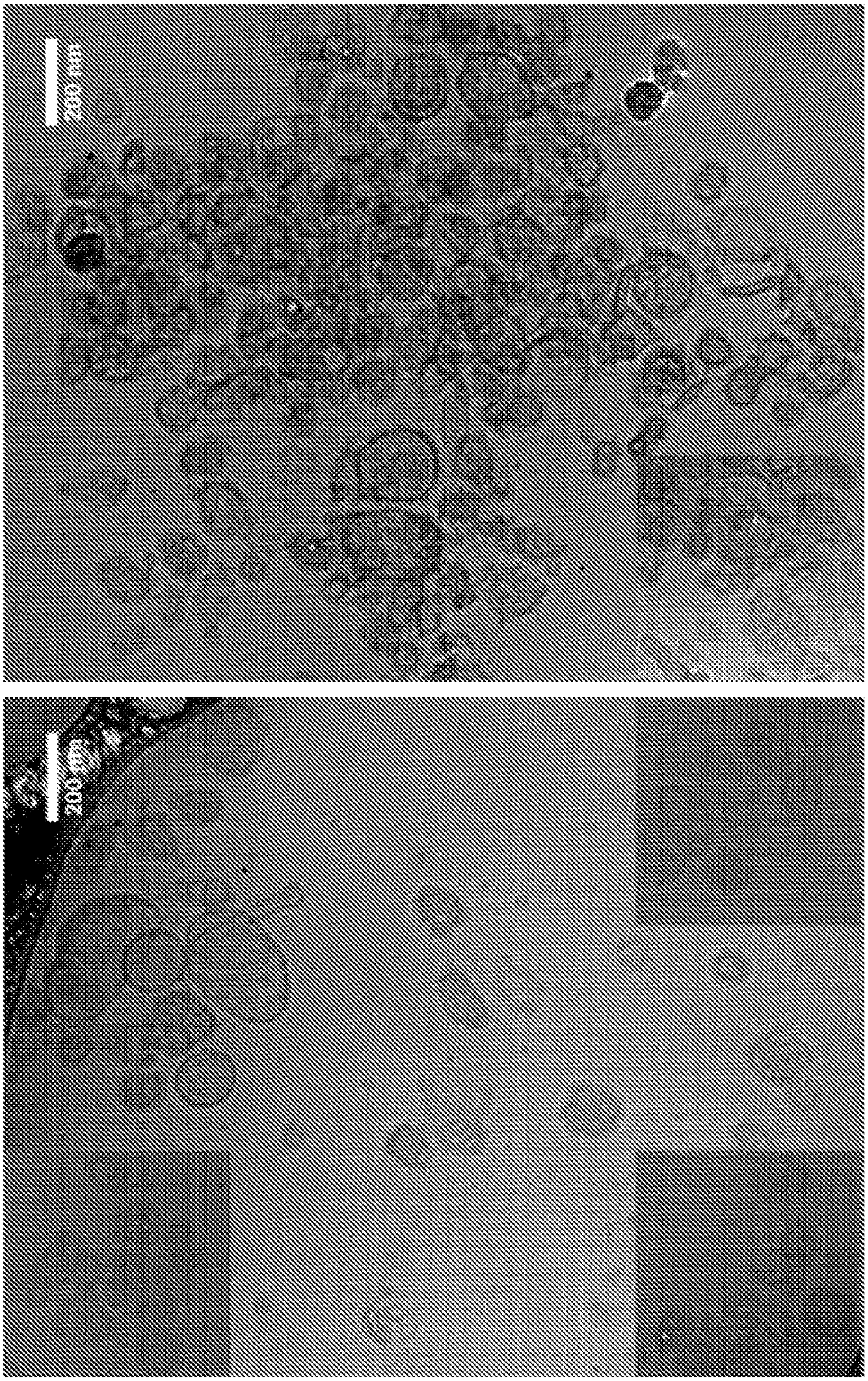
FIG. 22**B is a set of representative cryo-electron microscopy images showing representative peptide-treated virions displaying a wide range of circularity.

To establish the time frame in which virion aggregation occurs, we performed peptide treatments with short incubations. 25 μM NATT was added to H1N1, and incubated for 1 or 5 minutes, then rapidly frozen in liquid ethane. These samples were then imaged by cryo-electron microscopy. These experiments reveal that 1-minute treated samples form small clusters (FIG. 22). Viral envelopes also appear irregular and elongated. 5-minute treated samples form large aggregates and structural integrity is severely compromised. Based on these data and observations in FIGS. 15-17, we conclude that peptide directly interacts with extracellular virus, causing rapid virus aggregation on the order of minutes.

Example 15. Materials and Methods

Cells

HEK 293T/17 (ATCC® CRL-11268™), HeLa (ATCC® CCL-2™), TZM-bl (NIH AIDS Reagent Program, Catalog Number: 8129), VERO E6 (ATCC® CRL-1586™), MOCK (ATCC® CCL-34™), and A549 (ATCC® CCL-185''') cells were cultured with Dulbecco's Modified Eagle Medium (DMEM) supplemented with 10% heat inactivated fetal bovine serum (FBS).

Peptides

Peptides were purchased from Bio-Synthesis Inc. (Lewisville, Texas) with C-terminus amidation and purification to >95%. IT library peptides were dissolved in water, and all other interfacially active peptides were dissolved in 0.025% acetic acid.

For Examples 1-6, peptides were purchased from Biosynthesis Inc. (Lewisville, TX) with C-terminus amidation (purified to >90%). Peptides were dissolved in water or DMSO as indicated in FIG. 24. For Examples 9-13, peptides were purchased from Bio-synthesis Inc. (Lewisville, TX) with C-terminus amidation (purified to >95%) and dissolved in water.

Viruses

H1N1 and H3N2 influenza viruses from BEi resources and Advanced Biosciences were cultured in MOCK cells. Growth media consisted of DMEM, 0.2% bovine serum albumin, 25 mM HEPES, 2 mM L-glutamine, and 2 μg/ml TPCK-Trypsin. Cells were first washed with PBS. Original virus stock was diluted 1:100 in a low volume of growth media {3 ml per T150 flask) then added to cells for 1 hour. Growth media was then added to cell at a normal culture volume {30 ml per T150 flask). Cells were incubated at 37° C. 5% $CO_2$ until approximately 75% of cells showed cytopathic effects {CPE) {about 4-6 days). Supernatant was then collected and clarified by centrifugation at 1000×g for 15 minutes at 4° C. This solution was then aliquoted and stored at −80° C.

Dengue virus serotype 2 {New Guinea C strain) was propagated on VERO E6 cells. Cells were first washed with DMEM. Virus was added to 30 ml DMEM with 2% FBS {for a T150 flask) then added to cells. Cells were incubated until approximately 75% of cells showed CPE {about 15-16 days). Supernatant was then collected and clarified by centrifugation at 1000×g for 15 minutes at 4° C. This was then aliquoted and stored at −80° C.

Herpes simplex virus 1 (ATCC® VR-539™) and human adenovirus 5 (ATCC® VR-1516™) were cultured, clarified, and stored in the same manner as dengue virus. The incubation times were approximately 3 and 4-5 days, respectively.

Lassa Pseudovirus Propagation

Lassa pseudovirus was produced by cotransfecting HEK cells with two plasmids: pNL4-3.Luc.R-E-(NIH AIDS Reagent Program, Catalog Number: 3418), and LASV GPC plasmid (Illick et al. (2008) *Virology.* 5:161). 10 cm dishes were first coated with 100 μg/ml poly-O-lysine hydrobromide, then cells were seeded at $1\times10^7$ cells per dish.

For Examples 1-6, when monolayers were ≥90% confluent 5 μg of each plasmid was mixed with 500 μL jetPRIME® buffer (Polyplus-transfection) and transfected with 30 μL jetPRIME® transfection reagent (Polyplus-transfection) using the manufacturer's protocol. For Examples 7-14, when monolayers were ≥90% confluent, 60 μg of each plasmid were transfected with 148 μL Lipofectamine 2000 using the manufacturer's protocol. Supernatant was collected from the dishes 3 days post transfection and was clarified by centrifugation at 1000×g for 15 minutes at 4° C. The supernatant was then aliquoted and stored at −80° C.

To obtain a viral titer, pseudovirus was serial diluted on HEK cells. A column of cell-only wells was included as a measure of background. Infectivity was quantified by measuring luciferase expression translated from the pseudovirus genome approximately 72 hours after infection using 100 μL Bright-Glo™ (Promega), prediluted 1:5 in Glo Lysis Buffer (Promega), measured in a microplate reader. The Reed-Muench (Reed et al. (1938) *Am. J. Epidemiol.* 27(3):493-497) method was used to determine the $TCID_{50}$, where positive-for-infection was defined as (signal)>(background signal)+(3× standard deviation of background signal).

SARS-CoV-2 Pseudovirus Propagation

SARS-CoV-2 was produced by cotransfecting HEK 293T/17 cells with four plasmids: lentivirus backbone (VRC5602), luciferase reporter gene (VRC5601), SARS-CoV-2 Spike (VRC7480.D614G), and TMPRSS2 (VRC9260). Cells were seeded in a T75 flask at $8\times10^6$ cells/flask in DMEM with 10% FBS. The next day, 4.8 μg of lentivirus backbone plasmid, 4.8 μg luciferase reporter gene plasmid, 0.3 μg SARS-CoV-2 Spike plasmid, and 0.1 μg TMPRSS2 plasmid was mixed with 500 μL jetPRIME buffer (Polyplus-transfection) and transfected with 30 μL jetPRIME transfection reagent (Polyplus-transfection) using the manufacturer's protocol. Supernatant was collected from the flask 3 days post-transfection and was clarified by centrifugation at 1000×g for 15 minutes at 4° C. The supernatant was then aliquoted and stored at −80° C. To obtain a viral titer, pseudovirus was serial diluted on ACE2 expressing HEK/293T cells. Infectivity was quantified by measuring luciferase expression translated from the pseudovirus approximately 72 hours after infection using 100 μL Bright-Glo (Promega), prediluted 1:5 in Glo Lysis Buffer (Promega), using a microplate reader. The Reed-Muench method was used to determine a TCIDso, where positive-for-infection was defined as (signal)>(average background signal)+(3×standard deviation of background signal).

Lassa Pseudovirus Neutralization Assay

HEK cells were first seeded in 96-well plates at a density of $1\times10^4$ cells/well in DMEM with 10% FBS and were incubated overnight. Lassa pseudovirus was added at a density of $1\times10^3$ TCIDso/well (MOI=0.1) to various concentrations of peptide in DMEM and incubated for 1 hour. The culture media was then aspirated from the cells and replaced with the virus-peptide solutions. Infectivity was quantified by measuring luciferase expression translated from the pseudovirus genome approximately 72 hours after infection using 100 μL Bright-Glo™ (Promega), prediluted 1:5 in Glo Lysis Buffer (Promega), using a microplate reader. Peptide-free samples were used as a negative control for inhibition, while peptide and virus-free samples were used as a positive control for inhibition. ECso values were calculated by linear regression using data points directly above and below 50% inhibition. For Examples 1-6, ECso values were calculated using 4 parameter logistic regressions, solving for x when y=50.

SARS-CoV-2 Pseudovirus Neutralization Assay

ACE2 expressing HEK/293T cells were first seeded in 96-well plates at a density of $1\times10^4$ cells/well in DMEM with 10% FBS and were incubated overnight. SARS-CoV-2 pseudovirus was added at a density of 20 TCIDso/well to a serial dilution of various peptides in DMEM and incubated for 1 hour. The culture media was then aspirated from the cells and replaced with virus-peptide solutions. Infectivity was quantified by measuring luciferase expression translated from the pseudovirus genome approximately 72 hours after infection using Bright-Glo™ (Promega), prediluted 1:5 in Glo Lysis Buffer (Promega), using a microplate reader.

Influenza Virus Inhibition Assay

MOCK cells were seeded into 96-well plates. The assay was conducted on confluent monolayers. On the day of inoculation, two preliminary plates were prepared for each 96-well cell plate. All media used beyond this stage was FBS/BSA free. The first plate was used to dilute the H3N2 influenza virus into cell overlay media which was used to infect cells. The second plate was used to serially dilute the peptide to create a gradient of concentrations and also acted as a pre-incubation plate for the virus and peptide to mix before the infection occurred in the assay. Diluted virus was added to the peptide plate and incubated at 37° C. for 30 minutes. After the 30-minute incubation, the cell plate was washed twice with DPBS and 100 μL/well of infection media was added to each well. The plate was then incubated at 37° C. for 1 hour. After the incubation, the infection media was aspirated, and each well was washed twice with DPBS before fresh media was added. After 48 hours, the cells were washed and fixed with 4% paraformaldehyde, and then stained with DAPI. DAPI fluorescence, which measures remaining DNA (Chazotte et al. (2011) *Cold Spring Harb. Protoc.* 2011(1):pdb.prot5556), was quantified in a Biotek Synergy plate reader. ECso values were calculated by linear regression using data points directly above and below 50% inhibition.

Plaque Assay

VERO E6 cells were plated in 12-well plates in DMEM with 10% FBS at a density of $5\times10^5$ cells/well and were incubated overnight. Approximately 100 PFU/well for dengue virus and adenovirus and approximately 100 or 150 PFU/well for herpes simplex virus was mixed with serial dilutions of peptide in a total of 150 μL of DMEM per well and incubated for 1 hour. Culture media was aspirated from cells and replaced with virus-peptide solutions. This was incubated for 1 hour while rocking the plate every 15 minutes to ensure the cells were covered with inoculum. After the incubation, the inoculum was aspirated from the cells. 2×MEM with 4% FBS was mixed with 2.4% Avicel® in equal amounts to make the overlay. 1 ml of overlay was added to each well and was incubated until plaques were visible. This incubation time was 4 days for dengue virus, 2 days for herpes simplex virus, and 5-6 days for adenovirus. Plaques were visualized by crystal violet staining. Inhibition was calculated by comparing peptide sample wells to peptide-free control wells on the same plate.

Binding Assay

HEK cells were seeded on 12-well plates in DMEM with 10% FBS at a density of $5\times10^5$ cells/well and were incubated overnight. H1N1, at 50 genome copies per cell (measured by qRT-PCR), and peptide at various concentrations in DMEM were incubated for 1 hour. Culture media was aspirated from cells and was replaced with virus-peptide solutions. This was incubated for 1 hour while rocking the plate every 15 minutes to ensure cells were covered with inoculum. Cells were then scraped from the bottom of the plate and added on top of a silicon oil mixture of AR 20 and AR 200 mixed at a ratio of 7:3 respectively. This was then centrifuged at 18,500×g for 2 minutes at room temperature. Tubes were submerged in liquid nitrogen until frozen, then the bottom of the tube was clipped off to collect the pellet. RNA was extracted from the pellet using ZR Viral RNA Kit™.

qRT-PCR was performed on extracted RNA. The protocol was adapted from the CDC protocol for the detection of influenza A using qRT-PCR (World Health Organization (2009) CDC protocol of realtime RT-PCR for influenza A (H1N1) who.int/csr/resources/publications/swineflu/CDC-RealtimeRTPCR_SwineH1 Assay-2009_20090430.pdf). Influenza A forward primer: GACCRATCCTGT-CACCTCTGAC (SEQ ID NO: 60; HM590431 156-177), reverse primer: AGGGCATTYTGGACAAAKCGTCTA (SEQ ID NO: 61; HM590431 226-250), and probe: FAM-TGCAGTCCTCGCTCACTGGGCACG-BHQ1 (SEQ ID NO: 62; NM_006413.4 50-68) were used to detect flu RNA. RNaseP, a constitutively expressed gene, forward primer: AGATTTGGACCTGCGAGCG (SEQ ID NO: 63; NM_006413.4 50-68), reverse primer: GAGCGGCTGTCTCCACAAGT (SEQ ID NO: 64; NM_006413.4 95-114), and probe: CY3-TTCTGACCT-GAAGGCTCTGCGCG-BHQ2 (SEQ ID NO: 65; NM_006413.4 71-93) were used to detect RNaseP mRNA (Chen et al. (2011) *J. Clin. Microbial.* 49 (4): 1653-1656; Fan et al. (2014) BMC Infect. Dis. 14:541). Flu (HM641211 141-265) and RNaseP (NM_006413.4 21-145) gBlocks were used to construct standard curves. Non-template controls were used to determine limits of detection. Samples were run using SUPERSCRIPT™ III PLATINUM™ One-Step qRT-PCR Kit w/ROX (INVITROGEN™) on a Quant-Studio 6 Flex Real-Time PCR System using the protocol as follows: 50° C. for 30 minutes for cDNA synthesis, 95° C. for 2 minutes, and 40 amplification cycles of 95° C. for 15 seconds and 55° C. for 30 seconds with fluorescence data being gathered at each 55° C. incubation step.

Confocal Microscopy

A549 cells were seeded into an 8-well chambered confocal microscope plate and grown to approximately 60% confluency. R18 dye was added to a 20 μg aliquot of H1N1 in DPBS to a final concentration of 67 μM R18. The mixture was then light-protected and shaken at room temperature for 1 hour. Labeled virus was then passed through a 0.22 μm filter and stored on ice. Peptides and antibody were diluted in DMEM to appropriate concentrations, added to labeled virus, then incubated for 30 minutes at room temperature. Cells were then washed once with DPBS, then the virus-peptide mixture was added to cells and incubated for 1 hour at 4° C. The inoculum was then aspirated, and cells were washed once with DPBS. Finally, 50 μM Cascade Blue dextran in culture media was added to cells. Confocal microscopy was done in a stage incubator with 5% $CO_2$ that was pre-warmed to 37° C. Imaging was done at time zero (within 5 minutes of the start of incubation) and again after two hours of incubation at 37° C.

Electron Microscopy

NATT (SEQ ID NO: 40), at various concentrations, and H1N1 were incubated in DMEM for 30 minutes at 37° C. The virus was inactivated by exposing the solution to 30 minutes of UV radiation in a biosafety cabinet (Zou et al. (2013) *Viral. J.* 10:289) followed by a treatment of 200 $mJ/cm^2$ ultraviolet-C radiation (Wang et al. (2004) *Vax. Sang.* 86 (4): 230-238). Samples were then plated onto grids then frozen in liquid ethane. Samples were visualized on an FEI Tecnai G2 F30 TWIN.

Virion circularity was measured using ImageJ. Outlines of the viral envelope were traced freehand and circularity was calculated, by the software, as follows:

$$\text{circularity} = 4\pi\frac{\text{area}}{\text{perimeter}^2}$$

Example 16. Treating an Infection Using an AVP

A subject infected by a virus (e.g., human adenovirus type 1 (HAdV-1), HAdV-2, HAdV-3, HAdV-4, HAdV-5, HAdV-6, HAdV-7)), MERS-CoV, SARS-CoV, SARS-CoV-2 or variants thereof, dengue virus (e.g., DENV-1, DENV-2, DENV-3, DENV-4, DENV-5), ebolavirus (e.g., Ebola virus (Zaire ebolavirus sp.), Sudan virus (Sudan ebolavirus sp.), Tar Forest virus (Tar Forest ebolavirus sp., formerly Cote d'Ivoire ebolavirus), Bundibugyo virus (Bundibugyo ebolavirus sp.), Reston virus (Reston ebolavirus sp.)), Marburg virus (e.g., Marburg Marburgvirus sp. (e.g., Marburg virus (MARV) and Ravn virus (RAVV))), human immunodeficiency virus (e.g., HIV-1 and HIV-2), hepatitis B virus, hepatitis C virus, hepatitis D virus, herpesviruses simplex virus (e.g., herpes simplex virus type 1 (HSV-1), herpes simplex virus type 2 (HSV-2), cytomegalovirus (e.g., human cytomegalovirus (HCMV)), Epstein-Barr virus (EBV), human herpesvirus 6 (e.g., HHV-6A and HHV-6B), human herpesvirus 7 (HHV-7), Kaposi's sarcoma-associated herpesvirus (KSHV; also known as human herpesvirus 8 (HHV-8)), varicella-zoster virus (VZV)), influenza A virus (e.g., subtypes H1N1, H3N2, H5N1), and influenza B virus (e.g., B/Yamagata and B/Victoria), influenza C virus, influenza D virus, Lassa virus, respiratory syncytial virus (RSV), human metapneumovirus (hMPV), parainfluenza virus (e.g., human parainfluenza virus type 1 (HPIV-1), HPIV-2, HPIV-3, HPIV-4), measles virus (MV), West Nile virus (WNV), yellow fever virus, Zika virus (ZIKV), chikungunya virus (CHIKV), Nipah virus (NIV), and Hendra virus (HeV), feline immunodeficiency virus (FIV), feline leukemia virus (FeLV), canine distemper virus (CDV), canine parvovirus (CPV), bovine viral diarrhea (BVD) virus, or bovine leukemia virus (BLV))) could be treated by administration of an AVP (e.g., an AVP of any one of SEQ ID NOs: 1-47 or 54-59, such as an AVP of SEQ ID NO: 15 or 21). If the infection is in an organ, the AVP could be administered in a formulation (e.g., dissolved in a buffer, or lyophilized formulations reconstituted for intravenous administration). Following administration, the AVPs target and disrupt the infectivity of virus particles, thereby inhibiting viral growth and treating the infection. Following administration of the AVP, improvement in the subject's condition can be monitored and, if necessary, an additional dose(s) of the AVP could be administered.

Example 17. Administration of an AVP to a Human Subject

A human subject can be administered an AVP (e.g., an AVP of SEQ ID NO: 15 or 21) disclosed herein pre- or post-exposure to a virus (e.g., SARS-CoV-2 or a variant thereof) according to the methods described herein. The human subject may be identified as being at high risk for infection, such as an individual who has or will be traveling to a region where viral infection is prevalent, or may be identified as presenting with symptoms consistent with a viral infection.

For example, a human with an underlying health condition (e.g., one or more of hypertension, diabetes, and cardiovascular disease) may be identified as having a risk of infection of SARS-CoV-2 or a variant thereof and may be administered AVP disclosed herein (e.g., an AVP of any one or more of SEQ ID NOs: 1-47 or 54-59, or a variant thereof with 75% sequence identity thereto, or a polynucleotide encoding the AVP). The AVP composition may contain a peptide with the sequence of SEQ ID NOs: 3, 16, 24, and/or 43. The subject may also be administered an antiviral vaccine (e.g., a DNA vaccine or an RNA vaccine) containing a nucleic acid molecule encoding the Spike(S) protein of 2019-nCOV (Wuhan/WIV04/2019). The subject can then be monitored for presentation of symptoms of 2019-nCOV infection, the resolution of symptoms, and/or the production of antibodies against the modified S protein of SARS-CoV-2 or a variant thereof. If necessary, a second dose or additional doses of the AVP(s) can be administered.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. All publications, patents, and patent applications mentioned in the above specification are hereby incorporated by reference to the same extent as if each individual publication, patent or patent application was specifically and individually indicated to be incorporated by reference in its entirety.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Other embodiments are within the claims.

The invention claimed is:

1. A polypeptide comprising an amino acid sequence with at least 75% sequence identity to the amino acid sequence of any one of SEQ ID NOs: 3, 16, or 24.

2. The polypeptide of claim 1, wherein the polypeptide comprises an amino acid sequence with at least 90% sequence identity to the amino acid sequence of any one of SEQ ID NOs: 3, 16, or 24.

3. The polypeptide of claim 1, wherein the polypeptide comprises the amino acid sequence of any one of SEQ ID NOs: 3, 16, or 24.

4. A composition, comprising:

the polypeptide of claim 1; and a pharmaceutically acceptable carrier, excipient, diluent, or a therapeutic agent, individually or in any combination of any thereof.

5. The composition of claim 4, wherein:

a) the therapeutic agent is an antiviral agent, an antiviral vaccine, an antifungal agent, an antibacterial agent, an anti-inflammatory agent, or an antiparasitic agent;

b) the composition is a liquid or a solid; and/or c) the polypeptide is present in the composition in an amount of from about 1 pg to about 10 g.

6. A kit comprising the composition of claim 4 and instructions for utilization thereof.

7. The kit of claim 6, further comprising a therapeutic agent.

8. The kit of claim 7, wherein the therapeutic agent is an antiviral agent, an antiviral vaccine, an antimicrobial agent, an anti-inflammatory agent, or an antiparasitic agent, or a nucleic acid, peptide, protein, contrast agent, antibody, toxin, or small molecule.

9. A polynucleotide encoding the polypeptide of claim 1.

10. A vector comprising the polynucleotide of claim 9.

11. A method of inhibiting viral infection of a cell comprising contacting the cell with an effective amount of a polypeptide with at least 75% sequence identity to the sequence of any one of SEQ ID NOs: 3, 16, or 24, a polynucleotide encoding the polypeptide, or a vector comprising the polynucleotide.

12. The method of claim 11, wherein;

a) the cell is in a mammal and/or a human; and/or b) the viral infection is caused by a virus that belongs to a family selected from the group consisting of Adenoviridae, Arenaviridae, Coronaviridae, Flaviviridae, Herpesviridae, Orthomyxoviridae, and Retroviridae, wherein optionally the virus is selected from the group consisting of adenovirus, MERS-CoV, SARS-CoV, SARS-CoV-2 or a variant thereof, dengue virus {DENV-1), DENV-2, DENV-3, DENV-4, Ebola virus, Sudan virus, Ta" f Forest virus, Bundibugyo virus, Reston virus, Marburg virus, human immunodeficiency virus type 1 (HIV-1), HIV-2, hepatitis B virus, hepatitis C virus, hepatitis D virus, HSV-1, HSV-2, human cytomegalovirus, Epstein-Barr virus, human herpesvirus 6A (HHV-6A), HHV-6B, human herpesvirus 7 (HHV-7), Kaposi's sarcoma-associated herpesvirus (KSHV), varicella-zoster virus (VZV), influenza A virus, influenza B virus, influenza C virus, influenza D virus, Lassa virus, respiratory syncytial virus (RSV), human metapneumovirus, human parainfluenza virus type 1 (HPIV-1), HPIV-2, HPIV-3, HPIV-4, measles virus, West Nile virus, yellow fever virus, Zika virus, chikungunya virus, Nipah virus, Hendra virus, feline immunodeficiency virus, feline leukemia virus, canine distemper virus, canine parvovirus, bovine viral diarrhea virus, and bovine leukemia virus.

13. A method of treating, inhibiting, or reducing a viral infection in a subject in need thereof comprising administering a composition comprising a polypeptide with at least 75% sequence identity to the sequence of any one of SEQ ID NOs: 3, 16, or 24, a nucleic acid molecule encoding the polypeptide, or a vector comprising the nucleic acid molecule to the subject.

14. The method of claim 13, wherein:

a) the composition is administered to the subject prophylactically, the composition is administered to the subject after exposure to a virus, or the composition is administered before the subject is exposed to a virus:

b) the composition is administered to the subject by parenteral administration, optionally by intravenous, intramuscular, intradermal, subcutaneous, nasal, pulmonary, or oral administration:

c) the composition is administered to the subject one or more times daily, weekly, biweekly, or monthly, wherein optionally the composition is administered to the subject one or more times every one, two, three, four, five, six, or seven days:

d) the subject is a human; and/or e) the viral infection is caused by a virus that belongs to a family selected from the group consisting of Adenoviridae, Arenaviridae, Coronaviridae, Flaviviridae, Herpesviridae, Orthomyxoviridae, and Retroviridae, wherein optionally the virus is selected from the group consisting of adenovirus, MERS-CoV, SARS-CoV, SARS-CoV-2 or a variant thereof, dengue virus {DENV-1), DENV-2, DENV-3, DENV-4, Ebola virus, Sudan virus, Ta"f Forest virus, Bundibugyo virus, Reston virus, Marburg virus, human immunodeficiency virus type 1 (HIV-1), HIV-2, hepatitis B virus, hepatitis C virus, hepatitis D virus, HSV-1, HSV-2, human cytomegalovirus, Epstein-Barr virus, human herpesvirus 6A (HHV-6A), HHV-6B, human herpesvirus 7 (HHV-7), Kaposi's sarcoma-associated herpesvirus (KSHV), varicella-zoster virus (VZV), influenza A virus, influenza B virus, influenza C virus, influenza D virus, Lassa virus, respiratory syncytial virus (RSV), human metapneumovirus, human parainfluenza virus type 1 (HPIV-1), HPIV-2, HPIV-3, HPIV-4, measles virus, West Nile virus, yellow fever virus, Zika virus, chikungunya virus, Nipah virus, Hendra virus, feline immunodeficiency virus, feline leukemia virus, canine distemper virus, canine parvovirus, bovine viral diarrhea virus, and bovine leukemia virus.

15. The method of claim 14, wherein the polypeptide is present in the composition in an amount of from about 1 pg to about 10 g.

16. The method of claim 14, wherein the virus is Influenza A virus subtype H1N1, H3N2, H9N2, H3N8, or H5N1.

* * * * *

SEQUENCE LISTING

```
<160> NUMBER OF SEQ ID NOS: 65

<210> SEQ ID NO 1
<211> LENGTH: 35
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is is Gly, any amino acid, or absent
<220> FEATURE:
<221> NAME/KEY: MISC_FEATURE
<222> LOCATION: (4)..(4)
<223> OTHER INFORMATION: Xaa is Trp, Tyr, or Phe
<220> FEATURE:
<221> NAME/KEY: MISC_FEATURE
<222> LOCATION: (6)..(6)
<223> OTHER INFORMATION: Xaa is Leu or absent; If Xaa at any position
      between 7 to 10 is present, then Xaa at position 6 must also
      present; If Xaa at position 6 is absent, then Xaa at positions 7
      through 10 must also be absent;
<220> FEATURE:
<221> NAME/KEY: MISC_FEATURE
<222> LOCATION: (7)..(7)
<223> OTHER INFORMATION: Xaa is Leu or absent; If Xaa at any position
      between 8 to 10 is present, then Xaa at position 7 must be
      present; If Xaa at position 7 is absent, then Xaa at positions 8
      through 10 must also be absent;
<220> FEATURE:
<221> NAME/KEY: MISC_FEATURE
<222> LOCATION: (8)..(8)
<223> OTHER INFORMATION: Xaa is Leu or absent; If Xaa at positions 9 or
      10 is present, then Xaa at position 8 must be present; If Xaa at
      position 8 is absent, then Xaa at positions 9 and 10 must also be
      absent;
<220> FEATURE:
<221> NAME/KEY: MISC_FEATURE
<222> LOCATION: (9)..(9)
<223> OTHER INFORMATION: Xaa is Leu or absent; If Xaa at position 10 is
```

```
      present, then Xaa at position 9 must be present; If Xaa at
      position 9 is absent, then Xaa at position 10 must also be absent;
<220> FEATURE:
<221> NAME/KEY: MISC_FEATURE
<222> LOCATION: (10)..(10)
<223> OTHER INFORMATION: Xaa is Leu or absent
<220> FEATURE:
<221> NAME/KEY: MISC_FEATURE
<222> LOCATION: (11)..(11)
<223> OTHER INFORMATION: Xaa is Lys, Arg, Asp, Glu, Ser, Thr, Asn, Gln,
      Cys, Gly, or Pro
<220> FEATURE:
<221> NAME/KEY: MISC_FEATURE
<222> LOCATION: (13)..(13)
<223> OTHER INFORMATION: Xaa is Leu or absent; If Xaa at any position
      between 14 to 17 is present, then Xaa at position 13 must also
      present; If Xaa at position 13 is absent, then Xaa at positions 14
      through 17 must also be absent;
<220> FEATURE:
<221> NAME/KEY: MISC_FEATURE
<222> LOCATION: (14)..(14)
<223> OTHER INFORMATION: Xaa is Leu or absent; If Xaa at any position
      between 15 to 17 is present, then Xaa at position 14 must also
      present; If Xaa at position 14 is absent, then Xaa at positions 15
      through 17 must also be absent;
<220> FEATURE:
<221> NAME/KEY: MISC_FEATURE
<222> LOCATION: (15)..(15)
<223> OTHER INFORMATION: Xaa is Leu or absent; If Xaa at any position
      between 16 to 17 is present, then Xaa at position 15 must also
      present; If Xaa at position 15 is absent, then Xaa at positions 16
      through 17 must also be absent;
<220> FEATURE:
<221> NAME/KEY: MISC_FEATURE
<222> LOCATION: (16)..(16)
<223> OTHER INFORMATION: Xaa is Leu or absent; If Xaa at position 17 is
      present, then Xaa at position 16 must also present; If Xaa at
      position 16 is absent, then Xaa at position 17 must also be
      absent;
<220> FEATURE:
<221> NAME/KEY: MISC_FEATURE
<222> LOCATION: (17)..(17)
<223> OTHER INFORMATION: Xaa is Leu or absent
<220> FEATURE:
<221> NAME/KEY: MISC_FEATURE
<222> LOCATION: (18)..(18)
<223> OTHER INFORMATION: Xaa is Lys, Arg, Asp, Glu, Ser, Thr, Asn, Gln,
      Cys, Gly, Pro or absent; If Xaa at position 18 is absent, then Xaa
      at positions 19 through 31 must also be absent
<220> FEATURE:
<221> NAME/KEY: MISC_FEATURE
<222> LOCATION: (19)..(19)
<223> OTHER INFORMATION: Xaa is Leu or absent; If Xaa at position 18 is
      present, then Xaa at position 19 is present; If Xaa at position 18
      is absent, then Xaa at position 19 is also absent
<220> FEATURE:
<221> NAME/KEY: MISC_FEATURE
<222> LOCATION: (20)..(20)
<223> OTHER INFORMATION: Xaa is Leu or absent; If Xaa at any position
      between 21 to 24 is present, then Xaa at position 20 must also
      present; If Xaa at position 20 is absent, then Xaa at positions 21
      through 24 must also be absent;
<220> FEATURE:
<221> NAME/KEY: MISC_FEATURE
<222> LOCATION: (21)..(21)
<223> OTHER INFORMATION: Xaa is Leu or absent; If Xaa at any position
      between 22 to 24 is present, then Xaa at position 21 must also
      present; If Xaa at position 21 is absent, then Xaa at positions 22
      through 24 must also be absent;
<220> FEATURE:
<221> NAME/KEY: MISC_FEATURE
<222> LOCATION: (22)..(22)
<223> OTHER INFORMATION: Xaa is Leu or absent; If Xaa at any position
      between 23 and 24 is present, then Xaa at any position 22 must
      also be present; If Xaa at position 22 is absent, then Xaa at
      positions 23 and 24 must also be absent;
<220> FEATURE:
<221> NAME/KEY: MISC_FEATURE
<222> LOCATION: (23)..(23)
```

<223> OTHER INFORMATION: Xaa is Leu or absent; If Xaa at position 24 is present, then Xaa at position 23 must also present; If Xaa at position 23 is absent, then Xaa at position 24 must also be absent;
<220> FEATURE:
<221> NAME/KEY: MISC_FEATURE
<222> LOCATION: (24)..(24)
<223> OTHER INFORMATION: Xaa is Leu or absent
<220> FEATURE:
<221> NAME/KEY: MISC_FEATURE
<222> LOCATION: (25)..(25)
<223> OTHER INFORMATION: Xaa is Lys, Arg, Asp, Glu, Ser, Thr, Asn, Gln, Cys, Gly, Pro, or absent; If Xaa at position 18 is absent, then position 25 is also absent; If Xaa at position 25 is absent, then Xaa at positions 26 through 31 are absent;
<220> FEATURE:
<221> NAME/KEY: MISC_FEATURE
<222> LOCATION: (26)..(26)
<223> OTHER INFORMATION: Xaa is Leu or absent; If Xaa at position 25 is present, then Xaa at position 26 is present; If Xaa at position 25 is absent, then Xaa at position 26 is also absent
<220> FEATURE:
<221> NAME/KEY: MISC_FEATURE
<222> LOCATION: (27)..(27)
<223> OTHER INFORMATION: Xaa is Leu or absent; If Xaa at any position between 28 to 31 is present, then Xaa at position 27 must also present; If Xaa at position 27 is absent, then Xaa at positions 28 through 31 must also be absent;
<220> FEATURE:
<221> NAME/KEY: MISC_FEATURE
<222> LOCATION: (28)..(28)
<223> OTHER INFORMATION: Xaa is Leu or absent; If Xaa at any position between 29 to 31 is present, then Xaa at position 28 must also present; If Xaa at position 28 is absent, then Xaa at positions 29 through 31 must also be absent;
<220> FEATURE:
<221> NAME/KEY: MISC_FEATURE
<222> LOCATION: (29)..(29)
<223> OTHER INFORMATION: Xaa is Leu or absent; If Xaa at positions 30 and 31 are present, then Xaa at position 29 must also be present; If Xaa at position 29 is absent, then Xaa at positions 30 and 31 must also be absent;
<220> FEATURE:
<221> NAME/KEY: MISC_FEATURE
<222> LOCATION: (30)..(30)
<223> OTHER INFORMATION: Xaa is Leu or absent; If Xaa at position 31 is present, then Xaa at position 30 must also present; If Xaa at position 30 is absent, then Xaa at position 31 must also be absent;
<220> FEATURE:
<221> NAME/KEY: MISC_FEATURE
<222> LOCATION: (31)..(31)
<223> OTHER INFORMATION: Xaa is Leu or absent
<220> FEATURE:
<221> NAME/KEY: MISC_FEATURE
<222> LOCATION: (32)..(32)
<223> OTHER INFORMATION: Xaa is Trp, Tyr, or Phe
<220> FEATURE:
<221> NAME/KEY: MISC_FEATURE
<222> LOCATION: (33)..(33)
<223> OTHER INFORMATION: Xaa is Gly or any amino acid

<400> SEQUENCE: 1

```
Arg Arg Xaa Xaa Leu Xaa Xaa Xaa Xaa Xaa Xaa Leu Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Arg Arg
        35
```

<210> SEQ ID NO 2
<211> LENGTH: 15
<212> TYPE: PRT
<213> ORGANISM: Artificial Sequence
<220> FEATURE:

<223> OTHER INFORMATION: Synthetic Construct

<400> SEQUENCE: 2

```
Arg Arg Gly Trp Leu Leu Leu Arg Leu Leu Leu Trp Gly Arg Arg
1               5                   10                  15
```

<210> SEQ ID NO 3
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Gly
<220> FEATURE:
<221> NAME/KEY: MISC_FEATURE
<222> LOCATION: (4)..(4)
<223> OTHER INFORMATION: Xaa is D-Trp
<220> FEATURE:
<221> NAME/KEY: MISC_FEATURE
<222> LOCATION: (5)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Arg
<220> FEATURE:
<221> NAME/KEY: MISC_FEATURE
<222> LOCATION: (9)..(11)
<223> OTHER INFORMATION: Xaa is D-Leu
<220> FEATURE:
<221> NAME/KEY: MISC_FEATURE
<222> LOCATION: (12)..(12)
<223> OTHER INFORMATION: Xaa is D-Trp
<220> FEATURE:
<221> NAME/KEY: MISC_FEATURE
<222> LOCATION: (13)..(13)
<223> OTHER INFORMATION: Xaa is D-Gly
<220> FEATURE:
<221> NAME/KEY: MISC_FEATURE
<222> LOCATION: (14)..(15)
<223> OTHER INFORMATION: Xaa is D-Arg

<400> SEQUENCE: 3

```
Xaa Xaa Xaa Xaa Xaa Xaa Xaa Xaa Xaa Xaa Xaa Xaa Xaa Xaa Xaa
1               5                   10                  15
```

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

```
Arg Arg Gly Trp Leu Arg Leu Trp Gly Arg Arg
1               5                   10
```

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Arg Arg Gly Trp Leu Leu Arg Leu Leu Trp Gly Arg Arg
1 5 10

<210> SEQ ID NO 6
<211> LENGTH: 13
<212> TYPE: PRT
<213> ORGANISM: Artificial Sequence
<220> FEATURE:
<223> OTHER INFORMATION: Synthetic Construct

<400> SEQUENCE: 6

Arg Arg Gly Trp Leu Leu Leu Arg Leu Trp Gly Arg Arg
1 5 10

<210> SEQ ID NO 7
<211> LENGTH: 16
<212> TYPE: PRT
<213> ORGANISM: Artificial Sequence
<220> FEATURE:
<223> OTHER INFORMATION: Synthetic Construct

<400> SEQUENCE: 7

Arg Arg Gly Trp Leu Leu Arg Leu Leu Arg Leu Leu Trp Gly Arg Arg
1 5 10 15

<210> SEQ ID NO 8
<211> LENGTH: 19
<212> TYPE: PRT
<213> ORGANISM: Artificial Sequence
<220> FEATURE:
<223> OTHER INFORMATION: Synthetic Construct

<400> SEQUENCE: 8

Arg Arg Gly Trp Leu Arg Leu Arg Leu Arg Leu Arg Leu Arg Leu Trp
1 5 10 15

Gly Arg Arg

<210> SEQ ID NO 9
<211> LENGTH: 15
<212> TYPE: PRT
<213> ORGANISM: Artificial Sequence
<220> FEATURE:
<223> OTHER INFORMATION: Synthetic Construct

<400> SEQUENCE: 9

Arg Arg Gly Trp Leu Leu Leu Asn Leu Leu Leu Trp Gly Arg Arg
1 5 10 15

<210> SEQ ID NO 10
<211> LENGTH: 16
<212> TYPE: PRT
<213> ORGANISM: Artificial Sequence
<220> FEATURE:
<223> OTHER INFORMATION: Synthetic Construct

<400> SEQUENCE: 10

Arg Arg Gly Trp Leu Leu Asn Leu Leu Asn Leu Leu Trp Gly Arg Arg
1 5 10 15

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Arg Arg Gly Trp Leu Leu Leu Trp Leu Leu Leu Trp Gly Arg Arg
1 5 10 15

<210> SEQ ID NO 12
<211> LENGTH: 16
<212> TYPE: PRT
<213> ORGANISM: Artificial Sequence
<220> FEATURE:
<223> OTHER INFORMATION: Synthetic Construct

<400> SEQUENCE: 12

Arg Arg Gly Trp Leu Leu Trp Leu Leu Trp Leu Leu Trp Gly Arg Arg
1 5 10 15

<210> SEQ ID NO 13
<211> LENGTH: 19
<212> TYPE: PRT
<213> ORGANISM: Artificial Sequence
<220> FEATURE:
<223> OTHER INFORMATION: Synthetic Construct

<400> SEQUENCE: 13

Arg Arg Gly Trp Leu Leu Leu Arg Leu Leu Leu Arg Leu Leu Leu Trp
1 5 10 15

Gly Arg Arg

<210> SEQ ID NO 14
<211> LENGTH: 23
<212> TYPE: PRT
<213> ORGANISM: Artificial Sequence
<220> FEATURE:
<223> OTHER INFORMATION: Synthetic Construct

<400> SEQUENCE: 14

Arg Arg Gly Trp Leu Leu Leu Arg Leu Leu Leu Arg Leu Leu Leu Arg
1 5 10 15

Leu Leu Leu Trp Gly Arg Arg
20

<210> SEQ ID NO 15
<211> LENGTH: 21
<212> TYPE: PRT
<213> ORGANISM: Artificial Sequence
<220> FEATURE:
<223> OTHER INFORMATION: Synthetic Construct

<400> SEQUENCE: 15

Arg Arg Gly Trp Leu Leu Leu Arg Leu Leu Arg Leu Leu Leu Arg Leu
1 5 10 15

Leu Trp Gly Arg Arg
20

<210> SEQ ID NO 16
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Gly

```
<220> FEATURE:
<221> NAME/KEY: MISC_FEATURE
<222> LOCATION: (4)..(4)
<223> OTHER INFORMATION: Xaa is D-Trp
<220> FEATURE:
<221> NAME/KEY: MISC_FEATURE
<222> LOCATION: (5)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Arg
<220> FEATURE:
<221> NAME/KEY: MISC_FEATURE
<222> LOCATION: (9)..(10)
<223> OTHER INFORMATION: Xaa is D-Leu
<220> FEATURE:
<221> NAME/KEY: MISC_FEATURE
<222> LOCATION: (11)..(11)
<223> OTHER INFORMATION: Xaa is D-Arg
<220> FEATURE:
<221> NAME/KEY: MISC_FEATURE
<222> LOCATION: (12)..(14)
<223> OTHER INFORMATION: Xaa is D-Leu
<220> FEATURE:
<221> NAME/KEY: MISC_FEATURE
<222> LOCATION: (15)..(15)
<223> OTHER INFORMATION: Xaa is D-Arg
<220> FEATURE:
<221> NAME/KEY: MISC_FEATURE
<222> LOCATION: (16)..(17)
<223> OTHER INFORMATION: Xaa is D-Leu
<220> FEATURE:
<221> NAME/KEY: MISC_FEATURE
<222> LOCATION: (18)..(18)
<223> OTHER INFORMATION: Xaa is D-Trp
<220> FEATURE:
<221> NAME/KEY: MISC_FEATURE
<222> LOCATION: (19)..(19)
<223> OTHER INFORMATION: Xaa is D-Gly
<220> FEATURE:
<221> NAME/KEY: MISC_FEATURE
<222> LOCATION: (20)..(21)
<223> OTHER INFORMATION: Xaa is D-Arg

<400> SEQUENCE: 16

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20


<210> SEQ ID NO 17
<211> LENGTH: 28
<212> TYPE: PRT
<213> ORGANISM: Artificial Sequence
<220> FEATURE:
<223> OTHER INFORMATION: Synthetic Construct

<400> SEQUENCE: 17

Arg Arg Gly Trp Leu Leu Leu Arg Leu Leu Leu Arg Gly Gly Gly Gly
1               5                   10                  15

Arg Leu Leu Leu Arg Leu Leu Leu Trp Gly Arg Arg
            20                  25


<210> SEQ ID NO 18
<211> LENGTH: 26
<212> TYPE: PRT
<213> ORGANISM: Artificial Sequence
<220> FEATURE:
<223> OTHER INFORMATION: Synthetic Construct

<400> SEQUENCE: 18
```

Arg Arg Gly Trp Leu Leu Leu Arg Leu Leu Leu Gly Gly Gly Gly Leu
1 5 10 15

Leu Leu Arg Leu Leu Leu Trp Gly Arg Arg
20 25

<210> SEQ ID NO 19
<211> LENGTH: 28
<212> TYPE: PRT
<213> ORGANISM: Artificial Sequence
<220> FEATURE:
<223> OTHER INFORMATION: Synthetic Construct

<400> SEQUENCE: 19

Arg Arg Gly Trp Leu Leu Leu Arg Leu Leu Leu Trp Gly Gly Gly Gly
1 5 10 15

Trp Leu Leu Leu Arg Leu Leu Leu Trp Gly Arg Arg
20 25

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Arg Arg Gly Trp Leu Leu Leu Leu Arg Leu Leu Leu Leu Trp Gly Arg
1 5 10 15

Arg

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Arg Arg Gly Trp Leu Leu Leu Leu Asn Leu Leu Leu Leu Trp Gly Arg
1 5 10 15

Arg

<210> SEQ ID NO 22
<211> LENGTH: 15
<212> TYPE: PRT
<213> ORGANISM: Artificial Sequence
<220> FEATURE:
<223> OTHER INFORMATION: Synthetic Construct

<400> SEQUENCE: 22

Arg Arg Trp Leu Leu Leu Leu Arg Leu Leu Leu Leu Trp Arg Arg
1 5 10 15

<210> SEQ ID NO 23
<211> LENGTH: 15
<212> TYPE: PRT
<213> ORGANISM: Artificial Sequence
<220> FEATURE:
<223> OTHER INFORMATION: Synthetic Construct

<400> SEQUENCE: 23

Arg Arg Trp Leu Leu Leu Leu Asn Leu Leu Leu Leu Trp Arg Arg
1 5 10 15

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Trp
<220> FEATURE:
<221> NAME/KEY: MISC_FEATURE
<222> LOCATION: (4)..(7)
<223> OTHER INFORMATION: Xaa is D-Leu
<220> FEATURE:
<221> NAME/KEY: MISC_FEATURE
<222> LOCATION: (8)..(8)
<223> OTHER INFORMATION: Xaa is D-Asn
<220> FEATURE:
<221> NAME/KEY: MISC_FEATURE
<222> LOCATION: (9)..(12)
<223> OTHER INFORMATION: Xaa is D-Leu
<220> FEATURE:
<221> NAME/KEY: MISC_FEATURE
<222> LOCATION: (13)..(13)
<223> OTHER INFORMATION: Xaa is D-Trp
<220> FEATURE:
<221> NAME/KEY: MISC_FEATURE
<222> LOCATION: (14)..(15)
<223> OTHER INFORMATION: Xaa is D-Arg

<400> SEQUENCE: 24

Xaa Xaa Xaa Xaa Xaa Xaa Xaa Xaa Xaa Xaa Xaa Xaa Xaa Xaa Xaa
1 5 10 15

<210> SEQ ID NO 25
<211> LENGTH: 15
<212> TYPE: PRT
<213> ORGANISM: Artificial Sequence
<220> FEATURE:
<223> OTHER INFORMATION: Synthetic Construct

<400> SEQUENCE: 25

Arg Arg Trp Leu Leu Phe Leu Arg Leu Phe Leu Leu Trp Arg Arg
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: Synthetic Construct

<400> SEQUENCE: 26

Arg Arg Trp Leu Leu Ala Leu Arg Leu Ala Leu Leu Trp Arg Arg
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Arg Arg Trp Leu Leu Leu Leu Arg Leu Leu Leu Leu Phe Arg Arg
1 5 10 15

<210> SEQ ID NO 28
<211> LENGTH: 14
<212> TYPE: PRT
<213> ORGANISM: Artificial Sequence
<220> FEATURE:
<223> OTHER INFORMATION: Synthetic Construct

<400> SEQUENCE: 28

Arg Arg Trp Leu Leu Leu Gly Arg Leu Leu Leu Trp Arg Arg
1 5 10

<210> SEQ ID NO 29
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is Arg or absent
<220> FEATURE:
<221> NAME/KEY: MISC_FEATURE
<222> LOCATION: (3)..(3)
<223> OTHER INFORMATION: Xaa is Gly or absent
<220> FEATURE:
<221> NAME/KEY: MISC_FEATURE
<222> LOCATION: (5)..(5)
<223> OTHER INFORMATION: Xaa is Val, Ala, Asn, Gly, Arg, or Thr
<220> FEATURE:
<221> NAME/KEY: MISC_FEATURE
<222> LOCATION: (7)..(7)
<223> OTHER INFORMATION: Xaa is Asp, Arg, Val, Asn, or Ala
<220> FEATURE:
<221> NAME/KEY: MISC_FEATURE
<222> LOCATION: (9)..(9)
<223> OTHER INFORMATION: Xaa is Val, Tyr, Arg, Asn, or Thr
<220> FEATURE:
<221> NAME/KEY: MISC_FEATURE
<222> LOCATION: (11)..(11)
<223> OTHER INFORMATION: Xaa is Tyr, Ala, Gly, Val, Asn, or Thr
<220> FEATURE:
<221> NAME/KEY: MISC_FEATURE
<222> LOCATION: (13)..(13)
<223> OTHER INFORMATION: Xaa is Gly or absent
<220> FEATURE:
<221> NAME/KEY: MISC_FEATURE
<222> LOCATION: (14)..(15)
<223> OTHER INFORMATION: Xaa is Arg or absent

<400> SEQUENCE: 29

Xaa Xaa Xaa Trp Xaa Leu Xaa Leu Xaa Leu Xaa Tyr Xaa Xaa Xaa
1 5 10 15

<210> SEQ ID NO 30
<211> LENGTH: 15
<212> TYPE: PRT
<213> ORGANISM: Artificial Sequence
<220> FEATURE:
<223> OTHER INFORMATION: Synthetic Construct

<400> SEQUENCE: 30

Arg Arg Gly Trp Val Leu Asp Leu Val Leu Tyr Tyr Gly Arg Arg
1 5 10 15

<210> SEQ ID NO 31
<211> LENGTH: 12
<212> TYPE: PRT
<213> ORGANISM: Artificial Sequence
<220> FEATURE:
<223> OTHER INFORMATION: Synthetic Construct

<400> SEQUENCE: 31

Arg Arg Gly Trp Ala Leu Arg Leu Val Leu Ala Tyr
1 5 10

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Gly
<220> FEATURE:
<221> NAME/KEY: MISC_FEATURE
<222> LOCATION: (4)..(4)
<223> OTHER INFORMATION: Xaa is D-Trp
<220> FEATURE:
<221> NAME/KEY: MISC_FEATURE
<222> LOCATION: (5)..(5)
<223> OTHER INFORMATION: Xaa is D-Ala
<220> FEATURE:
<221> NAME/KEY: MISC_FEATURE
<222> LOCATION: (6)..(6)
<223> OTHER INFORMATION: Xaa is D-Leu
<220> FEATURE:
<221> NAME/KEY: MISC_FEATURE
<222> LOCATION: (7)..(7)
<223> OTHER INFORMATION: Xaa is D-Arg
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(9)
<223> OTHER INFORMATION: Xaa is D-Val
<220> FEATURE:
<221> NAME/KEY: MISC_FEATURE
<222> LOCATION: (10)..(10)
<223> OTHER INFORMATION: Xaa is D-Leu
<220> FEATURE:
<221> NAME/KEY: MISC_FEATURE
<222> LOCATION: (11)..(11)
<223> OTHER INFORMATION: Xaa is D-Ala
<220> FEATURE:
<221> NAME/KEY: MISC_FEATURE
<222> LOCATION: (12)..(12)
<223> OTHER INFORMATION: Xaa is D-Tyr

<400> SEQUENCE: 32

Xaa Xaa Xaa Xaa Xaa Xaa Xaa Xaa Xaa Xaa Xaa Xaa
1 5 10

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

Trp Ala Leu Arg Leu Tyr Leu Gly Val Tyr
1 5 10

<210> SEQ ID NO 34
<211> LENGTH: 9
<212> TYPE: PRT

<213> ORGANISM: Artificial Sequence
<220> FEATURE:
<223> OTHER INFORMATION: Synthetic Construct

<400> SEQUENCE: 34

Trp Val Leu Val Leu Arg Leu Gly Tyr
1 5

<210> SEQ ID NO 35
<211> LENGTH: 15
<212> TYPE: PRT
<213> ORGANISM: Artificial Sequence
<220> FEATURE:
<223> OTHER INFORMATION: Synthetic Construct

<400> SEQUENCE: 35

Arg Arg Gly Trp Asn Leu Arg Leu Arg Leu Val Tyr Gly Arg Arg
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: Synthetic Construct

<400> SEQUENCE: 36

Arg Arg Gly Trp Ala Leu Arg Leu Asn Leu Tyr Tyr Gly Arg Arg
1 5 10 15

<210> SEQ ID NO 37
<211> LENGTH: 15
<212> TYPE: PRT
<213> ORGANISM: Artificial Sequence
<220> FEATURE:
<223> OTHER INFORMATION: Synthetic Construct

<400> SEQUENCE: 37

Arg Arg Gly Trp Gly Leu Arg Leu Val Leu Tyr Tyr Gly Arg Arg
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: Synthetic Construct

<400> SEQUENCE: 38

Arg Arg Gly Trp Arg Leu Asn Leu Asn Leu Tyr Tyr Gly Arg Arg
1 5 10 15

<210> SEQ ID NO 39
<211> LENGTH: 15
<212> TYPE: PRT
<213> ORGANISM: Artificial Sequence
<220> FEATURE:
<223> OTHER INFORMATION: Synthetic Construct

<400> SEQUENCE: 39

Arg Arg Gly Trp Thr Leu Asn Leu Thr Leu Asn Tyr Gly Arg Arg
1 5 10 15

<210> SEQ ID NO 40
<211> LENGTH: 15
<212> TYPE: PRT
<213> ORGANISM: Artificial Sequence
<220> FEATURE:
<223> OTHER INFORMATION: Synthetic Construct

<400> SEQUENCE: 40

Arg Arg Gly Trp Asn Leu Ala Leu Thr Leu Thr Tyr Gly Arg Arg
1 5 10 15

<210> SEQ ID NO 41
<211> LENGTH: 25
<212> TYPE: PRT
<213> ORGANISM: Artificial Sequence
<220> FEATURE:
<223> OTHER INFORMATION: Synthetic Construct

<400> SEQUENCE: 41

Arg Arg Gly Phe Ser Leu Lys Leu Leu Leu Ser Tyr Arg Gly Trp Ala
1 5 10 15

Leu Leu Arg Leu Gly Tyr Gly Arg Arg
20 25

<210> SEQ ID NO 42
<211> LENGTH: 25
<212> TYPE: PRT
<213> ORGANISM: Artificial Sequence
<220> FEATURE:
<223> OTHER INFORMATION: Synthetic Construct

<400> SEQUENCE: 42

Arg Arg Gly Phe Ser Leu Lys Leu Ala Leu Leu Lys Asp Gly Trp Leu
1 5 10 15

Leu Leu Arg Leu Gly Tyr Gly Arg Arg
20 25

<210> SEQ ID NO 43
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is D-Arg
<220> FEATURE:
<221> NAME/KEY: MISC_FEATURE
<222> LOCATION: (3)..(3)
<223> OTHER INFORMATION: Xaa is D-Gly
<220> FEATURE:
<221> NAME/KEY: MISC_FEATURE
<222> LOCATION: (4)..(4)
<223> OTHER INFORMATION: Xaa is D-Phe
<220> FEATURE:
<221> NAME/KEY: MISC_FEATURE
<222> LOCATION: (5)..(5)
<223> OTHER INFORMATION: Xaa is D-Ser
<220> FEATURE:
<221> NAME/KEY: MISC_FEATURE
<222> LOCATION: (6)..(6)
<223> OTHER INFORMATION: Xaa is D-Leu
<220> FEATURE:
<221> NAME/KEY: MISC_FEATURE
<222> LOCATION: (7)..(7)
<223> OTHER INFORMATION: Xaa is D-Lys
<220> FEATURE:
<221> NAME/KEY: MISC_FEATURE
<222> LOCATION: (8)..(8)
<223> OTHER INFORMATION: Xaa is D-Leu
<220> FEATURE:
<221> NAME/KEY: MISC_FEATURE
<222> LOCATION: (9)..(9)
<223> OTHER INFORMATION: Xaa is D-Ala
<220> FEATURE:
<221> NAME/KEY: MISC_FEATURE
<222> LOCATION: (10)..(11)
<223> OTHER INFORMATION: Xaa is D-Leu
<220> FEATURE:
<221> NAME/KEY: MISC_FEATURE
<222> LOCATION: (12)..(12)
<223> OTHER INFORMATION: Xaa is D-Lys
<220> FEATURE:
<221> NAME/KEY: MISC_FEATURE
<222> LOCATION: (13)..(13)
<223> OTHER INFORMATION: Xaa is D-Asp
<220> FEATURE:
<221> NAME/KEY: MISC_FEATURE
<222> LOCATION: (14)..(14)
<223> OTHER INFORMATION: Xaa is D-Gly
<220> FEATURE:
<221> NAME/KEY: MISC_FEATURE
<222> LOCATION: (15)..(15)
<223> OTHER INFORMATION: Xaa is D-Trp
<220> FEATURE:
<221> NAME/KEY: MISC_FEATURE
<222> LOCATION: (16)..(18)
<223> OTHER INFORMATION: Xaa is D-Leu
<220> FEATURE:
<221> NAME/KEY: MISC_FEATURE
<222> LOCATION: (19)..(19)
<223> OTHER INFORMATION: Xaa is D-Arg
<220> FEATURE:
<221> NAME/KEY: MISC_FEATURE
<222> LOCATION: (20)..(20)
<223> OTHER INFORMATION: Xaa is D-Leu
<220> FEATURE:
<221> NAME/KEY: MISC_FEATURE
<222> LOCATION: (21)..(21)
<223> OTHER INFORMATION: Xaa is D-Gly
<220> FEATURE:
<221> NAME/KEY: MISC_FEATURE
<222> LOCATION: (22)..(22)
<223> OTHER INFORMATION: Xaa is D-Tyr
<220> FEATURE:
<221> NAME/KEY: MISC_FEATURE
<222> LOCATION: (23)..(23)
<223> OTHER INFORMATION: Xaa is D-Gly
<220> FEATURE:
<221> NAME/KEY: MISC_FEATURE
<222> LOCATION: (24)..(25)
<223> OTHER INFORMATION: Xaa is D-Arg

<400> SEQUENCE: 43

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa
            20                  25
```

<210> SEQ ID NO 44
<211> LENGTH: 26
<212> TYPE: PRT
<213> ORGANISM: Artificial Sequence
<220> FEATURE:
<223> OTHER INFORMATION: Synthetic Construct

<400> SEQUENCE: 44

```
Arg Arg Gly Phe Ser Leu Lys Leu Ala Leu Leu Tyr Arg Gly Trp Leu
1               5                   10                  15

Leu Leu Leu Arg Leu Gly Tyr Gly Arg Arg
            20                  25
```

<210> SEQ ID NO 45
<211> LENGTH: 26
<212> TYPE: PRT
<213> ORGANISM: Artificial Sequence
<220> FEATURE:

<223> OTHER INFORMATION: Synthetic Construct

<400> SEQUENCE: 45

```
Arg Arg Gly Phe Ser Leu Lys Leu Arg Leu Leu Tyr Arg Gly Trp Gly
1               5                   10                  15

Leu Ala Leu Arg Leu Gly Tyr Gly Arg Arg
            20                  25
```

<210> SEQ ID NO 46
<211> LENGTH: 26
<212> TYPE: PRT
<213> ORGANISM: Artificial Sequence
<220> FEATURE:
<223> OTHER INFORMATION: Synthetic Construct

<400> SEQUENCE: 46

```
Arg Arg Gly Phe Ser Leu Lys Leu Lys Leu Leu Tyr Arg Gly Trp Ala
1               5                   10                  15

Leu Ala Leu Arg Leu Gly Tyr Gly Arg Arg
            20                  25
```

<210> SEQ ID NO 47
<211> LENGTH: 26
<212> TYPE: PRT
<213> ORGANISM: Artificial Sequence
<220> FEATURE:
<223> OTHER INFORMATION: Synthetic Construct

<400> SEQUENCE: 47

```
Arg Arg Gly Phe Ser Leu Lys Leu Ala Leu Leu Lys Asp Gly Trp Leu
1               5                   10                  15

Leu Leu Leu Arg Leu Gly Tyr Gly Arg Arg
            20                  25
```

<210> SEQ ID NO 48
<211> LENGTH: 12
<212> TYPE: PRT
<213> ORGANISM: Artificial Sequence
<220> FEATURE:
<223> OTHER INFORMATION: Synthetic Construct

<400> SEQUENCE: 48

```
Pro Leu Ile Tyr Leu Arg Leu Leu Arg Gly Gln Phe
1               5                   10
```

<210> SEQ ID NO 49
<211> LENGTH: 11
<212> TYPE: PRT
<213> ORGANISM: Artificial Sequence
<220> FEATURE:
<223> OTHER INFORMATION: Synthetic Construct

<400> SEQUENCE: 49

```
Arg Arg Arg Arg Arg Arg Arg Arg Arg Trp Cys
1               5                   10
```

<210> SEQ ID NO 50
<211> LENGTH: 26
<212> TYPE: PRT
<213> ORGANISM: Artificial Sequence
<220> FEATURE:
<223> OTHER INFORMATION: Synthetic Construct

<400> SEQUENCE: 50

```
Gly Ile Gly Ala Val Leu Lys Val Leu Thr Thr Gly Leu Pro Ala Gly
```

```
1               5                   10                  15

Ile Ser Trp Ile Lys Arg Lys Arg Gln Gln
            20                  25


<210> SEQ ID NO 51
<211> LENGTH: 26
<212> TYPE: PRT
<213> ORGANISM: Artificial Sequence
<220> FEATURE:
<223> OTHER INFORMATION: Synthetic Construct

<400> SEQUENCE: 51

Gly Ile Gly Ala Val Leu Lys Gly Leu Ala Thr Gly Leu Pro Ala Gly
1               5                   10                  15

Ile Ser Trp Ile Lys Gln Gln Ala Gln Leu
            20                  25


<210> SEQ ID NO 52
<211> LENGTH: 26
<212> TYPE: PRT
<213> ORGANISM: Artificial Sequence
<220> FEATURE:
<223> OTHER INFORMATION: Synthetic Construct

<400> SEQUENCE: 52

Gly Ile Gly Ala Val Leu Lys Val Leu Ala Thr Gly Leu Pro Ala Leu
1               5                   10                  15

Ile Ser Trp Ile Lys Ala Ala Gln Gln Leu
            20                  25


<210> SEQ ID NO 53
<211> LENGTH: 26
<212> TYPE: PRT
<213> ORGANISM: Apis mellifera

<400> SEQUENCE: 53

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25


<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Arg Arg Gly Phe Ser Leu Lys Leu Ala Leu Leu
1               5                   10


<210> SEQ ID NO 55
<211> LENGTH: 12
<212> TYPE: PRT
<213> ORGANISM: Artificial Sequence
<220> FEATURE:
<223> OTHER INFORMATION: Synthetic Construct

<400> SEQUENCE: 55

Arg Arg Gly Phe Ser Leu Lys Leu Ala Leu Leu Lys
1               5                   10


<210> SEQ ID NO 56
```

```
<211> LENGTH: 11
<212> TYPE: PRT
<213> ORGANISM: Artificial Sequence
<220> FEATURE:
<223> OTHER INFORMATION: Synthetic Construct

<400> SEQUENCE: 56

Leu Ala Leu Leu Lys Asp Gly Trp Leu Leu Leu
1               5                   10


<210> SEQ ID NO 57
<211> LENGTH: 13
<212> TYPE: PRT
<213> ORGANISM: Artificial Sequence
<220> FEATURE:
<223> OTHER INFORMATION: Synthetic Construct

<400> SEQUENCE: 57

Lys Leu Ala Leu Leu Lys Asp Gly Trp Leu Leu Leu Arg
1               5                   10


<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

Trp Leu Leu Leu Arg Leu Gly Tyr Gly Arg Arg
1               5                   10


<210> SEQ ID NO 59
<211> LENGTH: 14
<212> TYPE: PRT
<213> ORGANISM: Artificial Sequence
<220> FEATURE:
<223> OTHER INFORMATION: Synthetic Construct

<400> SEQUENCE: 59

Lys Asp Gly Trp Leu Leu Leu Arg Leu Gly Tyr Gly Arg Arg
1               5                   10


<210> SEQ ID NO 60
<211> LENGTH: 22
<212> TYPE: DNA
<213> ORGANISM: Influenza A virus

<400> SEQUENCE: 60

gaccratcct gtcacctctg ac                                              22


<210> SEQ ID NO 61
<211> LENGTH: 24
<212> TYPE: DNA
<213> ORGANISM: Influenza A virus

<400> SEQUENCE: 61

agggcattyt ggacaaakcg tcta                                            24


<210> SEQ ID NO 62
<211> LENGTH: 24
<212> TYPE: DNA
<213> ORGANISM: Influenza A virus
<220> FEATURE:
<221> NAME/KEY: modified_base
<222> LOCATION: (1)..(1)
<223> OTHER INFORMATION: FAM
```

-continued

```
<220> FEATURE:
<221> NAME/KEY: modified_base
<222> LOCATION: (24)..(24)
<223> OTHER INFORMATION: BHQ1

<400> SEQUENCE: 62

tgcagtcctc gctcactggg cacg                                  24


<210> SEQ ID NO 63
<211> LENGTH: 19
<212> TYPE: DNA
<213> ORGANISM: Homo sapiens

<400> SEQUENCE: 63

agatttggac ctgcgagcg                                        19


<210> SEQ ID NO 64
<211> LENGTH: 20
<212> TYPE: DNA
<213> ORGANISM: Homo sapiens

<400> SEQUENCE: 64

gagcggctgt ctccacaagt                                       20


<210> SEQ ID NO 65
<211> LENGTH: 23
<212> TYPE: DNA
<213> ORGANISM: Homo sapiens
<220> FEATURE:
<221> NAME/KEY: modified_base
<222> LOCATION: (1)..(1)
<223> OTHER INFORMATION: CY3
<220> FEATURE:
<221> NAME/KEY: modified_base
<222> LOCATION: (23)..(23)
<223> OTHER INFORMATION: BHQ2

<400> SEQUENCE: 65

ttctgacctg aaggctctgc gcg                                   23
```